US012776029B2

(12) United States Patent
Jia et al.

(10) Patent No.: US 12,776,029 B2
(45) Date of Patent: Oct. 27, 2026

(54) SYSTEMS AND METHODS FOR GENERATING BIOMARKER ACTIVATION MAPS

(71) Applicant: Oregon Health & Science University, Portland, OR (US)

(72) Inventors: Yali Jia, Portland, OR (US); Pengxiao Zang, Portland, OR (US)

(73) Assignee: Oregon Health & Science University, Portland, OR (US)

( * ) Notice: Subject to any disclaimer, the term of this patent is extended or adjusted under 35 U.S.C. 154(b) by 639 days.

(21) Appl. No.: 18/129,649

(22) Filed: Mar. 31, 2023

(65) Prior Publication Data

US 2023/0316510 A1 Oct. 5, 2023

Related U.S. Application Data

(60) Provisional application No. 63/356,999, filed on Jun. 29, 2022, provisional application No. 63/326,638, filed on Apr. 1, 2022.

(51) Int. Cl.

| | |
|---|---|
| ***G06K 9/00*** | (2022.01) |
| ***A61B 3/10*** | (2006.01) |
| ***G06F 3/14*** | (2006.01) |
| ***G06T 7/00*** | (2017.01) |
| ***G06V 10/764*** | (2022.01) |
| ***G16H 30/40*** | (2018.01) |
| ***G16H 50/20*** | (2018.01) |

(52) U.S. Cl.
CPC ............ *G06T 7/0012* (2013.01); *A61B 3/102* (2013.01); *G06F 3/14* (2013.01); *G06V 10/764* (2022.01); *G16H 30/40* (2018.01); *G16H 50/20* (2018.01); *G06T 2207/10101* (2013.01); *G06T 2207/20081* (2013.01); *G06T 2207/20084* (2013.01)

(58) Field of Classification Search
None
See application file for complete search history.

(56) References Cited

U.S. PATENT DOCUMENTS

2020/0272864 A1* 8/2020 Faust .................. G06V 10/764
2021/0327062 A1* 10/2021 Choi ........................ A61B 5/00
2024/0268699 A1* 8/2024 Panes Saavedra ... A61B 5/4878

* cited by examiner

*Primary Examiner* — Wei Wen Yang
(74) *Attorney, Agent, or Firm* — C. Rachal Winger; Shan Liao; Lee & Hayes PC

(57) ABSTRACT

Methods and systems for generating biomarker activation maps (BAMs) are described. An example method includes identifying a medical image depicting at least a portion of a subject; generating a BAM by inputting the medical image into a trained, U-shaped neural network (NN); and outputting the BAM overlaying the medical image, the BAM indicating at least one biomarker depicted in the medical image that is indicative of a disease.

14 Claims, 27 Drawing Sheets
(17 of 27 Drawing Sheet(s) Filed in Color)

(A) OCTA channel of a false positive classification (B) OCTA channel of a false negative classification

SYSTEMS AND METHODS FOR GENERATING BIOMARKER ACTIVATION MAPS

CROSS-REFERENCE TO RELATED APPLICATIONS

This application claims the benefit of U.S. Provisional App. No. 63/326,638, filed on Apr. 1, 2022, and U.S. Provisional App. No. 63/356,999, filed on Jun. 29, 2022, each of which is incorporated by reference herein in its entirety.

STATEMENT REGARDING FEDERALLY SPONSORED RESEARCH

This invention was made with Government support under R01 EY027833 and R01 EY024544 awarded by the National Institutes of Health. The Government has certain rights in the invention.

TECHNICAL FIELD

This disclosure relates generally to systems, devices, and methods for generating biomarker activation maps indicating biomarkers-of-interest in medical images.

BACKGROUND

Convolutional neural networks (CNNs), a class of deep learning models, have been widely used in the automated disease classification tasks based on different imaging modalities (LeCun Y et al., Nature. 2015; 521(7553):436-44; Litjens G et al., Medical image analysis, 2017, 42: 60-88; Shen D et al., Annual review of biomedical engineering, 2017, 19: 221-48; Suganyadevi S et al., International Journal of Multimedia Information Retrieval, 2022, 11(1): 19-38). Compared to traditional prediction model and machine learning techniques, CNN-based systems have achieved the state-of-the-art performance in a variety of the disease classification tasks (Litjens G et al., Medical image analysis, 2017, 42: 60-88; Shen D et al., Annual review of biomedical engineering, 2017, 19: 221-48; Suganyadevi S et al., International Journal of Multimedia Information Retrieval, 2022, 11(1): 19-38). An automated disease classification system can be evaluated in terms of interpretability in addition to performance. A conventional CNN-based disease classification system can output an indication that a disease is present or not present based on analyzing a medical image. However, clinicians (e.g., doctors) are unwilling to rely solely on a classification system for disease diagnosis. Clinicians seek to confirm that the disease classification system is accurately relying on clinically meaningful features. However, conventional classification systems work like a “black box” which provide little interpretability to the user clinician. For example, a disease classification system may indicate that a particular disease is present in a medical image without indicating what structures in the image are indicative of the disease. The poor interpretability caused by the “black box” issue has become one of the major challenges for the widely real-world clinical practice of the CNN-based disease classification systems (He J et al., Nature medicine, 2019, 25(1): 30-36; Gerke S et al., Artificial intelligence in healthcare. Academic Press, 2020: 295-36; Salahuddin Z et al., Computers in biology and medicine, 2022, 140: 105111).

To solve the “black box” issue, several visualization methods have been used to provide interpretability to CNN-based disease classification systems. For example, a method based on gradients respect to the input of CNN has been evaluated on a diabetic retinopathy (DR) classification task (Sundararajan et al., Axiomatic attribution for deep networks in Proceedings of the 34th International Conference on Machine Learning-Volume 70, pages 3319-28. JMLR. org, 2017). Class activation maps (CAMs) have been also used in several disease classification tasks (Zhou B et al., Learning Deep Features for Discriminative Localization in Proceedings of the IEEE Computer Society Conference on Computer Vision and Pattern Recognition; 2016; Selvaraju R R et al., Grad-CAM: visual explanations from deep networks via gradient-based localization in: Proceedings of the IEEE International Conference on Computer Vision; 2017; Chattopadhay A et al., Grad-CAM++: Generalized gradient-based visual explanations for deep convolutional networks in Proceedings—2018 IEEE Winter Conference on Applications of Computer Vision, WACV 2018; 2018; Li K et al. Tell me where to look: guided attention inference network in Proceedings of the IEEE Computer Society Conference on Computer Vision and Pattern Recognition; 2018).

However, these visualization methods are inadequate for medical image-based diagnosis. Many classification systems used for these visualization methods were originally proposed for general image classification, such as determining whether an image depicts a cat or a bird. In general image classification, each class (e.g., cat or bird) is identified based on unique characteristics (e.g., the presence of whiskers or wings). Classes do not share features. For example, a bird has wings, but a cat does not, and a cat has whiskers, but a bird does not.

In contrast to general image classification, medical images often depict different diseases (or disease severities) with the same or similar features. For instance, a retina exhibiting non-referrable diabetic retinopathy (DR) may have similar features to a retina exhibiting referrable DR. In various examples, the identification of a non-disease or lower severity class is based on the absence of specific biomarkers that belong to the disease or higher severity. In addition, while general images are often defined using a single channel (e.g., grayscale or RGB images), diseases may be identifiable from medical that are defined using multiple channels, respectively corresponding to different imaging modalities (each channel per modality). Current interpretability methods can only generate one-channel heatmaps which cannot be used to differentiate the contributions of features depicted by different imaging modalities. Therefore, current interpretability methods are insufficient for real-world clinical practice.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The detailed description is described with reference to the accompanying figures. In the figures, the left-most digit(s) of a reference number identifies the figure in which the reference number first appears. The use of the same reference numbers in different figures indicates similar or identical components or features.

FIG. 5A illustrates example signaling for training a BAM model using a disease image. FIG. 5B illustrates example signaling for training a BAM model using a non-disease image.

FIGS. 22A to 21E illustrate BAMs generated in the ablation experiments. Large vessels highlighted by the three variations are marked by blue arrows.

DETAILED DESCRIPTION

Figure 1:
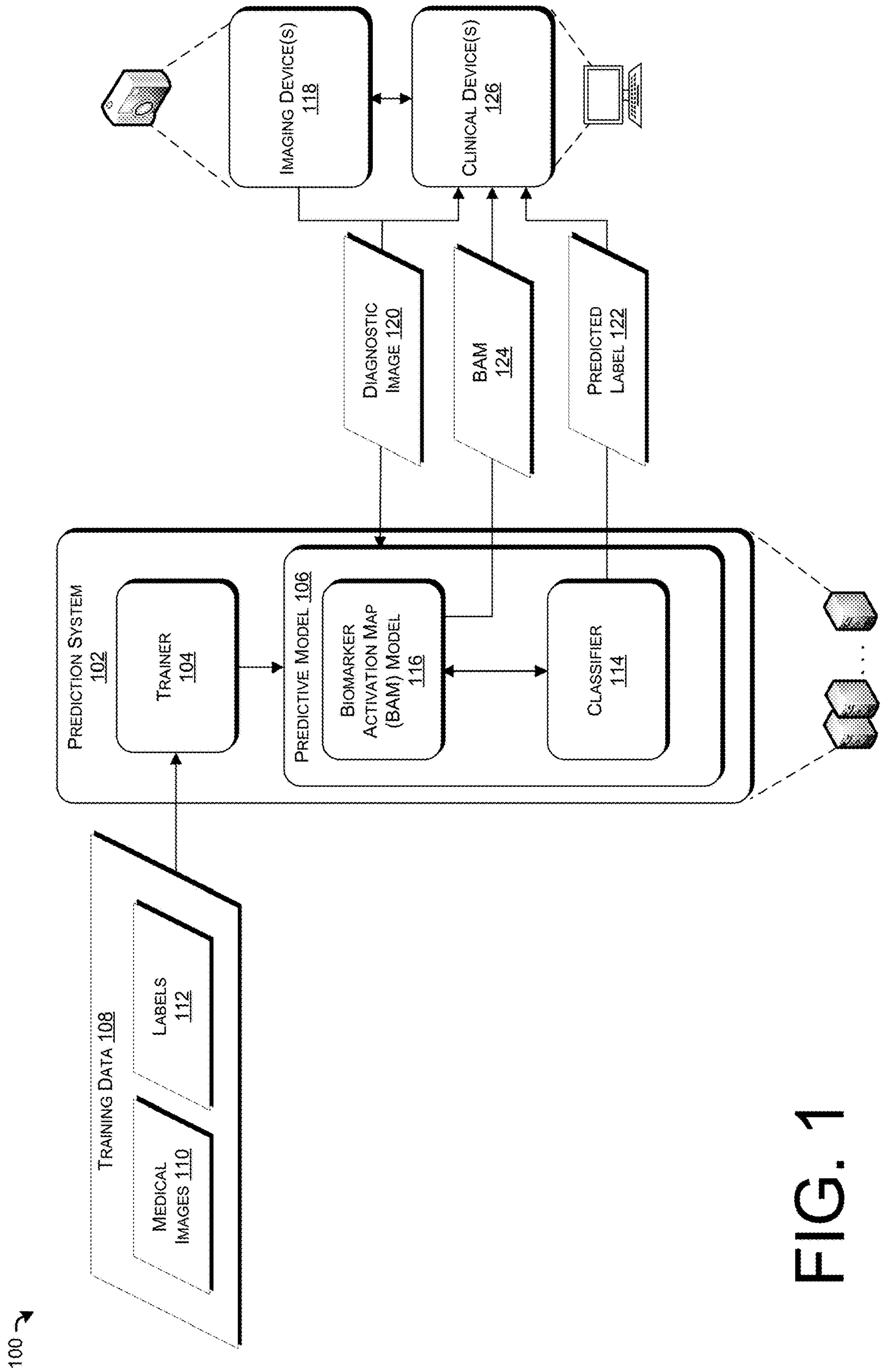
FIG. 1 illustrates an example environment for improving interpretability of computer-based disease classification.

This disclosure describes systems, devices, and techniques for generating biomarker activation maps (BAMs) that highlight local elements in images that contribute to disease classifier output. These BAMs may be presented, for example, as heatmaps which provide biomarker-level interpretability, and facilitate the new biomarker discovery.

In order to provide sufficient interpretability for the CNN-based disease classification system, a novel BAM generation framework is described herein. The BAM generation framework was designed based on generative adversarial learning (see Goodfellow I et al., Advances in neural information processing systems, 2014, 27; Mirza M et al., Conditional generative adversarial nets[J]. arXiv preprint arXiv: 1411.1784, 2014; Isola Petal., Proceedings of the IEEE conference on computer vision and pattern recognition. 2017: 1125-34; Zhu J Y et al., Proceedings of the IEEE international conference on computer vision. 2017: 2223-32) with a main generator and an assistant generator. The generated BAM can accurately highlight different CNN-selected biomarkers. By referring to a generated BAM, clinicians can quickly discern each highlighted biomarker and determine whether this biomarker is clinically meaningful before relying on the results of an automated disease classification system. In addition, the highlighted biomarkers in the BAM can also help clinicians make decisions about treatment disease management. By providing sufficient interpretability, BAM generation frameworks described herein can improve deep-learning-aided disease classification systems, thereby leading to broader use of disease classification systems in real-world clinical practice.

In some particular examples, a BAM generation framework was evaluated on a DR classification system based on optical coherence tomography (OCT) and OCT angiography (OCTA). DR is a leading cause of preventable blindness globally. DR has a number of distinct severities with different clinical implications. For example, eyes with referable DR (rDR) should be referred to an ophthalmologist (Wilkinson C P et al., Ophthalmology. 2003; 110(9):1677-82; Wong T Y et al., Ophthalmology, 2018; 125(10):1608-22; Flaxel C J, Adelman R A, Bailey S T, et al. Diabetic retinopathy preferred practice pattern, Ophthalmology, 2020; 127(1):66-145; Antonetti D A et al., N. Engl. J. Med. 2012; 366:1227-39). An OCT scan can generate depth-resolved, micrometer-scale-resolution images of ocular fundus tissue based on reflectance signals obtained using interferometric analysis of low coherence light (Huang D et al., Science. 1991; 254 (5035):1178-81). By scanning multiple B-frames at the same position, change in the OCT reflectance properties can be measured as, e.g., decorrelation values to differentiate vasculature from static tissues. This technique is called OCTA, and it can provide high-resolution images of the microvasculature of the retina (Makita S et al., Optics express. 2006; 14(17):7821-40; An L et al., Optics express, 2008; 16(15): 11438-52; Jia Y et al., Opt. Express. 2012; 20(4):4710-25). The biomarkers captured by OCT and OCTA have demonstrated superior potential for diagnosing and classifying DR compared to traditional imaging modalities (Jia Y et al., PNAS 2015; 112(18):E2395-402; Hwang T S et al., JAMA ophthalmol. 2016; 134(12):1411-19; Zhang M et al., Investig. Ophthalmol. Vis. Sci. 2016; 57(13):5101-06; Hwang T S et al., JAMA ophthalmol. 2016; 134(4):367-73; Hwang T S et al., Retina. 2015; 35(11):2371).

To provide interpretability to a CNN-based classifier, several methods have been proposed to interpret the results of the CNN by generating heatmap that indicates local relevancy for a given input image. Three methods for interpretability include gradient-based, CAM-based, and propagation-based methods.

In gradient-based methods, the heatmap is generated based on the gradients of different convolutional layers with respect to the input (Sundararajan et al., Axiomatic attribution for deep networks in Proceedings of the 34th International Conference on Machine Learning-Volume 70, pages 3319-28. JMLR. org, 2017; Avanti Shrikumar et al., Not just a black box: Learning important features through propagating activation differences, arXiv preprint arXiv:1605.01713, 2016; Daniel Smilkov, et al., Smoothgrad: removing noise by adding noise, arXiv preprint arXiv:1706.03825, 2017; Suraj Srinivas et al., Advances in Neural Information Processing Systems, pages 4126-35, 2019). Such as M. Sundararajan et al. proposed the Integrated Gradients which based on the multiplication between the average gradient and linear interpolation of the input (Sundararajan et al., Axiomatic attribution for deep networks in Proceedings of the 34th International Conference on Machine Learning-Volume 70, pages 3319-28. JMLR. org, 2017). In addition, S. Srinivas et al. proposed the Full-gradient method which not only based on the gradients respect to the input but also the bias (Suraj Srinivas et al., Advances in Neural Information Processing Systems, pages 4126-35, 2019). However, in practice, the outputs from these gradient-based methods are class-agnostic which means the generated heatmaps are similar between different classes (Chefer H et al., Proceedings of the IEEE/CVF Conference on Computer Vision and Pattern Recognition. 2021: 782-91). The unique biomarkers only belong to the medical image of disease or higher severity cannot be distinguished from the shared features among all classes. In addition, only one-channel heatmap can be generated from the gradient-based methods.

The CAM-based methods are class-specific and have been widely used in the CNN-based DR screening (Zhou B et al., Learning Deep Features for Discriminative Localization in Proceedings of the IEEE Computer Society Conference on Computer Vision and Pattern Recognition; 2016; Selvaraju R R et al., Grad-CAM: visual explanations from deep networks via gradient-based localization in: Proceedings of the IEEE International Conference on Computer Vision; 2017; Chattopadhay A et al., Grad-CAM++: Generalized gradient-based visual explanations for deep convolutional networks in Proceedings—2018 IEEE Winter Conference on Applications of Computer Vision, WACV 2018; 2018; Li K et al. Tell me where to look: guided attention inference network in Proceedings of the IEEE Computer Society Conference on Computer Vision and Pattern Recognition, 2018). The basic CAM method combines the class-specific weight and the output of last convolutional layer before global average pooling. The Grad-CAM introduces the gradients of target convolutional layers to the basic CAM. However, the CAM-based methods only use the highest convolutional layer, which generates low-resolution heatmaps. In the reviewing of the CAMs, clinicians still need to manually discern the biomarkers inside the coarsely highlighted regions (FIG. 1(A)), which is time consuming and not clinically practical. Same as the gradient-based methods, the CAM-based methods can only generate one-channel heatmap, too.

Propagation-based methods are mostly based on the Deep Taylor Decomposition (DTD) framework (Gregoire Montavon et al., Pattern Recognition, 65:211-22, 2017; Sebastian Bach et al., PloS one, 10(7):e0130140, 2015; Woo-Jeoung Nam et al., Relative attributing propagation: Interpreting the comparative contributions of individual units in deep neural networks, arXiv:1904.00605, 2019; Shir Gur et al., AAAI, 2021; Avanti Shrikumar et al., Proceedings of the 34th International Conference on Machine Learning-Volume 70, pp. 3145-53, 2017; Lundberg et al., Advances in Neural information Processing Systems, pp. 4765-74, 2017; Gu et al., Asian Conference on Computer Vision, pp, 119-34, 2018; Iwana et al., Explaining convolutional neural networks using softmax gradient layer-wise relevance propagation, arXiv:1908.04351, 2019). In these methods, the heatmap is generated by tracing the contribution of the output back to the input using back propagation through the CNN based on the DTD principle. Such as S. Bach et al. proposed the Layer-wise Relevance Propagation (LRP) method calculates the contribution of each element in the input back propagated from the output using DTD principle. However, some of these methods are class-agnostic in practical applications. To solve this issue, the class-specific propagation-based methods are proposed. J. Gu et al. proposed the Contrastive-LRP method in which the contributions based on non-target classes are averagely removed from the heatmap. B. K. Iwana et al. proposed the Softmax-Gradient-LRP in which the contribution of each non-target class is removed based on their own probability value after softmax. Compared to Grad-CAMs, the generated heatmaps by these class-specific LRP methods have higher resolution. However, as shown in at least FIG. 16, the highlighted regions in these heatmaps are inaccurate compared to the DR-related biomarkers.

Several methods which are not belong to the three main categories are also proposed to interpret the CNN-based classifier, such as the input-modification-based methods (B. Alipanahi et al., Nature Biotechnology, 33(8):831-38, 2015; M. D. Zeiler et al., European Conference on Computer Vision, pp. 818-33, 2014; B. Zhou et al., International Conference on Learning Representations, 2014; J. Zhou et al., Nature Methods, 12(10):931-34, 2015; A. Mahendran et al., International Journal of Computer Vision, 120(3):233-55, 2016; C. Olah et al., Feature visualization. Distill, 2017), the saliency-based methods (Piotr Dabkowski et al., Advances in Neural Information Processing Systems, pp. 6970-79, 2017; Karen Simonyan et al., Deep inside convolutional networks: Visualising image classification models and saliency maps, arXiv:1312.6034, 2013; Brent Mittelstadt et al., Proceedings of the conference on fairness, accountability, and transparency, pp. 279-88, 2019; Bolei Zhou et al., Interpreting deep visual representations via network dissection, IEEE transactions on pattern analysis and machine intelligence, 2018), the activation maximization method (Dumitru Erhan et al., University of Montreal, 1341(3):1, 2009), excitation backprop method (Jianming Zhang et al., International Journal of Computer Vision, 126(10):1084-02, 2018), and perturbation methods (Ruth Fong et al., Proceedings of the IEEE International Conference on Computer Vision, pp. 2950-58, 2019; Ruth C Fong et al., Proceedings of the IEEE International Conference on Computer Vision, pp. 3429-37, 2017), and other techniques (Jianbo Chen et al., L-shapley and c-shapley: Efficient model interpretation for structured data, International Conference on Learning Representations, 2019; J. T. Springenberg et al., Striving for simplicity: The all convolutional net in International Conference on Learning Representations, 2015). Compared to the methods belong to the three main categories, the accuracy of these methods is usually lower in practice (Chefer H et al., Proceedings of the IEEE/CVF Conference on Computer Vision and Pattern Recognition. 2021: 782-91). In addition, most of these methods can only generate one-channel heatmap, in which the contribution between different image modalities cannot be differentiated.

The BAM-based frameworks described herein are superior to other interpretability techniques, such as the gradient-, CAM-, and propagation-based methods. Accordingly, the BAM-based frameworks described herein provide practical improvements to the technical field of medical imaging classification and interpretability.

Example Definitions

As used herein, the term "segmentation," and its equivalents, can refer to a process of defining an image of a retina into regions. For instance, a segmentation method can be performed by defining an area of an angiogram that depicts a CNV area As used herein, the term "reflectance image" can refer to a two-dimensional B-scan of a retina, wherein the values of individual pixels of the reflectance image correspond to reflectance intensity values observed by an OCT system at respective positions corresponding to the individual pixels. One dimension of the B-scan can be defined along a depth direction. Another direction can be defined along a lateral direction of the retina (e.g., defined in a direction parallel to a direction defined between the eyes of the subject).

As used herein, the term "Optical Coherence Tomography (OCT)," and its equivalents, can refer to a noninvasive low-coherence interferometry technique that can be used to obtain depth images of tissues, such as structures within the eye. In various implementations, OCT can be used to obtain depth images of retinal structures (e.g., layers of the retina). In some cases, OCT can be used to obtain a volumetric image of a tissue. For example, by obtaining multiple depth images of retinal structures along different axes, OCT can be used to obtain a volumetric image of the retina.

As used herein, the term "Optical Coherence Tomographic Angiography (OCTA)," and its equivalents, can refer to a subset of OCT techniques that obtain images based on flow (e.g., blood flow) within an imaged tissue. Accordingly, OCTA can be used to obtain images of vasculature within tissues, such as the retina. In some cases, OCTA imaging can be performed by obtaining multiple OCT scans of the same area of tissue at different times, in order to analyze motion or flow in the tissue that occurred between the different times.

As used herein, the term "OCT image," and its equivalents, can refer to an OCT reflectance image, an OCTA image, or a combination thereof. An OCT image may be two-dimensional (e.g., one 2D projection image or one 2D depth image) or three-dimensional (e.g., a volumetric image).

As used herein, the terms "vascular," "perfusion," and the like can refer to an area of an image that depicts vasculature. In some cases, a perfusion area can refer to an area that depicts a blood vessel or another type of vasculature.

As used herein, the terms "avascular," "nonperfusion," and the like can refer to an area of an image that does not depict vasculature. In some cases, a nonperfusion area can refer to an area between blood vessels or other types of vasculature.

As used herein, the terms "blocks," "layers," and the like can refer to devices, systems, and/or software instances (e.g., Application Programming Interfaces (APIs), Virtual Machine (VM) instances, or the like) that generates an output by apply an operation to an input. A "convolutional block," for example, can refer to a block that applies a convolution operation to an input (e.g., an image). When a first block is in series with a second block, the first block may accept an input, generate an output by applying an operation to the input, and provide the output to the second block, wherein the second block accepts the output of the first block as its own input. When a first block is in parallel with a second block, the first block and the second block may each accept the same input, and may generate respective outputs that can be provided to a third block. In some examples, a block may be composed of multiple blocks that are connected to each other in series and/or in parallel. In various implementations, one block may include multiple layers.

In some cases, a block can be composed of multiple neurons. As used herein, the term "neuron," or the like, can refer to a device, system, and/or software instance (e.g., VM instance) in a block that applies a kernel to a portion of an input to the block.

As used herein, the term "kernel," and its equivalents, can refer to a function, such as applying a filter, performed by a neuron on a portion of an input to a block.

As used herein, the term "pixel," and its equivalents, can refer to a value that corresponds to an area or volume of an image. In a grayscale image, the value can correspond to a grayscale value of an area of the grayscale image. In a color image, the value can correspond to a color value of an area of the color image. In a binary image, the value can correspond to one of two levels (e.g., a 1 or a 0). The area or volume of the pixel may be significantly smaller than the area or volume of the image containing the pixel. In examples of a line defined in an image, a point on the line can be represented by one or more pixels. A "voxel" is an example of a pixel spatially defined in three dimensions.

As used herein, the terms "rectified linear activation function," "rectified linear unit," "Relu," and their equivalents, may refer to a function that returns 0 if the input is negative and returns the input if the input is positive. When applied to an image including multiple pixels (or voxels), the Relu function is applied to the image on a pixel-by-pixel basis, such that the output of the Relu function is an image with pixels that only have positive values.

As used herein, the terms "hyperbolic tangent activation function," "Tanh," and their equivalents, may refer to an activation function defined according to the following equation:

$$y = \frac{e^x - e^{-x}}{e^x + e^{-x}}$$

wherein x is the input of the Tanh function and y is the output of the Tanh function. When applied to an image including multiple pixels (or voxels), the Tanh function is applied to the image on a pixel-by-pixel basis, such that the output of the Tanh function is an image with pixels that each have values within a range of −1 to 1.

Particular Implementations

Some particular implementations of the present disclosure will now be described with reference to FIGS. 1 through 10. However, the implementations described with reference to FIGS. 1 through 10 are not exhaustive.

FIG. 1 illustrates an example environment 100 for improving interpretability of computer-based disease classification. As shown, a prediction system 102 includes a trainer 104 and a predictive model 106. The prediction system 102, for instance, is embodied in hardware, software, or a combination thereof. In various implementations, the predictive model 106 includes one or more deep learning (DL) networks, such as neural networks (NNs), that are defined according to one or more parameters. The trainer 104 is configured to optimize the parameter(s) of the predictive model 106 based on training data 108.

The training data 108 includes medical images 110 of various subjects. In various implementations, the subjects include at least one subject without a disease and at least one subject with the disease. In some cases, the disease includes multiple levels of severity. The subjects depicted in the medical images 108 may include at least one subject exhibiting the disease with each level of severity. In various implementations, the medical images 110 are two-dimensional (2D) images and/or three-dimensional (3D) images.

The medical images 110 may be obtained using one or more imaging modalities. For example, the medical images 110 include one or more x-ray images, magnetic resonance imaging (MRI) images, functional MRI (fMRI) images, single-photon emission computerized tomography (SPECT) images, positron emission tomography (PET) images, ultrasound images, infrared images, computed tomography (CT) images, optical coherence tomography (OCT) images, OCT angiography (OCTA) images, color fundus photograph (CFP) images, fluorescein angiography (FA) images, ultra-widefield retinal images, or any combination thereof. The medical images 110 include 3D volumetric images, such as CT images, in various cases. In some examples, the medical images 110 include 2D projection images, such as x-ray projection images. According to some examples, the medical images 110 depict physiological parameters of the subjects, such as time-series waveforms of electrocardiograms (ECGs), electroencephalographs (EEGs), or the like. The medical images 110 depict the same one or more physiological structures of different subjects. For instance, the medical images 110 may depict the brains of the subjects, the retinas of the subjects, the bones of a subject, or the like.

In various cases, each of the medical images 110 includes multiple channels. In some cases, an example medical image 110 includes a first channel corresponding to a first imaging modality and a second channel corresponding to a second imaging modality. In various implementations, each channel of the example medical image 110 depicts the same at least portion of an example subject. For instance, the medical image 110 includes a first channel representing an OCT image of a retina of an eye of the subject, and includes a second channel representing an OCTA image of the retina of the eye of the subject.

The training data 108 further includes labels 112. The labels 112 may indicate whether the subjects depicted in the medical images 110 exhibit the disease. If the disease has multiple levels of severity, the labels 112 may further indicate the level of severity of the disease exhibited by each of the subjects. In some cases, the labels 112 are generated by at least one expert grader (e.g., a physician with specialized training for identifying the disease in medical images). According to some examples, the expert grader(s) may view different images of the subjects than those included in the medical images 110 in the training data 108. For example, the expert grader(s) may generate the labels 112 based on fundus images of the subjects, but the medical images 110 may include OCT and OCTA images of the subjects rather than the fundus images.

The trainer 104 may optimize the parameters of one or more NNs in the predictive model 106 based on the training data 108. In particular, the predictive model 106 includes a classifier 114 that includes one or more NNs. In some cases, the predictive model 106 is a deep learning model, such as a Convolutional Neural Network (CNN) model. The term "Neural Network (NN)," and its equivalents, may refer to a model with multiple hidden layers, wherein the model receives an input (e.g., an image) and transforms the input by performing operations via the hidden layers. An individual hidden layer may include multiple "neurons," each of which may be disconnected from other neurons in the layer. An individual neuron within a particular layer may be connected to multiple (e.g., all) of the neurons in the previous layer. A NN may further include at least one fully connected layer that receives a feature map output by the hidden layers and transforms the feature map into the output of the NN.

As used herein, the term "CNN," and its equivalents, may refer to a type of NN model that performs at least one convolution (or cross correlation) operation on an input image and may generate an output image based on the convolved (or cross-correlated) input image. A CNN may include multiple layers that transforms an input image (e.g., a 3D volume) into an output image via a convolutional or cross-correlative model defined according to one or more parameters. The parameters of a given layer may correspond to one or more filters, which may be digital image filters that can be represented as images. A filter in a layer may correspond to a neuron in the layer. A layer in the CNN may convolve or cross correlate its corresponding filter(s) with the input image in order to generate the output image. In various examples, a neuron in a layer of the CNN may be connected to a subset of neurons in a previous layer of the CNN, such that the neuron may receive an input from the subset of neurons in the previous layer and may output at least a portion of an output image by performing an operation (e.g., a dot product, convolution, cross-correlation, or the like) on the input from the subset of neurons in the previous layer. The subset of neurons in the previous layer may be defined according to a "receptive field" of the neuron, which may also correspond to the filter size of the neuron. U-Net (see, e.g., Ronneberger, et al., arXiv: 1505.04597v1, 2015) is an example of a CNN model.

The trainer 104 may optimize the classifier 114 such that the classifier 114 accurately outputs the labels 112 in response to receiving the medical images 110 as inputs. Examples of the classifier 114 include, for instance, a deep-learning aided classifier, such as an eye disease classifier (e.g., configured to identify diabetic retinopathy, age-related macular degeneration, glaucoma, etc.), a tumor classifier (e.g., configured to identify the presence of tumors in the brain, lung, liver, etc.), or another type of disease classifier. The classifier 114 may identify the presence of disease in images generated using at least one imaging modality, such as OCT, CFP, FA, CT, MRI, or the like. The predictive model 106 further includes a biomarker activation map (BAM) model 116. The trainer 104 may additionally optimize one or more parameters of the BAM model 116 based on the training data 108. In various implementations, the classifier 114, once trained, may rely on the presence of one or more biomarkers in the medical images 110 to accurately synthesize the labels 112. The BAM model 116, once trained, is configured to identify the biomarker(s) in the medical images 110. In various implementations, the BAM model 116 is trained based on the trained classifier 114. For example, the labels 112 include the prediction results of the medical images 110 generated based on the trained classifier 114, and those prediction results are used to train the BAM model 116.

The trainer 104 can perform various techniques to train (e.g., optimize the parameters of) the classifier 114 and/or BAM model 116 using the training data 108. For instance, the trainer 104 may perform a training technique utilizing stochastic gradient descent with backpropagation, or any other machine learning training technique known to those of skill in the art. In some implementations, the trainer 104 utilizes adaptive label smoothing to reduce overfitting. According to some cases, the trainer 104 applies L1-L2 regularization and/or learning rate decay to train the classifier 114 and/or BAM model 116. In some examples, the trainer 104 trains the BAM model 116 by defining a main generator and an assistant generator, as described in further detail before.

In various implementations, the trainer 104 may be configured to train the predictive model 112 by optimizing various parameters within the predictive model 112 (e.g., within the classifier 114 and/or BAM model 116) based on the training data 106. For example, the trainer 104 may input the retinal images 108 into the predictive model 112 and compare outputs of the predictive model 112 to the gradings 110. The trainer 104 may further modify various parameters of the predictive model 112 (e.g., filters in the neural network 114) in order to ensure that the outputs of the predictive model 112 are sufficiently similar and/or identical to the gradings 110. For instance, the trainer 104 may identify values of the parameters that result in a minimum of loss between the outputs of the predictive model 112 and the gradings 110.

Once the classifier 114 and the BAM model 116 are trained, the predictive model 106 can be utilized to analyze new medical images. For example, at least one imaging device 118 is configured to generate a diagnostic image 120. The diagnostic image 120 depicts at least a portion of a subject (e.g., a patient). In various examples, the subject depicted in the diagnostic image 120 is different than the subjects depicted in the medical images 110 used to train the predictive model 106. Examples of the imaging device(s) 118 include at least one of an x-ray imaging device, an MRI scanner, a SPECT scanner, a PET scanner, an ultrasound imaging device, an infrared imaging device, a CT scanner, an OCT imaging device, an OCTA imaging device, or an optical camera. In various implementations, the imaging device(s) 118 include one or more sensors configured to detect signals (e.g., photons, sound waves, electric fields, magnetic fields, etc.) from the subject being imaged. For example, a PET scanner includes sensors configured to detect photons emitted by a radiotracer disposed in the body of the subject. In some cases, the imaging device(s) 118 further include one or more emitters that output and/or induce the signals detected by the sensor(s). For instance, a plain film x-ray imaging device includes emitters that emit x-rays into and/or onto the subject and sensors that detect at least some of the x-rays that are not absorbed and/or scattered by the subject. Further, the imaging device(s) 118 includes at least one analog to digital converter (ADC) that is configured to convert the signals detected by the sensor(s) into digital data. In various implementations, the imaging device(s) 118 include at least one processor configured to generate the diagnostic image 120 based on the digital data.

The diagnostic image 120 may have the same or similar format to the medical images 110. For example, the diagnostic image 120 may include the same number of channels as an example medical image 110. In various implementations, the diagnostic image 120 may be generated using the same imaging modality (or modalities) as the medical images 110. In some cases, the imaging device(s) 118 generated the medical images 110 included in the training data 108.

In various implementations, the classifier 114 accepts the diagnostic image 120 as an input. The classifier 114 generates a predicted label 122 based on the diagnostic image 120. The predicted label 122 indicates whether the diagnostic image 120 is predicted to depict the disease and/or severity level.

In addition, the BAM model 116 accepts the diagnostic image 120 as an input. The BAM model 116 generates a BAM 124 based on the diagnostic image 120. According to various examples, the BAM 124 is an image that includes the same pixel (or voxel) dimensions as the diagnostic image 120. Each pixel (or voxel) in the BAM 124 may have a value in a range of −1 to 1, for instance. In various implementations, the BAM 124 indicates the presence of one or more biomarkers indicative of the disease in the diagnostic image 120. For instance, the BAM 124 may be an image with the same pixel dimensions as the diagnostic image 120, wherein the values of the pixels of the BAM 124 indicate whether corresponding pixels of the diagnostic image 120 depict the biomarker(s). In some implementations, an absolute value of each pixel in the BAM 124 is taken, such that the BAM 124 includes pixel values in a range of 0 to a maximum (e.g., 1), wherein each pixel value is positively correlated to the probability that a corresponding area (or volume) of the diagnostic image 120 depicts at least one biomarker-of-interest. The BAM 124 may include the same number of channels as the diagnostic image 120. For example, if a biomarker is depicted in a first channel of the diagnostic image 120 corresponding to a first imaging modality, but the biomarker is not apparent in a second channel of the diagnostic image 120 corresponding to a second imaging modality, the presence of the biomarker may be indicated in a first channel of the BAM 124 and may not be indicated in a second channel of the BAM 124.

In various implementations, the prediction system 102 may output the predicted label 122 and the BAM 124 to one or more clinical devices 126. Additionally, the imaging device(s) 118 and/or the prediction system 120 may output the diagnostic image 120 to the clinical device(s) 126.

In various implementations, the clinical device(s) 126 may output the diagnostic image 120 to a user (e.g., a physician). For instance, the clinical device(s) 126 include a display configured to visually output the diagnostic image 120. In some cases, the clinical device(s) 126 further output the BAM 124 overlaid on the diagnostic image 120. For example, the BAM 124 may be a transparent image that highlights portions of the diagnostic image 120 depicting the biomarker(s).

In some implementations, the prediction system 102 may be hosted on one or more devices (e.g., servers) that are located remotely from the clinical device(s) 126. For example, the prediction system 102 may receive and evaluate diagnostic images from multiple imaging devices and/or clinical devices located in various locations (e.g., various healthcare facilities).

According to certain implementations, the prediction system 102 and/or the clinical device(s) 126 may interface with an Electronic Medical Record (EMR) system (not illustrated). The diagnostic image 120, the predicted label 122, the BAM 124, and the like, may be stored and/or accessed in memory stored at the EMR system.

In various implementations, at least one of the prediction system 102, the predictive model 106, the imaging device(s) 118, or the clinical device(s) 126 may include at least one system (e.g., a distributed server system), at least one computing device, at least one software instance (e.g., a VM) hosted on system(s) and/or device(s), or the like. For instance, instructions to execute functions associated with at least one of prediction system 102, the predictive model 106, the imaging device(s) 118, or the clinical device(s) 126 may be stored in memory. The instructions may be executed, in some cases, by at least one processor.

According to various examples, at least one of the training data 108, the diagnostic image 120, the predicted label 122, or the BAM 124, may include data packaged into at least one data packet. In some examples, the data packet(s) can be transmitted over wired and/or wireless interfaces. According to some examples, the data packet(s) can be encoded with one or more keys stored by at least one of the prediction system 102, the trainer 104, the predictive model 108, the imaging device(s) 118, or the clinical device(s) 126, which can protect the data paged into the data packet(s) from being intercepted and interpreted by unauthorized parties. For instance, the data packet(s) can be encoded to comply with Health Insurance Portability and Accountability Act (HIPAA) privacy requirements. In some cases, the data packet(s) can be encoded with error-correcting codes to prevent data loss during transmission.

In particular examples, the classifier 114 is trained to identify the presence and/or level of diabetic retinopathy (DR) present in the diagnostic image 120 (e.g., an OCTA and/or OCT image). In these examples, the BAM model 116 may generate the BAM 124 to indicate one or more non-perfusion areas in the diagnostic image 120, because non-perfusion areas are associated with a DR diagnosis. In some cases, the BAM model 116 may also indicate one or more additional areas in the diagnostic image 120 associated with biomarkers that are not known by clinicians as indications of DR, but are nevertheless consistently associated with DR. Accordingly, the BAM 124 may enable researchers to identify new biomarkers associated with DR.

According to some examples, the classifier 114 is trained to identify the presence and/or level of age-related macular degeneration (AMD) present in the diagnostic image 120 (e.g., a fundus image). In these instances, the BAM model 116 may generate the BAM 124 to indicate drusen, pigmentary abnormalities, choroidal neovascularization (CNV), any other indicator of AMD, or any combination thereof in the diagnostic image 120.

In particular cases, the classifier 114 is trained to identify the presence and/or level of a brain tumor present in the diagnostic image 120 (e.g., a structural and/or functional MRI image). In these cases, the BAM model 116 may generate the BAM 124 to indicate one or more tumor regions in the diagnostic image 120. In some examples, the tumor region(s) would not be otherwise apparent to a clinician reviewing the diagnostic image 120 without the benefit of the BAM 124.

In various instances, the classifier 114 is trained to identify the presence and/or level of breast cancer present in the diagnostic image 12 (e.g., a CT image). In these cases, the BAM model 116 may generate the BAM 124 to indicate one or more breast cancer tumor regions in the diagnostic image 120. In some cases, the tumor region(s) would not be otherwise apparent to a clinician viewing the diagnostic image 120 without the benefit of the BAM 124.

In some examples, the classifier 114 is trained to identify the presence of appendicitis in the diagnostic image 120 (e.g., an ultrasound and/or x-ray-based CT image). In these examples, the BAM model 116 may generate the BAM 124 to indicate one or more regions of appendix inflammation depicted in the diagnostic image 120.

The specific examples of diseases and biomarkers described herein are not limiting. Various implementations of the present disclosure can be used to identify various biomarkers-of-interest associated with various diseases that can be identified in medical images. In various cases, the biomarkers-of-interest are not previously known to clinicians, such that systems described herein can be used to identify new, previously unappreciated biomarkers as indicative of disease.

Figure 2:
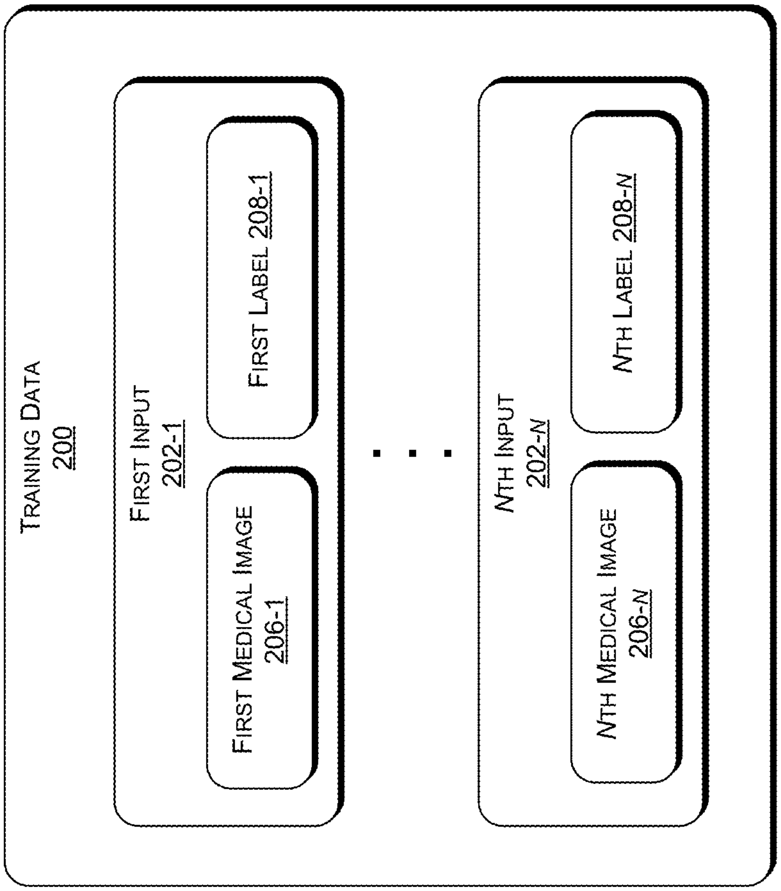
FIG. 2 illustrates an example of training data for training a biomarker activation model (BAM) model.

FIG. 2 illustrates an example of training data 200 for training a BAM model. The training data 200, for example, may be the training data 108 described above with reference to FIG. 1.

The training data 200 may include n inputs 202-1 to **202-*n*, wherein n is a positive integer. The inputs 202-1 to 202-*n* may respectively include volumetric images 206-1 to 206-*n* and gradings 208-1 to 208-*n*. Each one of the inputs 202-1 to 202-*n* may correspond to a single individual who was imaged at a particular time. For example, a first input 202-1 may include a first medical image 206-1** of a first example individual that was scanned on a first date, and a second input may include a second medical image of a second example individual that was scanned on a second date. In some cases, the first individual and the second individual can be the same person, but the first date and the second date may be different days. In some implementations, the first individual and the second individual can be different people, but the first date and the second date can be the same days.

The first to nth gradings 208-1 to **208-*n* may indicate the presence and/or level of a disease depicted in the first to nth medical images 206-1 to 206-*n*, respectively. In various cases, the first to nth labels 208-1 to 208-*n* are generated by one or more experts, such as one or more physicians with specialized training in diagnosing the disease. For instance, if the disease is diabetic retinopathy, the experts may be ophthalmologists. In some cases, the expert(s) rely on different images than the first to nth medical images 206-1 to 206-*n* in order to generate the labels 208-1 to 208-*n*. For instance, the medical images 206-1 to 206-*n* may be volumetric OCT and/or OCTA images, but the expert(s) may generate the labels 208-1 to 208-*n*** based on fundus and/or OCT projection images.

According to various implementations, the training data 200 is used to train a predictive model. In some examples, the predictive model includes at least one CNN including various parameters that are optimized based on the training data 200. For instance, the training data 200 may be used to train a CNN configured to generate BAM that indicates one or more biomarkers-of-interest that are relevant to the classification of a disease of a subject.

Figure 3:
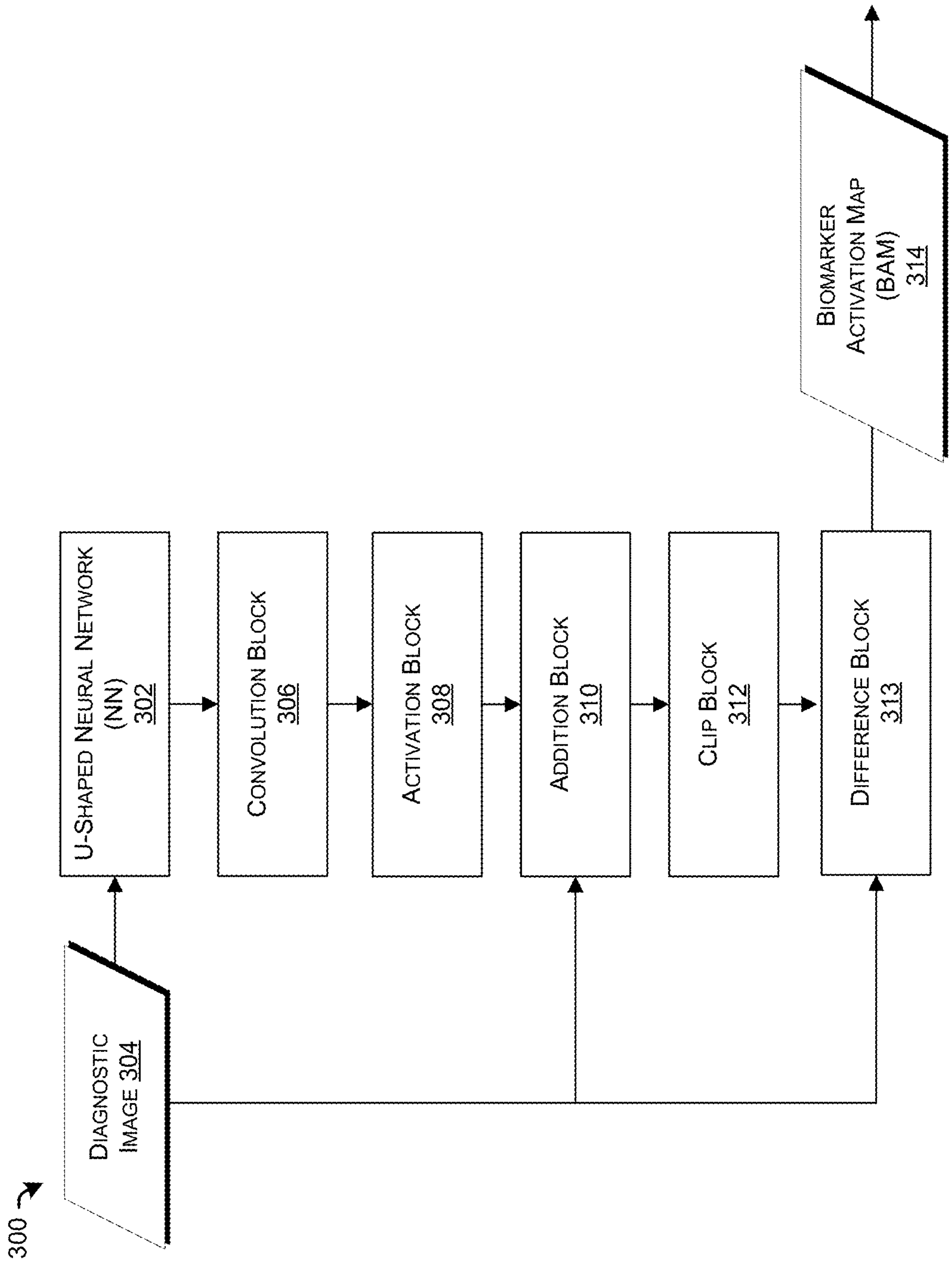
FIG. 3 illustrates an example BAM model.

FIG. 3 illustrates an example BAM model 300. The BAM model 300, for example, may be the BAM model 116 described above with reference to FIG. 1. The BAM model 300 may be executed by at least one processor, in various implementations.

In various implementations, a U-shaped NN 302 receives a diagnostic image 304 as an input. The diagnostic image 304, for example, is a medical image. In various examples, the diagnostic image 304 includes multiple channels corresponding, respectively, to different imaging modalities. The diagnostic image 304 may include at least one 2D image, at least one 3D image, or a combination thereof.

The U-shaped NN 302 is and/or includes a CNN, in various implementations. In particular implementations, the U-shaped NN 302 may include one or more U-shaped NN units, wherein a first residual block is connected to a second residual block, which is connected to a deconvolutional block. An output of the first residual block and an output of the deconvolutional block are input into a concatenation block, which produces an output of the U-shaped NN unit by concatenating the output of the first residual block and the output of the deconvolutional block. In various implementations, the residual blocks may include the performance of one or more convolution and/or cross-correlation functions. In some cases, the residual blocks further include the performance of an activation (e.g., ReLU activation) function. In various implementations, the deconvolutional block includes performance of at least one deconvolution and/or a de-cross-correlation function, a batch normalization function, an activation (e.g., ReLU activation) function, or any combination thereof.

A convolution block 306 receives the output of the U-shaped NN 302. In various implementations, the convolution block 306 includes the performance of one or more convolution and/or cross-correlation functions.

An activation block 308 receives the output of the convolution block 306. In various implementations, the activation block 308 includes the performance of an activation (e.g., Tanh activation) function.

An addition block 310 receives the output of the activation block 308 as well as the diagnostic image 304. The addition block 310 may include the performance of adding the output of the activation block 308 to the diagnostic image 304.

A clip block 312 may receive the output of the addition block 310. In various implementations, the clip block 312 may include the performance of clipping the output of the addition block 310. For example, the clip block 312 may be defined according to a minimum value and a maximum value. Any value within the output of the addition block 310 that is below the minimum value is reassigned the minimum value. Any value within the output of the addition block 310 that is above the maximum value is reassigned the maximum value.

The output of the clip block 312 is input into a difference block 313, along with the diagnostic image 304. The difference block 313 may generate a BAM 314 by generating a difference image of the output of the clip block 312 and the diagnostic image 304 (e.g., after Gaussian filtering). In various implementations, the BAM 314 is an image with the same pixel dimensions as the input image 304.

The BAM model 300 may contain various parameters that are optimized based on training data (e.g., the training data 200). For example, various convolution functions, cross-correlation functions, deconvolution functions, de-cross-correlation functions, or any combination thereof, may be defined by various parameters (e.g., filters) whose values are determined by training the BAM model 300.

Figure 4:
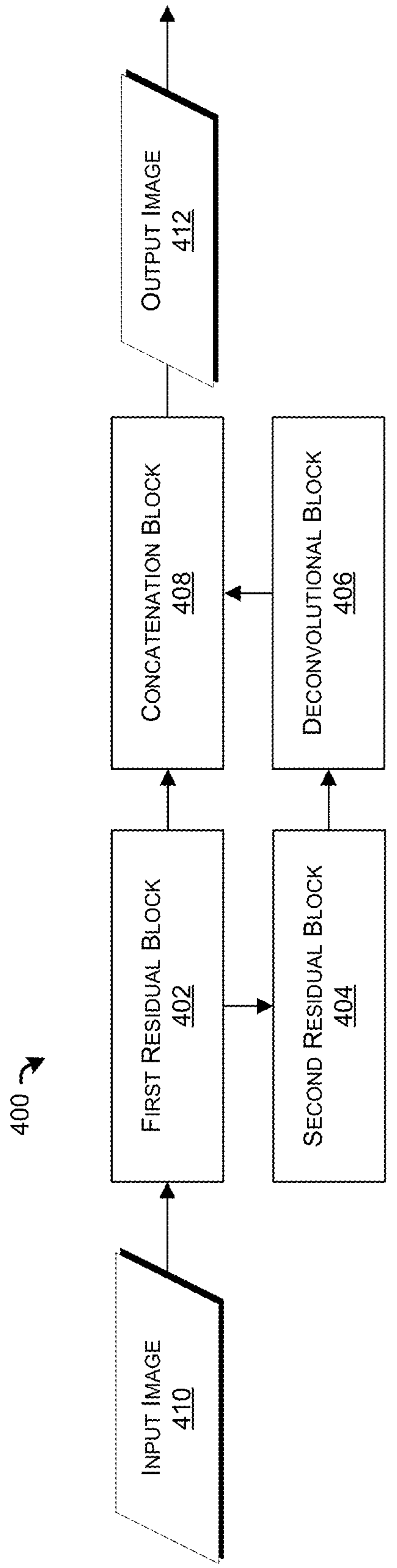
FIG. 4 illustrates an example portion of a U-shaped neural network (NN).

FIG. 4 illustrates an example portion 400 of a U-shaped NN, such as a portion of the U-shaped NN 302 described above with reference to FIG. 3. The portion 400 includes a first residual block 402, a second residual block 404, a deconvolutional block 406 and a concatenation block 408.

In various implementations, the first residual block 402 and the second residual block 404 have similar structures. Each residual block may include at least one convolution layer. For instance, an example residual block includes multiple convolution layers arranged in series. An example convolution layer includes performing a convolution and/or cross-correlation function on an image using a filter. The image, for example, is defined as an array of pixels. Similarly, the filter may be defined as an array of pixels, each pixel being defined by a particular parameter (e.g., a value). The convolution and/or cross-correlation function may defined according to a kernel size and/or a stride size. For instance, the kernel size may be 2, 3, 4, or 5 and/or the stride size may be 1, 2, 3, or 4. Some example convolution layers include performing a normalization function (e.g., a batch normalization function) after performing the convolution and/or cross-correlation function. In some cases, a convolution layer further includes performing an activation function (e.g., ReLU activation). According to various implementations, an example residual block concludes with an activation layer that includes performing an activation function.

The deconvolutional block 406 includes at least one deconvolution layer. An example deconvolution layer includes performing a deconvolution and/or inverse cross-correlation function on an image using a filter. The filter of the deconvolution layer is defined by an array of pixels. In addition, the deconvolution and/or inverse cross-correlation function is defined according to a kernel size and/or a stride size. For example, the kernel size may be 1, 2, 3, or 4 and/or the stride size may be 1, 2, 3, or 4. In some cases, the kernel size of an example deconvolution layer is smaller than the kernel size of a convolution layer in the first residual block 402 or the second residual block 404. In various implementations, the deconvolution block 406 further includes a normalization layer that includes performing a normalization function (e.g., a batch normalization function). In some cases, the deconvolution block 406 includes an activation layer that includes performing an activation function (e.g., a ReLU activation function). The concatenation block 408 includes performing a concatenation function on multiple input images.

In various implementations, the first residual block 402 receives an input image 410. An output of the first residual block 402 is input into the second residual block 404. An output of the second residual block 404 is input into the deconvolutional block. The concatenation block 408 receives two images: one is the output from the first residual block 402 and the other is the output from the deconvolutional block 406. The concatenation block 408 is used to generate an output image 412 by concatenating the two images.

According to some cases, a U-shaped NN include multiple structures that follow the general architecture of the portion 400 illustrated in FIG. 4. For example, in some examples, the second residual block 404 is the first residual block of an additional portion of the U-shaped NN, which feeds its output into another residual block that serves as the second residual block of the additional portion, as well as into a concatenation block of the additional portion. In addition, the concatenation block 408 may provide the output image 412 to a second residual block of yet another additional portion. Thus, the U-shaped NN may have an architecture that includes multiple, nested portions with the general U-shape of the portion 400 illustrated in FIG. 4.

Figure 5A:
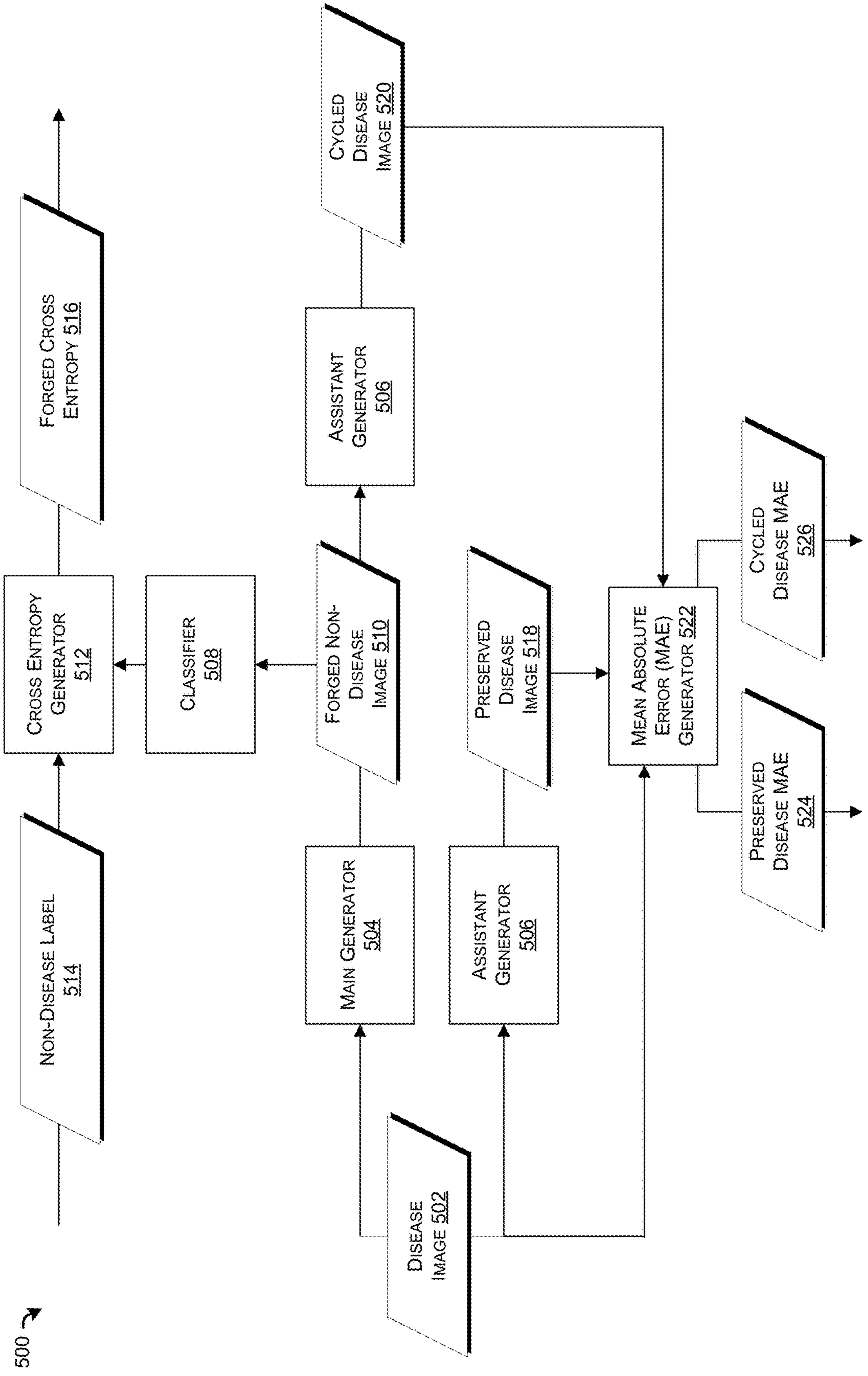
FIGS. 5A and 5B illustrate example signaling for training a BAM model. In particular.
Figure 5B:
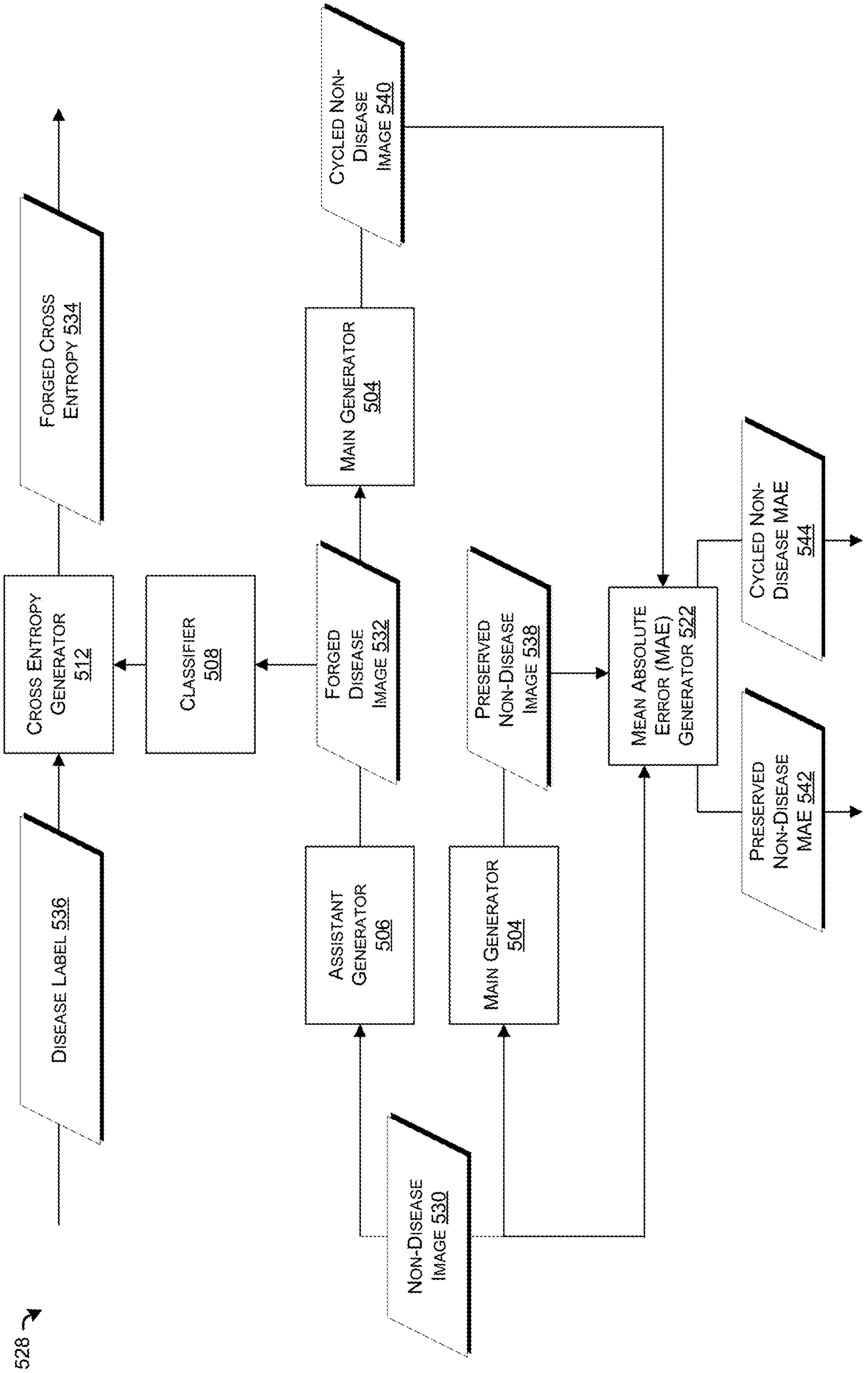

FIGS. 5A and 5B illustrate example signaling for training a BAM model, such as the BAM model 116 described above with reference to FIG. 1. In particular, FIG. 5A illustrates example signaling 500 for training a BAM model using a disease image 502. The example signaling 500 is at least partially between a main generator 504 and an assistant generator 506. The main generator 504 may include the BAM model that is to be trained. The assistant generator 506 includes the BAM model architecture, but is trained in reverse. Thus, the signaling 500 can be utilized to optimize the parameters in the main generator 504 and the assistant generator 506. An example parameter being optimized is included in both the main generator 504 and the assistant generator 506, for instance.

The signaling 500 is also between a classifier 508. The classifier 506, in various implementations, includes a machine learning model (e.g., at least one CNN) configured to detect the presence or absence of a disease in an input image (e.g., the disease image 502). For example, upon receiving an input image, the trained classifier 508 outputs an indication of whether the disease is present or absent from the input image. In some implementations, the trained classifier 508 indicates a level of disease that is present in the input image. The classifier 508 may have any of a variety of architectures suitable for disease classification. Examples of the classifier 508 include AlexNet, VGG16/19, GoogleNet, DenseNet, Inception-v3/v4, ResNet, DcardNet, Efficient-Net, SENet, Vision transformer (Vit), Data-efficient image transformer (DeiT), and other classifiers known in the art.

The disease image 502 may depict at least one physiological structure of a subject. The disease image 502 includes one or more biomarkers of interest that are indicative of the disease that is detected by the classifier 506. In various implementations, the main generator 504 generates a forged non-disease image 510 based on the disease image 502. The forged non-disease image 510 includes portions of the disease image 502 that do not include the biomarker(s) of interest. The classifier 508 receives the forged non-disease image 510 and generates an indication of whether the forged non-disease image 510 depicts the disease. That indication is further input into a cross entropy generator 512, along with a non-disease label 514. The cross entropy generator 512 generates a forged cross entropy 516 based on the output from the classifier 508 and the non-disease label 514. For example, if the forged non-disease image 510 generated by the main generator 504 is classified as non-disease (i.e., not diseased) by the classifier 508, then the output of the classifier 508 will match the non-disease label 514. However, if the forged non-disease image 510 is not classified as non-disease by the classifier 508, then various parameters in the main generator 504 may be adjusted until the classifier 508 is able to recognize the forged non-disease image 510 as non-disease. During training, the parameters of the main generator 504 are optimized in order to minimize the forged cross entropy 516.

The assistant generator 506 is also incorporated into the signaling 500 to prevent overfitting. In various implementations, the assistant generator 506 generates a preserved disease image 518 based on the disease image 502. The assistant generator 506 also generates a cycled disease image 520 based on the forged non-disease image 510. That is, the assistant generator 506 is configured to add the biomarker(s) of interest into the forged non-disease image 510 to generate the cycled disease image 520.

A mean absolute error (MAE) generator 522 is configured to generate the MAE, a mean squared error, or some other type of discrepancy, between pairs of images. For example, the MAE generator 522 generates a preserved disease MAE 524 by generating the MAE between the disease image 502 and the preserved disease image 518. In addition, the MAE generator 522 generates a cycled disease MAE 526 by generating the MAE between the cycled disease image 520 and the disease image 502. In various implementations, the parameters of the main generator 504 and the assistant generator 506 are optimized in order to minimize the preserved disease MAE 524 and the cycled disease MAE 526.

In various implementations, the parameters of the main generator 504 and assistant generator 506 are optimized in order to minimize the forged cross entropy 516, the preserved disease MAE 524, and the cycled disease MAE 526. The signaling 500 illustrated in FIG. 5A may be repeated for various disease images in training data, in order to train the BAM model represented by the main generator 504.

FIG. 5B illustrates example signaling 528 for training a BAM model using a non-disease image 530. For example, the non-disease image 530 is a training image depicting a subject that the trained classifier 508 has classified as not having the disease. The same main generator 504, assistant generator 506, and classifier 508 are utilized in the signaling 528 as the signaling 500.

The non-disease image 530 is input into the assistant generator 506. The assistant generator 506 outputs a forged disease image 532 based on the non-disease image 530. If correctly trained, the forged disease image 532 includes one or more biomarkers that will cause the classifier 508 to classify the forged disease image 532 as depicting a disease. In various cases, the trained classifier 508 generates a classification of the forged disease image 532 and inputs the classification into the cross entropy generator 512. The classification indicates whether the classifier 508 recognizes the forged disease image 532 as a disease image. The cross entropy generator 512 generates a forged cross entropy 534 by comparing the classification generated by the classifier 508 to a disease label 536.

In addition, the main generator 504 generates a preserved non-disease image 538 based on the non-disease image 530. In addition, the main generator 504 generates a cycled non-disease image 540 based on the forged disease image 532. If successfully trained, the preserved non-disease image 538 and the cycled non-disease image 540 are minimally divergent from the original non-disease image 530. The MAE generator 522 generates a preserved non-disease MAE 542 by comparing the preserved non-disease image 538 and the non-disease image 530. The In addition, the MAE generator 522 generates a cycled non-disease MAE 544 by comparing the cycled non-disease image 540 and the non-disease image 530.

In various implementations, the parameters of the main generator and assistant generator 506 are optimized in order to minimize the forged cross entropy 534, the preserved non-disease MAE 542, and the cycled non-disease MAE 544. The signaling 528 illustrated in FIG. 5B may be repeated for various non-disease images in training data, in order to train the BAM model represented by the main generator 504.

Figure 6:
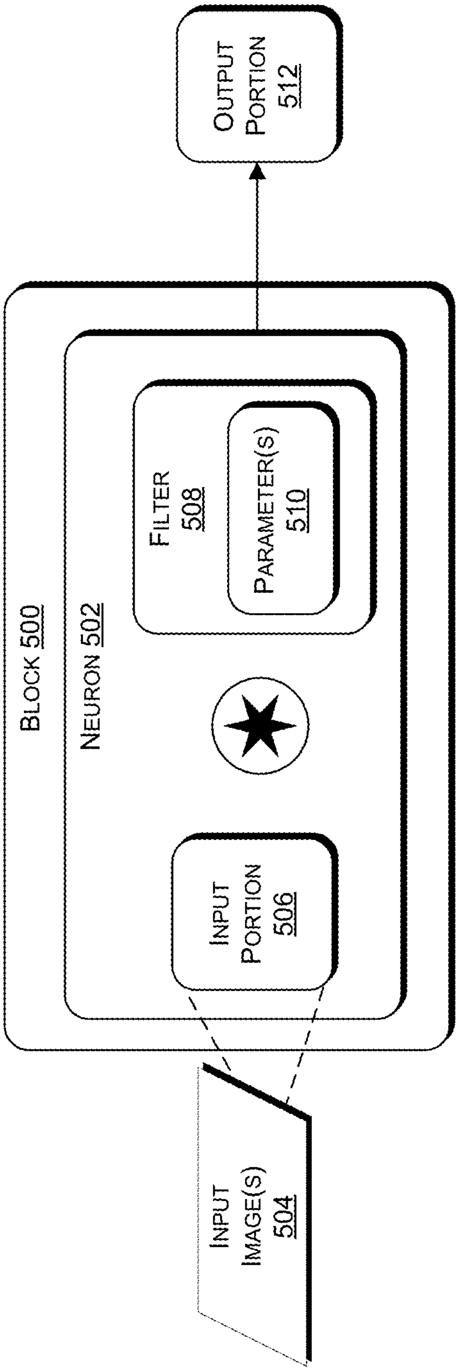
FIG. 6 illustrates an example of a convolutional block in a neural network.

FIG. 6 illustrates an example of a convolutional block 600 in a neural network. In some examples, the block 600 can represent any of the convolutional blocks and/or layers described herein.

The convolutional block 600 may include multiple neurons, such as neuron 602. In some cases, the number of neurons may correspond to the number of pixels in at least one input image 604 input into the block 600. Although one neuron is illustrated in each of FIG. 6, in various implementations, block 600 can include multiple rows and columns of neurons.

In particular examples, the number of neurons in the block 600 may be less than or equal to the number of pixels in the input image(s) 604. In some cases, the number of neurons in the block 600 may correspond to a "stride" (also referred to as a "step size") of neurons in the block 600. In some examples in which first and second neurons are neighbors in the block 600, the stride may refer to a lateral difference in an input of the first neuron and an input of the second neuron. For example, a stride of one pixel may indicate that the lateral difference, in the input image(s) 604, of the input of the first neuron and the input of the second neuron is one pixel.

Neuron 602 may accept an input portion 606. The input portion 606 may include one or more pixels in the input image(s) 604. A size of the input portion 606 may correspond to a receptive field of the neuron 602. For example, if the receptive field of the neuron 602 is a 3×3 pixel area, the input portion 606 may include at least one pixel in a 3×3 pixel area of the input image(s) 604. The number of pixels in the receptive field that are included in the input portion 606 may depend on a dilation rate of the neuron 602.

In various implementations, the neuron 602 may convolve (or cross-correlate) the input portion 606 with a filter 608. The filter may correspond to at least one parameter 610, which may represent various optimized numbers and/or values associated with the neuron 602. In some examples, the parameter(s) 610 are set during training of a neural network including the block 600.

The result of the convolution (or cross-correlation) performed by the neuron 602 may be output as an output portion 612. In some cases, the output portion 612 of the neuron 602 is further combined with outputs of other neurons in the block 600. The combination of the outputs may, in some cases, correspond to an output of the block 600. Although FIG. 6 depicts a single neuron 602, in various examples described herein, the block 600 may include a plurality of neurons performing operations similar to the neuron 602. In addition, although the convolutional block 600 in FIG. 6 is depicted in two dimensions, in various implementations described herein, the convolutional block 600 may operate in three dimensions.

Figure 7A:
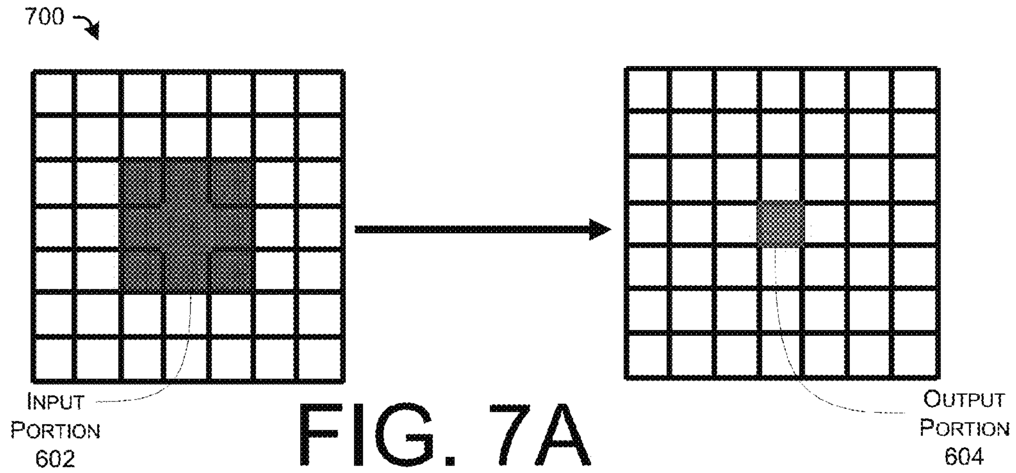
FIGS. 7A to 7C illustrate examples of dilation rates.
Figure 7B:
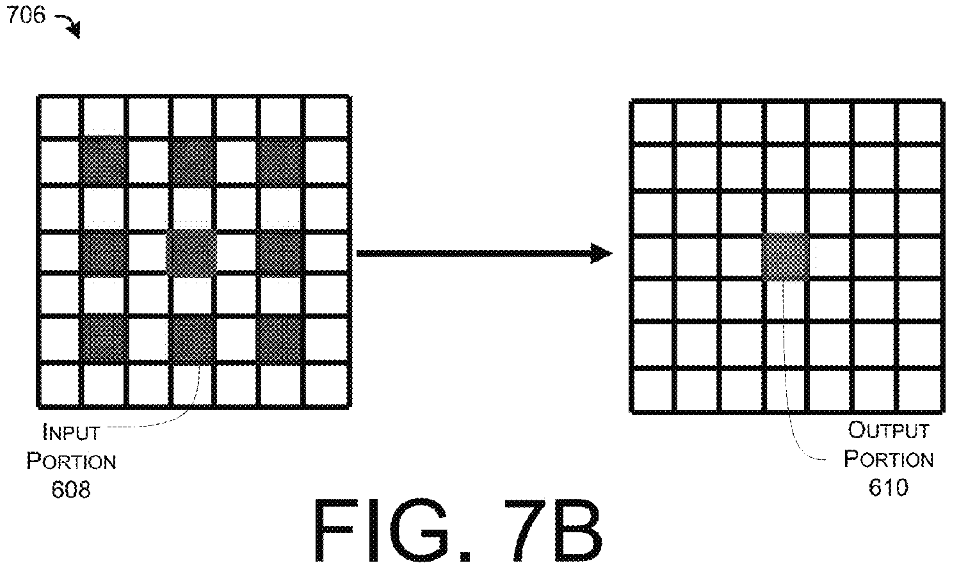
Figure 7C:
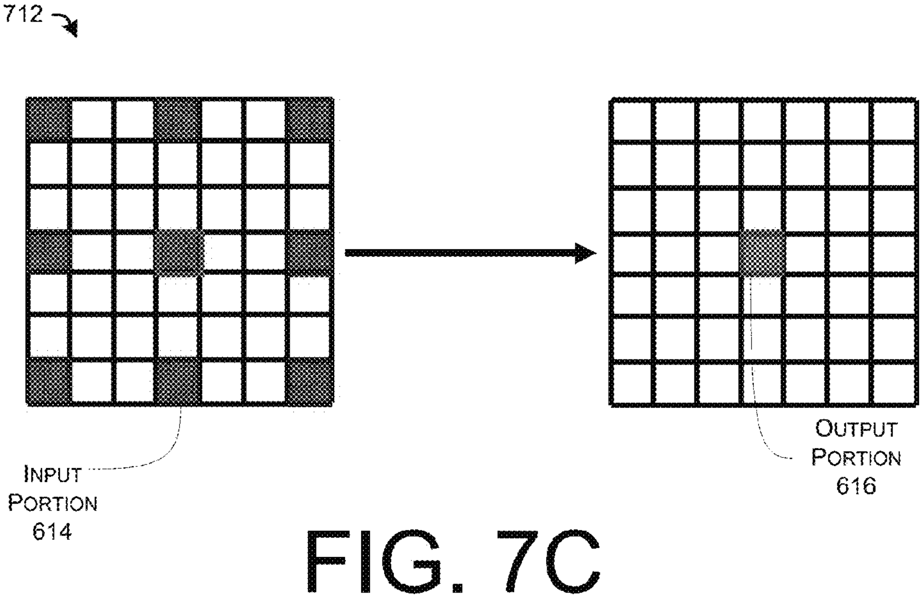

FIGS. 7A to 7C illustrate examples of dilation rates. In various implementations, the dilation rates illustrated in FIGS. 7A to 7C can be utilized by a neuron, such as the neuron 602 illustrated in FIG. 6. Although FIGS. 7A to 7C illustrate 2D dilation rates (with 3×3 input pixels and 1×1 output pixel), implementations can apply 3D dilation rates (with 3×3×3 input pixels and 1×1 output pixel).

FIG. 7A illustrates a transformation 600 of a 3×3 pixel input portion 702 into a 1×1 pixel output portion 704. The dilation rate of the transformation 700 is equal to 1. The receptive field of a neuron utilizing the transformation 700 is a 3×3 pixel area.

FIG. 7B illustrates a transformation 706 of a 3×3 pixel input portion 7608 into a 1×1 pixel output portion 610. The dilation rate of the transformation 706 is equal to 2. The receptive field of a neuron utilizing the transformation 706 is a 5×5 pixel area.

FIG. 7C illustrates a transformation 712 of a 3×3 pixel input portion 714 into a 1×1 pixel output portion 716. The dilation rate of the transformation 712 is equal to 4. The receptive field of a neuron utilizing the transformation 700 is a 9×9 pixel area.

Figure 8:
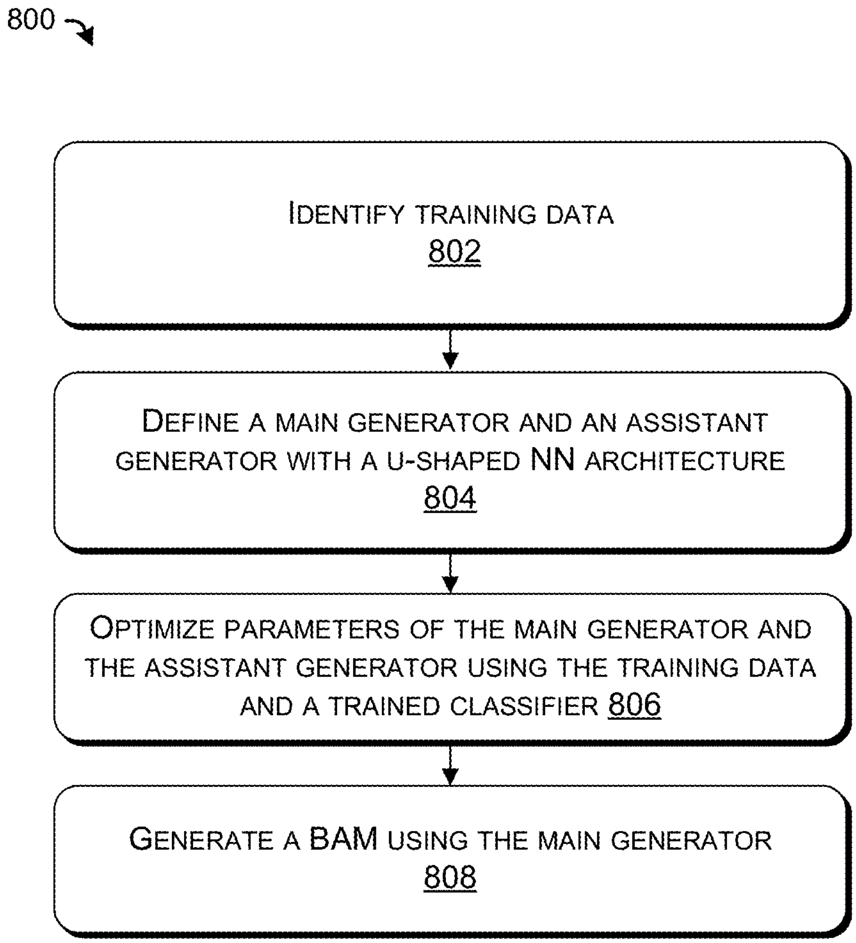
FIG. 8 illustrates an example process for training a BAM model.

FIG. 8 illustrates an example process 800 for training a BAM model. The process 800 can be performed by an entity, such as at least one of the prediction system 102, the trainer 104, or one or more processors.

At 802, the entity identifies training data. The training data may include medical images of multiple individuals in a population. In various examples, the medical images depict the same type of physiological structure. For example, the medical images may depict the retinas of the individuals. In various cases, the training data further includes labels indicating the presence or absence of a disease in the individuals. In some cases, the training data includes the levels of disease experienced by the individuals.

At 804, the entity defines a main generator and an assistant generator with a u-shaped NN architecture. In various implementations, the main generator and the assistant generator have the same architecture. The main generator and the assistant generator may be further defined according to various parameters.

At 806, the entity optimizes the parameters of the main generator and the assistant generator using the training data and a trained classifier. For instance, the trained classifier may include a machine learning model (e.g., a NN) configured to identify the presence and/or level of disease depicted in the medical images. The main generator and the assistant generator may be used to generate modified medical images (e.g., forged, cycled, and preserved medical images) based on the medical images in the training data. In various implementations, the parameters of the main generator and assistant generator are optimized until the trained classifier accurately classifies modified medical images.

At 808, the entity generates a BAM using the main generator. In various implementations, the entity inputs a diagnostic image into the main generator after the main generator has been trained. The main generator outputs the BAM based on the diagnostic image. In various implementations, the BAM indicates and/or highlights one or more biomarkers present in the diagnostic image that are relevant to the disease identified by the trained classifier. In various implementations, the trained classifier is also used to identify the presence and/or level of the disease in the diagnostic image.

Figure 9:
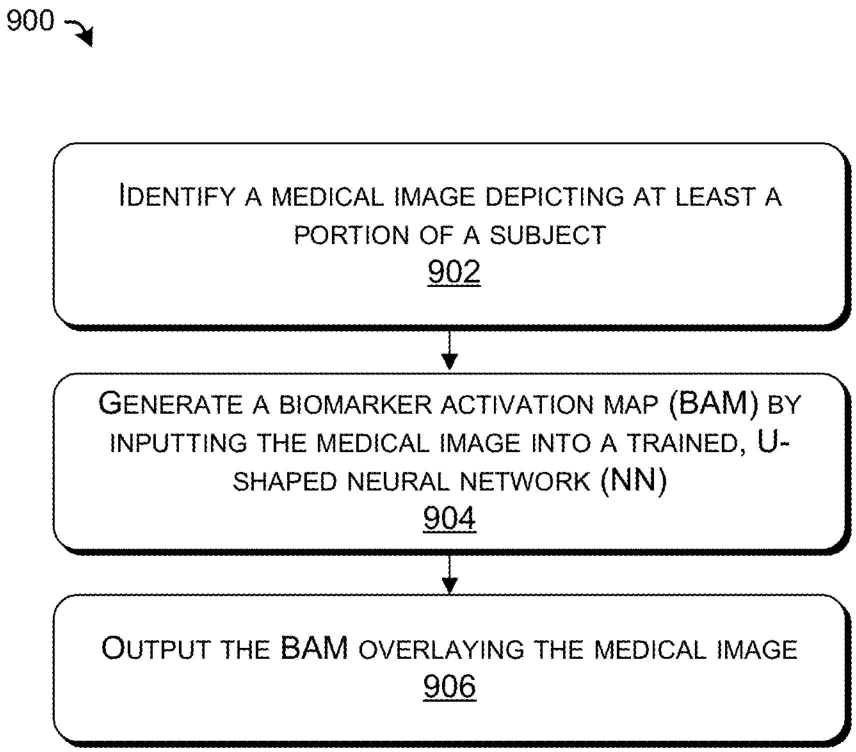
FIG. 9 illustrates an example process for generating a BAM using a trained BAM model.

FIG. 9 illustrates an example process 900 for generating a BAM using a trained BAM model. The process 900 can be performed by an entity, such as at least one of the prediction system 102, the BAM model 116, the classifier 114, or one or more processors.

At 902, the entity identifies a medical image depicting at least a portion of a subject. The medical image, for example, includes at least one of an x-ray image, a magnetic resonance imaging (MRI) image, a functional MRI (fMRI) image, a single-photon emission computerized tomography (SPECT) image, a positron emission tomography (PET) image, an ultrasound image, an infrared image, a computed tomography (CT) image, an optical coherence tomography (OCT) image, an OCT angiography (OCTA) image, a color fundus photograph (CFP) image, a fluorescein angiography (FA) image, or an ultra-widefield retinal image. The medical image depicts at least one physiological structure of the subject. In various implementations, the medical image includes multiple channels respectively depicting the physiological structure(s) captured using different imaging modalities. The medical image may include at least one 2D image, at least one 3D image, or a combination thereof.

At 904, the entity generates a BAM by inputting the medical image into a trained, U-shaped NN. In various implementations, the trained U-shaped NN includes a CNN that has multiple residual blocks, multiple deconvolutional blocks, and multiple concatenation blocks. In various implementations, the BAM indicates one or more biomarkers in the medical image that are indicative of a particular disease. According to various implementations, the U-shaped NN is trained based on a classifier (e.g., another machine learning model) configured to detect the presence and/or level of the disease in the medical image.

At 906, the entity outputs the BAM overlaying the medical image. For example, the BAM may be a transparent layer output over the medical image. In various implementations, the entity causes a display to visually present the BAM overlaying the medical image to a user.

Figure 10:
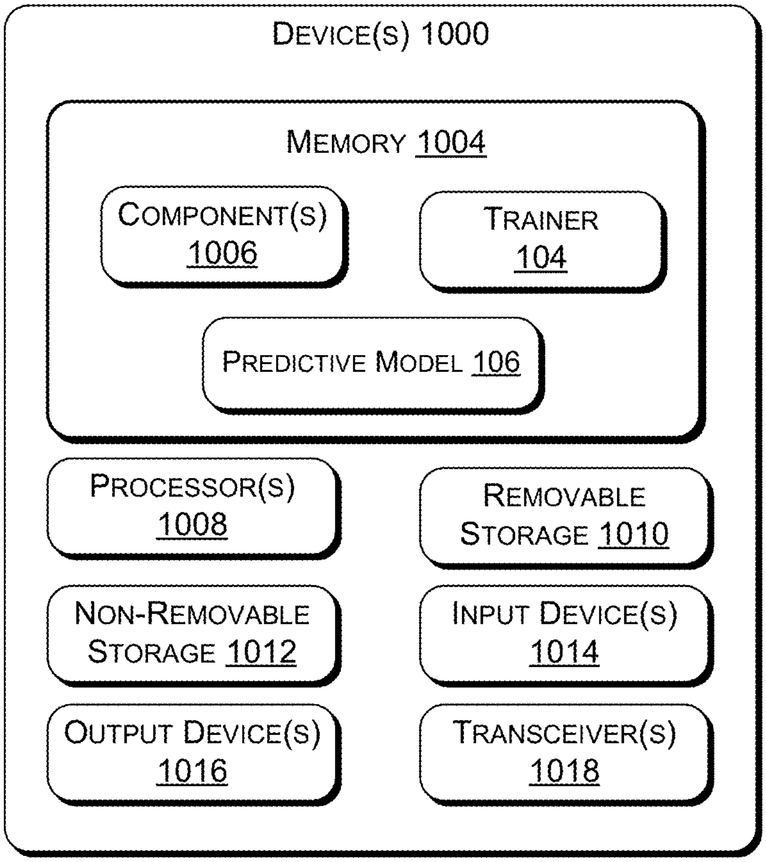
FIG. 10 illustrates an example of one or more devices that can be used to implement any of the functionality described herein.

FIG. 10 illustrates an example of one or more devices 1000 that can be used to implement any of the functionality described herein. In some implementations, some or all of the functionality discussed in connection with any of the other figures described herein can be implemented in the device(s) 1000. Further, the device(s) 1000 can be implemented as one or more server computers, a network element on a dedicated hardware, as a software instance running on a dedicated hardware, or as a virtualized function instantiated on an appropriate platform, such as a cloud infrastructure, and the like. It is to be understood in the context of this disclosure that the device(s) 1000 can be implemented as a single device or as a plurality of devices with components and data distributed among them.

As illustrated, the device(s) 1000 include a memory 1004. In various embodiments, the memory 1004 is volatile (such as RAM), non-volatile (such as ROM, flash memory, etc.) or some combination of the two.

The memory 1004 may store, or otherwise include, various components 1006. In some cases, the components 1006 can include objects, modules, and/or instructions to perform various functions disclosed herein. The components 1006 can include methods, threads, processes, applications, or any other sort of executable instructions. The components 1006 can include files and databases. For instance, the memory 1004 may store instructions for performing operations of any of the trainer 104 and/or the predictive model 106.

In some implementations, at least some of the components 1006 can be executed by processor(s) 1008 to perform operations. In some embodiments, the processor(s) 1008 includes a Central Processing Unit (CPU), a Graphics Processing Unit (GPU), or both CPU and GPU, or other processing unit or component known in the art.

The device(s) 1000 can also include additional data storage devices (removable and/or non-removable) such as, for example, magnetic disks, optical disks, or tape. Such additional storage is illustrated in FIG. 10 by removable storage 1010 and non-removable storage 1012. Tangible computer-readable media can include volatile and nonvolatile, removable and non-removable media implemented in any method or technology for storage of information, such as computer readable instructions, data structures, program modules, or other data. The memory 1004, removable storage 1010, and non-removable storage 1012 are all examples of computer-readable storage media. Computer-readable storage media include RAM, ROM, EEPROM, flash memory or other memory technology, CD-ROM, Digital Versatile Discs (DVDs), Content-Addressable Memory (CAM), or other optical storage, magnetic cassettes, magnetic tape, magnetic disk storage or other magnetic storage devices, or any other medium which can be used to store the desired information and which can be accessed by the device(s) 1000. Any such tangible computer-readable media can be part of the device(s) 1000.

The device(s) 1000 also can include input device(s) 1014, such as a keypad, a cursor control, a touch-sensitive display, voice input device, etc., and output device(s) 1016 such as a display, speakers, printers, etc. In some implementations, the input device(s) 1014, in some cases, may include a device configured to capture medical images (e.g., an OCT scanner, an OCTA scanner, an MRI scanner, an x-ray device, a CT scanner, a PET scanner, a SPECT scanner, an optical camera, etc.). In certain examples, the output device(s) 1016 can include a display (e.g., a screen, a hologram display, etc.) that can display a medical image of a subject overlaid with a BAM indicating one or more biomarkers indicative of a disease experienced by the subject.

As illustrated in FIG. 10, the device(s) 1000 can also include one or more wired or wireless transceiver(s) 1016. For example, the transceiver(s) 1016 can include a Network Interface Card (NIC), a network adapter, a Local Area Network (LAN) adapter, or a physical, virtual, or logical address to connect to the various base stations or networks contemplated herein, for example, or the various user devices and servers. The transceiver(s) 1016 can include any sort of wireless transceivers capable of engaging in wireless, Radio Frequency (RF) communication. The transceiver(s) 1016 can also include other wireless modems, such as a modem for engaging in Wi-Fi, WIMAX, Bluetooth, or infrared communication.

First Example

Generative-Adversarial-Learning-Based Biomarker Activation Map for Improving the Interpretability of Deep-Learning-Aided Diabetic Retinopathy Screening Deep learning models provide an accurate means of automatically diagnosing diseases from medical images. The power of these models is attributable in part to the inclusion of hidden layers that render algorithm outputs difficult to interpret even as they improve performance. This example provides a novel biomarker activation map (BAM) framework based on generative adversarial learning (GAL) that allows graders and clinicians to verify diagnostic deep learning algorithms' decision making. The proposed BAM framework was evaluated using a deep-learning-based classifier for optical coherence tomography (OCT) and its angiography OCTA that diagnoses referable diabetic retinopathy (DR). The classifier was trained, validated, and evaluated using 456 macular scans. Scans were classified as non-referable or referable DR by masked retina specialists based on current clinical standards. The BAM generation framework uses two generators with U-shaped architectures. The framework was trained, validated, and evaluated based on the same data set of the classifier. The main generator was trained to take scans from referable cases as input and produce an output that would be classified by the classifier as non-referable. To make sure only the classifier-selected biomarkers are highlighted in the BAM, an assistant generator was trained to do the opposite, producing from non-referable or healthy scans data that would be classified as referable by the classifier. The BAM is constructed as the difference image between the output and input of the main generator. The generated BAMs explicitly highlighted known pathologic features including nonperfusion area and retinal fluid. In addition, the BAM did not highlight normal tissue. The BAMs generated by the GAL method could provide sufficient interpretability to help clinicians utilize deep-learning-aided disease classification systems. The BAM framework could also facilitate the identification of biomarkers in medical images.

Introduction

Deep learning techniques are widely used because they achieve state-of-the-art performance for automated disease classification in several imaging modalities (Y. LeCun et al., *Nature, vol.* 521, no. 7553, pp. 436-44, May 2015; G. Litjens et al., *Medical image analysis*, vol. 42, pp. 60-88, December 2017; D. Shen et al., *Annual review of biomedical engineering*, vol. 19, pp. 221-248 June 2017; S. Suganyadevi et al., *International Journal of Multimedia Information Retrieval*, vol. 11, no. 1, pp. 19-38, 2022; T. T. Hormel et al., *Progress in retinal and eye research*, vol. 85, pp. 100965, November 2021). However, this excellent performance comes at the cost of sometimes inscrutable outputs. The presence of hidden layers in network architectures renders a straightforward account of the classifier's action on inputs inaccessible, and consequently deep learning classifier outputs are difficult to verify. In the absence of heuristic devices deep-learning-aided diagnosis cannot be confirmed outside of manual grading, which largely defeats the purpose of automation. The issues caused by the poor interpretability have become a major hurdle for translating deep-learning-aided classification systems into the clinic (J. He et al., *Nature medicine*, vol. 25, no. 1, pp. 30-36, January 2019; S. Gerke S et al., *Artificial intelligence in healthcare, Academic Press*, pp. 295-36, 2020; Z. Salahuddin et al., *Computers in biology and medicine*, vol. 140, pp. 105111, 2022). The most prevalent deep learning classifier interpretability heuristics are attention maps. These visualizations indicate the relative importance of regions of an image for classifier decision making and indicate which features were useful for the classification task. Originally developed for non-medical image recognition tasks (e.g., dog vs. cat classification shown in FIG. 11) (Q. Zhang and S. C. Zhu, *Frontiers of Information Technology & Electronic Engineering*, vol. 19, no. 1, pp. 27-39, January 2018; D. V. Carvalho et al., *Electronics*, vol. 8, no. 8, pp. 832, July 2019; P. Linardatos et al., *Entropy*, vol. 23, no. 1, pp. 18, December 2020), attention maps have also been applied in medical image analysis for several disease classification tasks (Z. Salahuddin et al., *Computers in biology and medicine*, vol. 140, pp. 105111, 2022). However, medical image classification is distinct from non-medical image classification in several regards. In non-medical image classification, classes are typically identified by unique features which are in general not shared between the separate classes.

This is not true in medical image diagnosis. In medical image diagnosis, different classes share at least some (e.g., most) features. Instead of containing unique features, healthy and less severe instances of a disease merely lack features exhibited in more advanced cases. The identification of a normal (e.g., non-disease) or lower severity classes should therefore be based on the absence, rather than presence, of specific features. Additionally, non-medical image classification operates on color or grayscale images, in which input channels are highly correlated. In medical imaging algorithms may instead rely on multiple imaging modalities to produce a diagnosis. Different modalities may image anatomy at different resolutions, or may visualize separate features (e.g., vascular vs. structural anatomy). In such cases it may not be straightforward to interpret existing attention map frameworks.

In order to provide sufficient interpretability fora deep learning classifier, a novel biomarker activation map (BAM) generation framework is proposed in this study. The BAM generation framework was designed based on generative adversarial learning (I. Goodfellow et al., *Advances in neural information processing systems*, vol. 27, 2014; Mirza and Osindero, "Conditional generative adversarial nets," *arXiv preprint arXiv:*1411.1784, 2014; P. Isola et al. in *Proc. IEEE conference on computer vision and pattern recognition,* 2017, pp. 1125-34; J. Y. Zhu et al. in *Proc. of the IEEE international conference on computer vision.* 2017, pp. 2223-32). The proposed framework was evaluated on a referable diabetic retinopathy (DR) classifier based on optical coherence tomography (OCT) and OCT angiography (OCTA) imaging.

Related Work

Attention heatmaps are tools for interpreting deep-learning-aided classifiers outputs. Among this family of methods, the gradient-based, class activation map (CAM)-based, and propagation-based methods are the most important techniques.

In the gradient-based methods, the heatmap is generated based on the gradients of different convolutional layers with respect to the input (M. Sundararajan et al. in *Proc. of the 34th International Conference on Machine Learning,* 2017, pp. 3319-28; A. Shrikumar et al., "Not just a black box: Learning important features through propagating activation differences," *arXiv preprint arXiv:*1605.01713, 2016; D. Smilkov et al., "Smoothgrad: removing noise by adding noise," *arXiv preprint arXiv:*1706.03825, 2017; Srinivas, and Fleuret in *Advances in Neural Information Processing Systems,* 2019, pp. 4126-35). In practice the outputs from these gradient-based methods are class-agnostic, which means the generated heatmaps are similar between different classes (H. Chefer et al. in *Proc. of the IEEE/CVF Conference on Computer Vision and Pattern Recognition.* 2021, pp. 782-91).

However, in medical imaging features in healthy images are shared with images also exhibiting pathology, so a gradient-based method cannot meaningfully indicate important regions for classifying healthy or less severe disease. In addition, only a single-channel heatmap can be generated from the gradient gradient-based methods, so these methods are also unsuitable for disease classifiers which may use multiple imaging modalities as inputs.

The CAM-based methods are class-specific and have been widely used in studies of deep learning disease classifiers (B. Zhou et al. in *Proc. of the IEEE Computer Society Conference on Computer Vision and Pattern Recognition,* 2016, pp. 2921-29; R. R. Selvaraju et al. in *Proc. of the IEEE International Conference on Computer Vision,* 2017, pp. 618-26; A. Chattopadhay et al. in *Proc.*—2018 *IEEE Winter Conference on Applications of Computer Vision,* 2018, pp. 839-47; K. Li et al. in *Proc. of the IEEE Computer Society Conference on Computer Vision and Pattern Recognition,* 2018, pp. 9215-23). The basic CAM method combines the class-specific weight and the output of the last convolutional layer before global average pooling to produce the attention map (B. Zhou et al. in *Proc. of the IEEE Computer Society Conference on Computer Vision and Pattern Recognition,* 2016, pp. 2921-29). However, the CAM-based methods only use the highest convolutional layer, which generates low-resolution heatmaps (H. Chefer et al. in *Proc. of the IEEE/CVF Conference on Computer Vision and Pattern Recognition.* 2021, pp. 782-91).

Furthermore, as with the gradient-based methods, CAM-based methods can only generate one-channel heatmaps. Propagation-based methods (see, e.g., H. Chefer et al. in *Proc. of the IEEE/CVF Conference on Computer Vision and Pattern Recognition.* 2021, pp. 782-91; [33] G. Montavon et al., *Pattern Recognition*, vol. 65, pp. 211-22, May 2017; S. Bach et al., *PloS one*, vol. 10, no. 7, pp. e0130140, July 2015; W. Nam et al., "Relative attributing propagation: Interpreting the comparative contributions of individual units in deep neural networks," *arXiv preprint arXiv:* 1904.00605, 2019; S. Gur et al. in *Proc. AAAI,* 2021, pp. 11545-54; A. Shrikumar et al. in *Proc. of the* $34^{th}$ *International Conference on Machine Learning—Volume* 70, 2017, pp. 3145-53; Lundberg and Lee in *Advances in Neural information Processing Systems,* 2017, pp. 4765-74; J. Gu et al. in *Asian Conference on Computer Vision,* 2018, pp. 119-34; B. K. Iwana et al., "Explaining convolutional neural networks using softmax gradient layer-wise relevance propagation," *arXiv preprint arXiv:*1908.04351, 2019) mostly rely on the Deep Taylor Decomposition (DTD)

framework (G. Montavon et al., *Pattern Recognition*, vol. 65, pp. 211-22, May 2017). Some of these methods are class-agnostic in practical applications (H. Chefer et al. in *Proc. of the IEEE/CVF Conference on Computer Vision and Pattern Recognition.* 2021, pp. 782-91).

To solve this issue, the class-specific propagation-based methods were proposed (J. Gu et al. in *Asian Conference on Computer Vision,* 2018, pp. 119-34; B. K. Iwana et al., "Explaining convolutional neural networks using softmax gradient layer-wise relevance propagation," *arXiv preprint arXiv:*1908.04351, 2019). Compared to Grad-CAMs, the attention maps generated by these class-specific LRP methods have higher resolution (B. K. Iwana et al., "Explaining convolutional neural networks using softmax gradient layer-wise relevance propagation," *arXiv preprint arXiv:* 1908.04351, 2019).

Several methods which do not belong to these three major categories have also been proposed to interpret deep learning classifiers. These include input-modification-based methods (B. Alipanahi et al., *Nature Biotechnology*, vol. 33, no. 8, pp. 831-38, July 2015; Zeiler and Fergus in *European Conference on Computer Vision,* 2014, pp. 818-33; B. Zhou et al., "Object detectors emerge in deep scene cnns," *arXiv preprint arXiv:*1412.6856, 2014; Zhou and Troyanskaya, *Nature Methods*, vol. 12, no. 10, pp. 931-34, August 2015; Mahendran and Vedaldi, *International Journal of Computer Vision*, vol. 120, no. 3, pp. 233-55, May 2016; C. Olah et al., *Distill*, vol. 2, no. 11, pp. e7, November 2017), saliency-based methods (Dabkowski and Gal in *Advances in Neural Information Processing Systems*, pp. 6970-79, 2017; K. Simonyan et al., "Deep inside convolutional networks: Visualising image classification models and saliency maps," *arXiv preprint arXiv:*1312.6034, 2013; B. Mittelstadt et al. in *Proc. of the conference on fairness, accountability, and transparency*, pp. 279-288, 2019; B. Zhou et al., *IEEE transactions on pattern analysis and machine intelligence*, vol. 41, no. 9, pp. 2131-45, July 2018), an activation maximization method (D. Erhan et al., *University of Montreal*, vol. 1341, no. 3, pp. 1, January 2009), an excitation backprop method (J. Zhang et al., *International Journal of Computer Vision*, vol. 126, no. 10, pp. 1084-02, 2018), and perturbation methods (R. Fong et al. in *Proc. of the IEEE International Conference on Computer Vision*, pp. 2950-58, 2019; Fong and Vedaldi in *Proc. of the IEEE International Conference on Computer Vision*, pp. 3429-37, 2017). These methods do not in general achieve the accuracy of gradient-, CAM-, or propagation-based methods (H. Chefer et al. in *Proc. of the IEEE/CVF Conference on Computer Vision and Pattern Recognition.* 2021, pp. 782-91). In addition, most of these methods are also limited to generating a single attention map per output, in which the contribution between different image modalities cannot be compared.

MATERIALS

Methods

A. Training

Figure 13A:
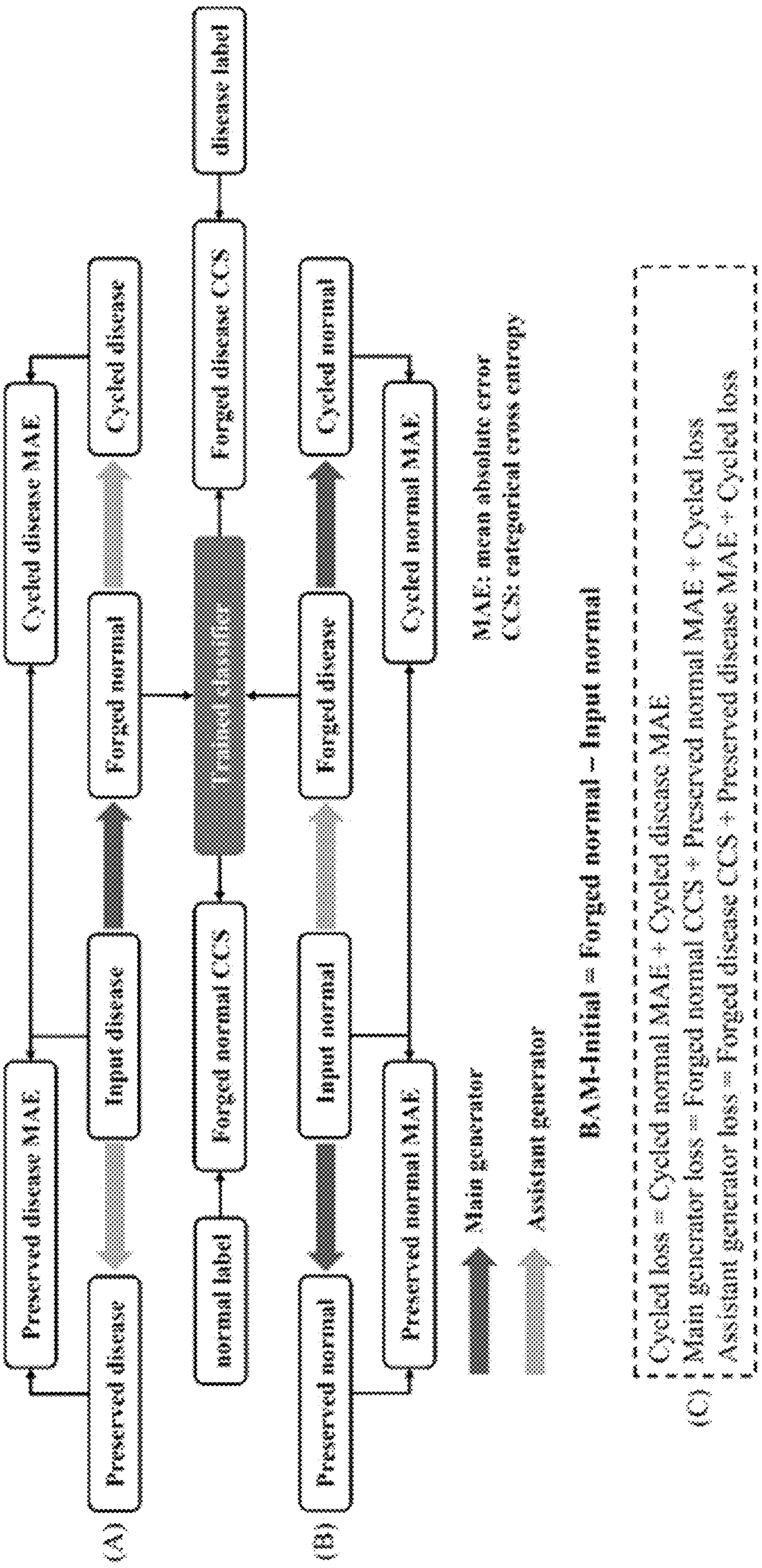
FIG. 13A Illustrates an example BAM generation framework architecture and training process.
Figure 13B:
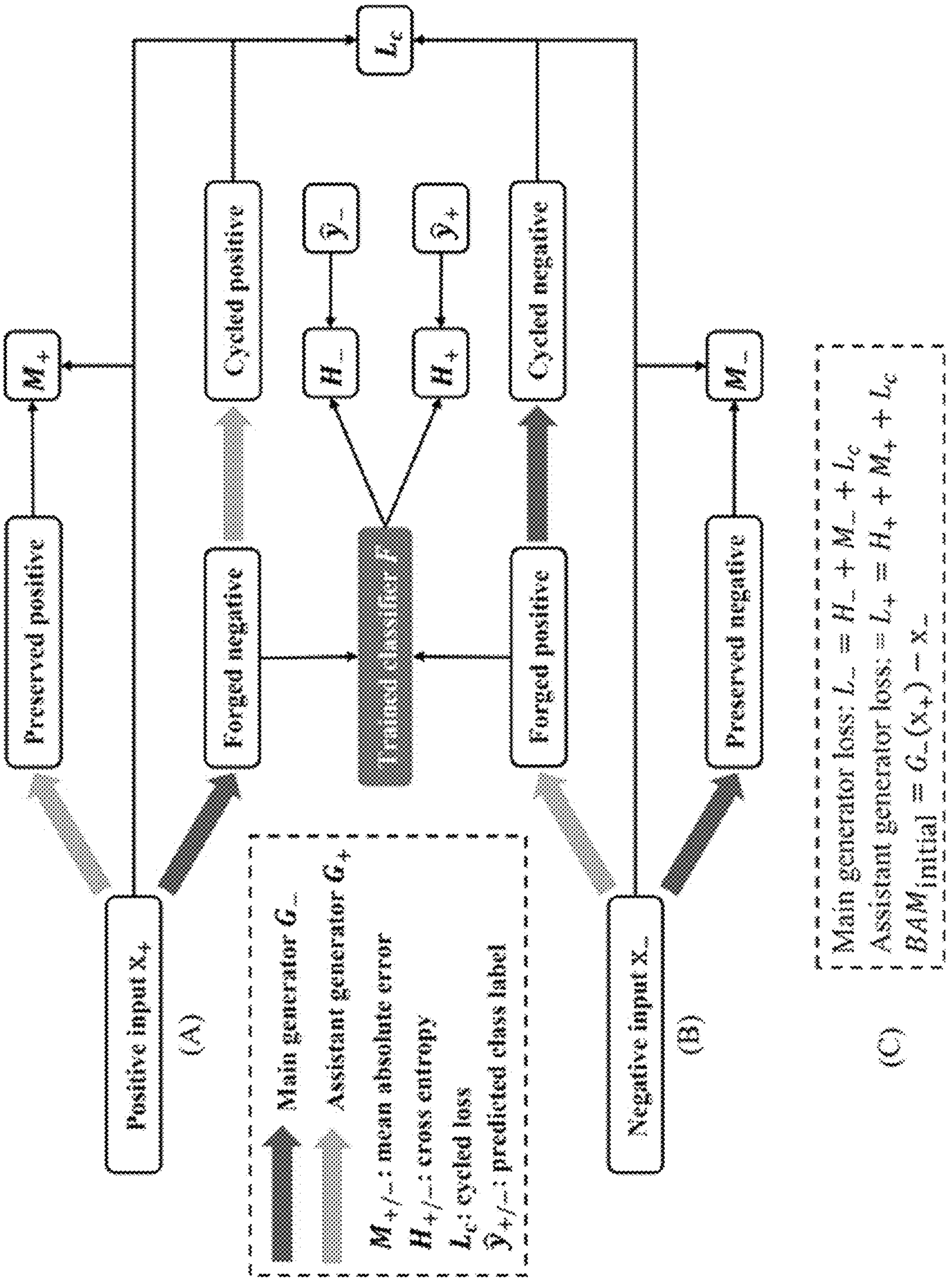
FIG. 13B illustrates an example BAM generation framework architecture and training process.

FIG. 13B illustrates an example BAM generation framework architecture and training process. Two generators were trained to produce the BAM (A) Positive class inputs are acted on by the main and assistant generators (blue and green arrows, respectively). The main generator was trained to produce output images that would be classified as the negative class by the classifier. The assistant generator performs the inverse task, producing outputs that the classifier would still diagnose as the positive class. (B) Training from negative inputs is symmetric, with the labels switching roles. (C) Training of the main and assistant generators occurred simultaneously. This scheme prevents the main generator from overfitting the negative class inputs by producing unnecessary changes to the inputs.

A classifier F trained to predict positive and negative class labels $\hat{y}$ from input data x according to $\hat{y}=F(x)$. The positive class $y_+$ could indicate the presence of a specific pathology, disease, or disease severity, with the negative class $y_-$ including images lacking the pathology or disease, or images displaying a lower severity than the positive class. In general, the predicted class label $\hat{y}$ is not identical to the true class labels, y, since most classifiers are not perfect; however, this work is primarily concerned with classifier outputs, not the ground truth classifications. Accordingly, input classes are defined: $x_+$ and $x_-$ according to $\_F(x_{+/-})=\hat{y}_{+/-}$, i.e. $x_+$ corresponds to data that was predicted by the classifier to belong to the positive class, and similar for $x_-$. In the BAM framework the main generator was trained to transform data so that it is classified as negative by the classifier; that is, a generator $G_-$ was sought such that $F(G_-(x))=\hat{y}_{+/-}$, In the case that the input data was originally classified as positive, i.e. $x=x_+$ this creates "forged data", in which the target output classification differs from the classification of the input $\hat{y}_+$. If, alternatively, $G_-$ operates on data $x_-$ already predicted to belong to the negative class, the desired output classification matches the input, creating "preserved data". Both forged and preserved data were used during the training process to calculate loss. The cross-entropy loss $H_-$ between the classifier prediction on the forged data $F(G_-(x_+))$ and the desired prediction $\hat{y}_-$ was used to train the generator to produce data resembling the desired class. In addition, to prevent large changes to the main generator output, the mean absolute error loss $M_-$ between the raw input $x_-$ and the preserved data $G_-(x_-)$ was included in the loss.

However, simply optimizing over forged and preserved data can lead to overfitting, in which the main generator learns to modify features that were not learned by the classifier F (e.g., shared features between $x_+$ and $x_-$) in order to achieve the desired output label $\hat{y}_-$. To ensure that the main generator learns to remove relevant features (without removing irrelevant features) an assistant generator $G_+$ that performs the inverse task was also simultaneously trained. That is, the trained assistant generator was trained to produce $F(G_+(x))=\hat{y}_+$. Note that, like the main generator, this produces both preserved and forged data, since the assistant generator also acts on both $x_+$ and $\hat{x}_-$. The assistant generator is used in conjunction with the main generator to produce "cycled data" $G_-(G_+(x_-))$ and $G_+(G_-(x_+))$ created by allowing the main and assistant generator to operate on data forged by the other. The cycled loss, defined as the mean absolute errors between the original and cycled data $$L_c = \frac{1}{N_-}\sum_i |x_{-,i} - G_-(G_+(x_-, i))| + \frac{1}{N_+}\sum_j |x_{+,j} - G_+(G_-(x_+, j))|. \quad (1)$$

where $N_+$ and $N_-$ are the pixel number of positively and negatively classified images respectively, can then be included in the overall loss function in order to ensure that only features learned by the classifier are modified. The overall loss for each generator is then given by the sum of the cross-entropy loss between forged labels and predicted labels, the mean absolute error loss between preserved data and input data, and the cycled loss:

$$L_- = H_- + M_- + L_C, \quad (2)$$

$$L_+ = H_+ + M_+ + L_C.$$

Figure 14:
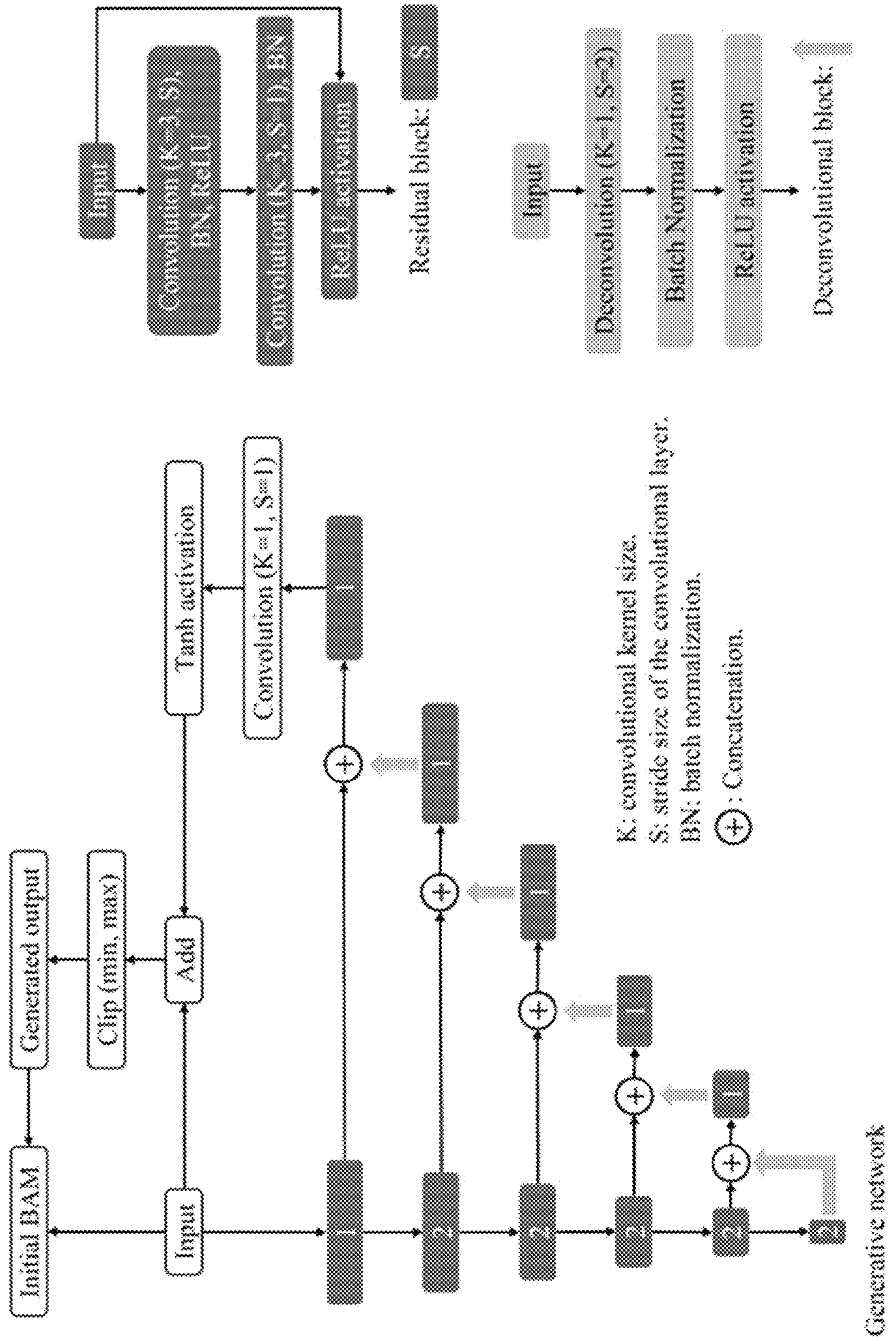
FIG. 14 illustrates the detailed architecture of main and assistant generators.

FIG. 14 illustrates the detailed architecture of main and assistant generators. The dark green patches and pale green arrows represent the residual and deconvolutional block, respectively. The number in the dark green patch is the stride size. The number of blocks can be adjusted based on the input. The number of residual blocks can be adjusted based on the size of the input. The generated output is calculated as the sum of input and Tanh output after clipping (the values higher or lower than original minimum or maximum of the input will be set to the maximum or minimum values, respectively) the values to original minimum and maximum.

Both main and assistant generators were constructed based on a U-shape residual convolutional neural network (FIG. 14). The output is calculated as the sum of input and Tanh output since both generators are trained to change necessary biomarkers that are learned by the classifier. To make sure the generator output has same value range of the input, clipping was used after the summation (the values higher or lower than original minimum or maximum of the input was be set to the maximum or minimum values, respectively). In addition, zero initialization was used for the last convolutional layer to make sure no unnecessary changing before the training.

B. Model Selection and BAM Generation

FIG. 14 illustrates a detailed architecture of the main (assistant) generator. The dark green patches and pale green arrows represent the residual and deconvolutional block, respectively. The number in the dark green patch is the stride size. The number of blocks can be adjusted based on the input.

After the training, the final model for the BAM generation was selected based on the validation loss of the main generator, because the assistant generator used negative input to generate the outputs that would be be classified positive by the trained classifier. Unlike the main generator, which removes the unique biomarkers with exact locations, the assistant generator adds biomarkers belonging to positive class without certain locations. Therefore, only the validation loss of main generator was used for model selection since the assistant generator would not produce predictable and/or certain outputs with biomarkers in accurate locations. The initial BAM was calculated between the output and input of the main generator. Since this is a difference image, it can have both positive and negative pixel values. The absolute difference between these values represents the overall contribution each biomarker made to the classification.

Alternatively, positive/negative values indicate regions in which pixel values in the output are higher/lower than the input in order for the classifier to produce a negative (non-disease) classification. These sign differences provide insight into how the trained classifier "understands" different biomarkers. Accordingly, the output of this framework is two processed BAMs, with the first obtained by measuring the absolute value of the difference values (e.g., the differences between respective pixel values) in the difference image:

$$BAM\text{-}C = f_g(|G_-(x_+) - x_+|), \quad (3)$$

while the second is generated by separating positive and negative values:

$$BAM\text{-}S = f_g(ReLU(G_-(x_+) - x_+)) - f_g(ReLU(x_+ - G_-(x_+))), \quad (4)$$

where $f_g$ is a Gaussian filter and ReLU is the activation function which only preserves positive values (see V. Nair and G. E. Hinton in *Proc. 27th ICML,* 2010, pp. 807-14; X. Glorot et al in *Proc. 14th AISTATS,* 2011, pp. 315-23). The BAM–C then indicates the overall contribution of each biomarker to classifier decision making, while the BAM–S indicates how different biomarkers were learned by the classifier.

C. Implementation Details

The proposed BAM generation framework was evaluated on a VGG19-based (K. Simonyan, and A. Zisserman, "Very deep convolutional networks for large-scale image recognition," arXiv preprint arXiv:1409.1556, 2014) classifier that took en face OCT and OCTA data as inputs to classify referable DR. Before the evaluation of the BAM generation framework, 60%, 20%, and 20% of the data were split for training, validation, and testing, respectively. Care was taken to ensure data from the same subjects was only included in one of the training, validation, or testing data sets. The classifier was trained and validated only using the training and validation data set. The trained classifier with the highest validation accuracy was selected to evaluate the BAM generation framework.

Parameters in the selected classifier were not changed during evaluation. The classifier achieved an overall accuracy of 96% on the testing data set, which is adequate to evaluate the BAM framework.

The BAM framework was trained, validated, and evaluated respectively based on the same data set of the classifier. During evaluation referable DR data was used as the positive class and non-referable data was used as the negative class. Two stochastic gradient descent optimizers with Nesterov momentum (momentum=0.9) were used simultaneously to train the generators. Hyperparameters during training included a batch size of 3,500 training epochs, and a learning rate of 0.001 was used for each of the training steps. The trained main generator with lowest validation loss was selected for the final evaluation. Perceptually uniform color maps were used to illustrate the BAMs (see P. Kovesi, "Good colour maps: How to design them," *arXiv preprint arXiv:*1509.03700, 2015); compared to the traditional Jet colormap, perceptually uniform color maps have even color gradients that can reduce visual distortions causing feature loss or the appearance of false features (F. Crameri et al., *Nature Communications, vol.* 11, no. 1, pp. 1-10, October 2020).

Results 50 healthy participants and 305 patients with diabetes were recruited and examined at the Casey Eye Institute, Oregon Health & Science University in the US, Shanxi Eye Hospital in China, and the Department of Ophthalmology, Aichi Medical University in Japan. After the DR severity grading, 199 nonreferable and 257 referable DR inputs were used to train, validate, and evaluate the DR classifier and the framework (Table 1).

TABLE 1

| DATA DISTRIBUTION | | | |
|---|---|---|---|
| Severity | Number of inputs | Age, mean (SD), y | Female, % |
| Non-referable DR | 199 | 48.8 (14.6) | 50.8% |
| Referable DR | 257 | 58.4 (12.1) | 49.0% |

Figure 15A:
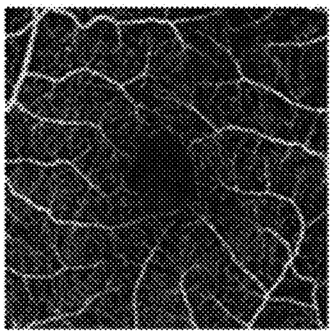
FIGS. 15A to 15J illustrate BAMs and other images for correctly predicted referable DR data.
Figure 15B:
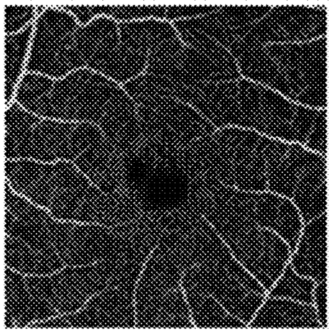
Figure 15C:
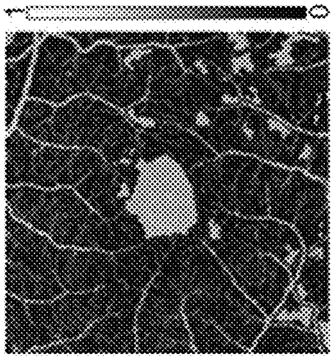
Figure 15D:
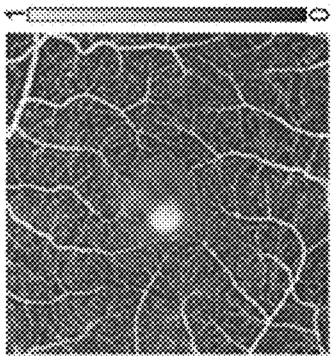
Figure 15E:
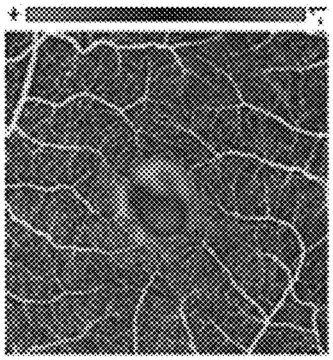
Figure 15F:
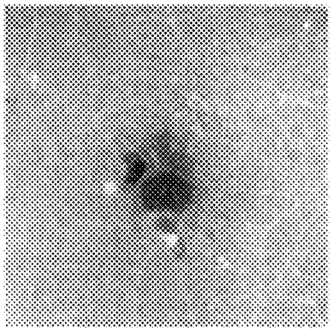
Figure 15G:
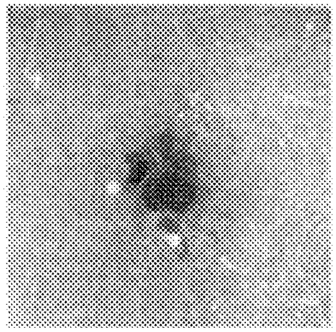
Figure 15H:
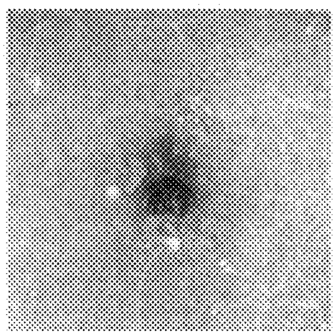
Figure 15I:
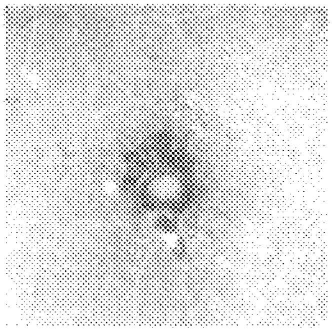
Figure 15J:
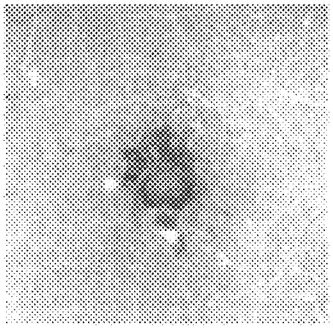

FIGS. 15A to 15J illustrate BAMs for a correctly predicted referable DR scan. FIG. 15A illustrates a superficial en face maximum projection, which is the first input channel for the BAM framework. FIG. 15B illustrates a forged main generator output image for this channel which should be classified as non-referable DR by the classifier. Compared to FIG. 15A, positive white dots and negative dark regions were added by the main generator. FIG. 15C illustrates a segmented non-perfusion area (NPA), which is an important DR-related biomarker, based on a previously reported deep learning method (J. Wang et al., *Biomed. Opt. Express*, vol. 11, no. 1, pp. 330-45, December 2020). FIG. 15D illustrates a BAM−C as the absolute difference between FIG. 15B and FIG. 15A after Gaussian filtering (Eq. 3). The highlighted areas are similar to the segmented NPA in FIG. 15C. FIG. 15E illustrates a BAM−S as the (non-absolute) differences between FIG. 15B and FIG. 15A after Gaussian filtering (Eq. 4). Red highlights pathological non-perfusion area while the foveal avascular zone (highlighted by green), which is not pathological, was identified as a separate feature by the classifier network. FIG. 15F illustrates en face mean projection over the inner retina, which is the second input channel. FIG. 15G illustrates a main generator output for this channel which should be classified as nonreferable DR by the classifier. Compared to FIG. 15F, positive white dots were added by the main generator. FIG. 15H illustrates inner mean projection of the segmented fluid (an important DR-related biomarker) based on a previously reported deep learning method (Y. Guo et al., *Translational vision science & technology*, vol. 9, no. 2, pp. 54-54, October 2020). FIG. 15I illustrates a BAM−C as the absolute difference between FIG. 15G and FIG. 15F after Gaussian filtering (Eq. 3). The highlighted areas resemble the fluid regions in FIG. 15H. FIG. 15I illustrates a BAM−S as the difference between FIG. 15G and FIG. 15F after Gaussian filtering (Eq. 4). FIG. 15J illustrates red highlighted areas. The red highlighted areas also focus on fluids, and no green highlighted area is shown, indicating that the network did not learn separate fluid features. This is anatomically accurate, since unlike NPA (which is non-pathologic in the foveal avascular zone) all retinal fluid is pathologic.

To demonstrate the utility of the proposed BAM framework, consider an eye correctly classified as referable DR by the DR classifier (FIGS. 15A to 15I). Compared to the clinical DR biomarkers (FIG. 15B and FIG. 15(G)), the BAMs of this example highlighted similar regions (FIG. 15D and FIG. 15I), which demonstrates that the BAMs can provide sufficient clinically meaningful interpretability to the DR classifier. Specifically, the BAM−C output indicates that the classifier focused on important pathologic features such as nonperfusion area (NPA) and retinal fluid (J. Wang et al., *Biomed. Opt. Express*, vol. 11, no. 1, pp. 330-45, December 2020; Y. Guo et al., *Translational vision science & technology*, vol. 9, no. 2, pp. 54-54, October 2020) in decision making. Additionally, the BAM−S indicates that the pathological NPAs were correctly differentiated from regions that are avascular in healthy eyes (i.e. the foveal avascular zone). In data from non-referable eyes the pixel values near fovea should span a wide range of pixel values corresponding to, from highest to lowest: larger vessels around fovea, small capillary structure, and the fovea avascular zone. These pixel populations are compressed in an en face OCTA angiogram of a referable DR eye (FIG. 15(A)). By adding positive values (white dots) around fovea and negative values in the fovea, the main generator expanded the range of pixel values to craft an image that appeared like a non-referable eye to the classifier (FIG. 15(B)). The structure of the generated image shows that classifier learned the anatomical structure near fovea in a normal (non-disease) eye.

Figure 16A:
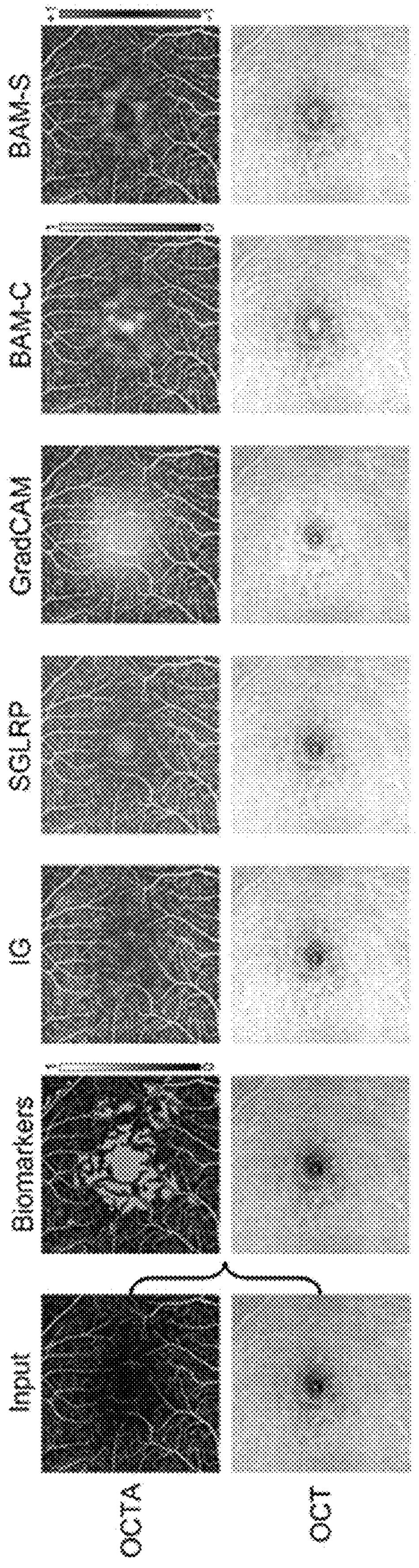
FIGS. 16A and 16B illustrate comparisons between the BAM generation framework and the other three interpretability methods.
Figure 16B:
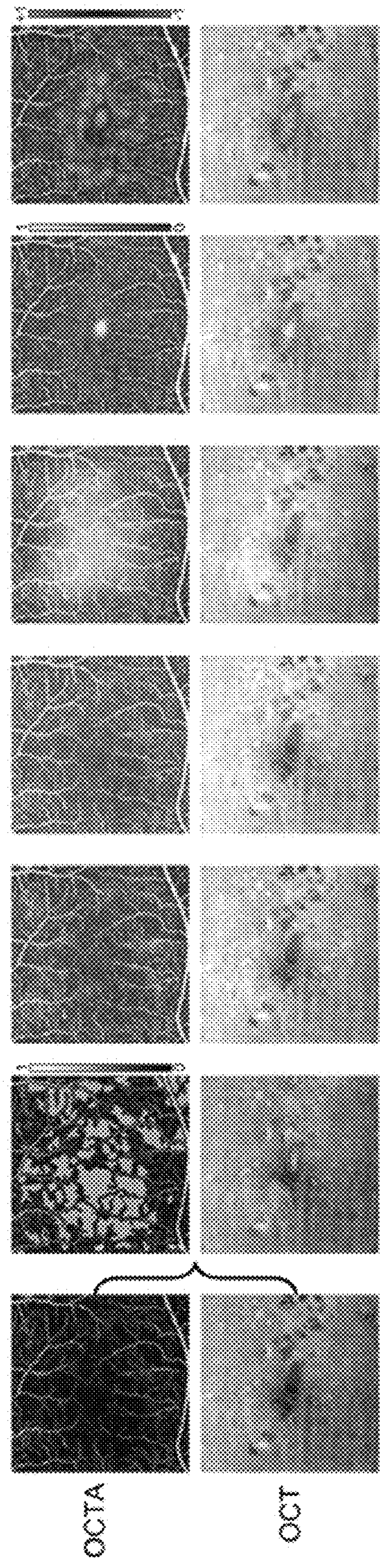

FIGS. 16(A) and 16(B) illustrate BAMs generated from false positive and false negative classified inputs. FIG. 16(A) illustrates an OCTA channel of a non-referable DR input which was misclassified as referable DR (a false positive). In both BAMs large regions without any apparent pathology were the focus of the network's attention. FIG. 16(B) illustrates an OCTA channel of a referable DR input which was misclassified as non-referable DR (false negative). Here, the classifier ignored non-perfusion area in the top left of the image.

Since the classifier output validation includes instances where the classifier makes an incorrect prediction, BAMs generated from a false positive and false negative diagnosis were also provided (FIGS. 16(A) and 16(B)). In FIGS. 16(A) and 16(B), the BAMs for the OCTA channel (not the OCT channel) are shown since the BAMs for the OCT channel did not show a significant difference compared to the BAMs of correctly classified inputs. In the BAMs of OCTA channel, compared to the correctly classified inputs, the normal tissues were also highlighted which makes it apparent that the classifier failed to differentiate normal from DR-affected tissue. Based on the BAMs of both correctly and incorrectly classified inputs, it was found that the BAMs of correctly classified inputs highlighted almost all of the DR-affected tissues, without significantly highlighting non-DR-affected tissues. But for the misclassified inputs, the BAMs highlighted both DR-affected tissue and normal tissue.

To demonstrate the advantages of the BAM generation framework, the output was compared with gradient-based (M. Sundararajan et al. in *Proc. of the* 34*th International Conference on Machine Learning,* 2017, pp. 3319-28), propagation-based (B. K. Iwana et al., "Explaining convolutional neural networks using softmax gradient layer-wise relevance propagation," *arXiv preprint arXiv:*1908.04351, 2019), and CAM-based methods (R. R. Selvaraju et al. in *Proc. of the IEEE International Conference on Computer Vision,* 2017, pp. 618-26). Compared to the attention maps generated by these methods, the BAMs show sharper distinctions between significant and insignificant regions for decision making, highlight features at higher resolution, and indicate that the classifier was able to distinguish between different types of features. In addition, the BAM framework was able to separately highlight the important features in en face OCTA and structural OCT rather than blending them together. This capability avoids loss of interpretability since the underlying anatomic features the network is trying to learn do not necessarily overlap in the separate channels (for example, NPA does not always overlap with diabetic macular edema). However, for graders reviewing the images, if structural OCT and OCTA features are not separated it may be unclear if healthy regions in one channel are being misinterpreted as pathologic, or if the pathology is in the other channel.

Figure 17A:
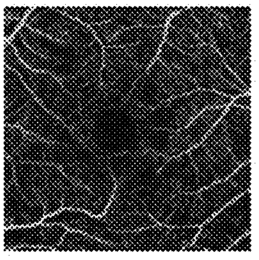
FIGS. 17A to 17D illustrate the comparison between the OCTA channel of BAMs generated from a main generator that was trained without an assistant generator and from a main generator that was trained with an assistant generator.
Figure 17B:
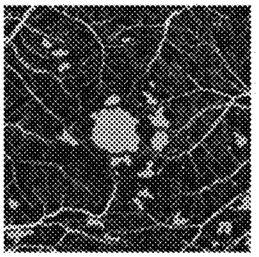

FIGS. 17A and 17(B) illustrate a comparison between the BAM generation framework and three other prominent (gradient, propagation, and class activation) attention maps (M. Sundararajan et al. in *Proc. of the* 34*th International Conference on Machine Learning,* 2017, pp. 3319-28; R. R. Selvaraju et al. in *Proc. of the IEEE International Conference on Computer Vision,* 2017, pp. 618-26; B. K. Iwana et al., "Explaining convolutional neural networks using softmax gradient layer-wise relevance propagation," *arXiv preprint arXiv:*1908.04351, 2019). The biomarkers column shows non-perfusion area (NPA) in OCTA channel and retinal fluid in the structural OCT channel, respectively, both segmented using previously reported deep learning methods (J. Wang et al., *Biomed. Opt. Express*, vol. 11, no. 1, pp. 330-45, December 2020; Y. Guo et al., *Translational vision science & technology*, vol. 9, no. 2, pp. 54-54, October 2020). Compared to the other three attention maps, the BAMs accurately highlight each classifier-selected biomarker at higher resolution and highlighted just the clinical DR biomarkers. In addition, the normal tissues (such as vessels between NPAs) that were not selected by the classifier were not highlighted by the BAMs. FIG. 17(A) illustrates results based on a referable DR case without diabetic macular edema (DME). FIG. 17(B) illustrates results based on a referable DR case with DME. Fluid, which is difficult to locate by eye in the en face OCT image, was highlighted by the BAMs (marked by orange arrows). Gradient-based and CAM-based methods, which only generate one-channel attention maps, should be contrasted with the separate attention maps for each channel produced by the BAM framework. While the attention map generated by propagation-based method can in principle highlight different areas in different channels, in this case this approach also highlighted similar areas in the structural OCT and OCTA channels. In addition, retinal fluid, which is difficult to identify by inspection of the en face structural OCT, was also highlighted by the BAM framework (FIG. 17(B)).

In the proposed framework, the assistant generator was used to make sure only the classifier-selected biomarkers were highlighted in the BAM framework. But the use of assistant generator also reduced the computational efficiency.

Figure 18A:
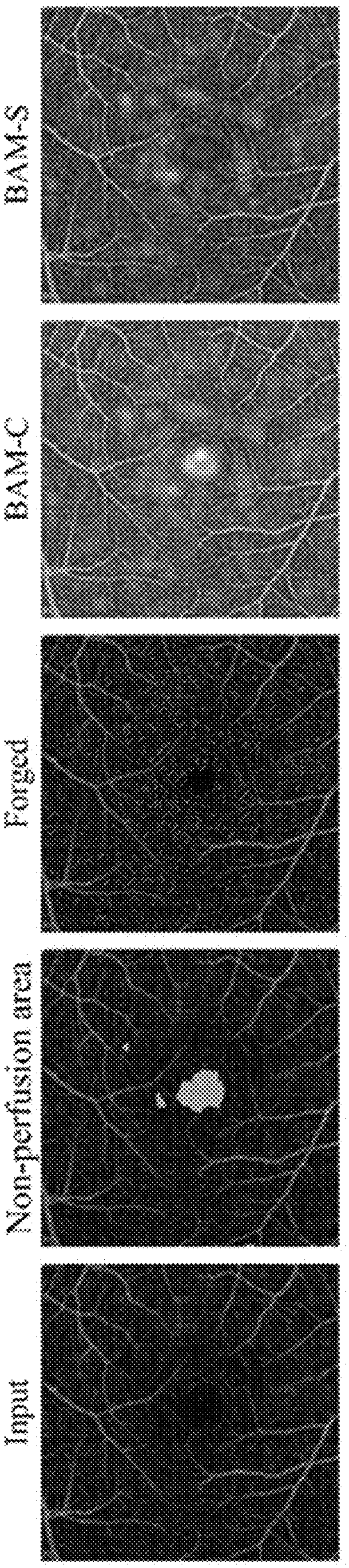
FIGS. 18A and 18B illustrates the BAMs generated from false positive and negative classified inputs.
Figure 18B:
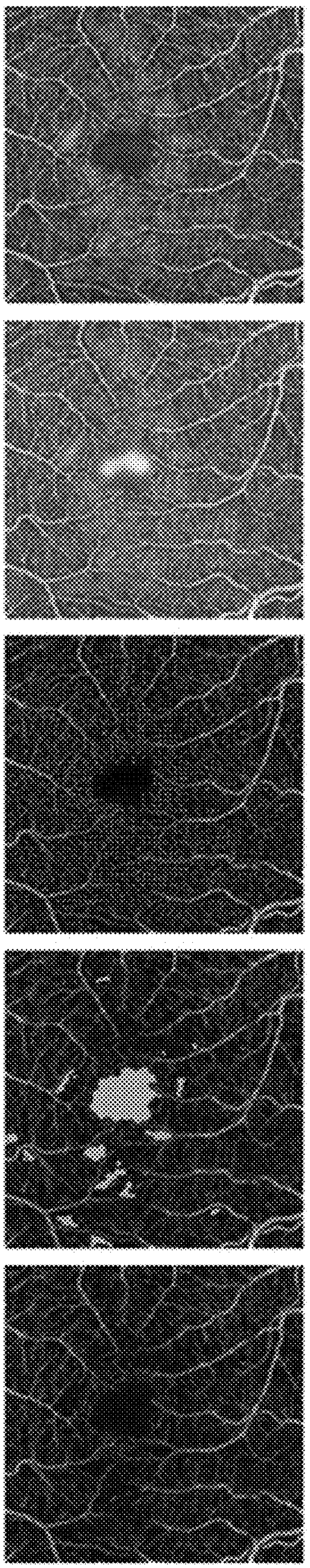

FIGS. 18A to 18D illustrate a comparison between the OCTA channel of BAMs generated from the main generator (trained without cycled loss using the assistant generator) and from the proposed framework, which included the assistant generator. FIG. 18A illustrates an OCTA channel of a referable DR input. FIG. 18B illustrates a non-perfusion area segmented using a previously published approach (J. Wang et al., *Biomed. Opt. Express*, vol. 11, no. 1, pp. 330-45, December 2020). FIG. 18C illustrates BAMs produced from a framework that only included a main generator. This framework highlighted non-pathologic features including healthy vessels (green arrows), produced lower resolution outputs, and failed to distinguish between non-pathologic and pathologic non-perfusion area. FIG. 18D illustrates a generated BAM based on the proposed framework with two generators avoids these pitfalls.

To explore the merit of the assistant generator, BAMs generated only based on the main generator (trained without cycled loss) were compared to BAMs generated from proposed framework (which included the assistant generator). The BAMs generated without the assistant generator produced lower resolution attention maps and highlighted features not related to DR pathology such as normal microvasculature and large vessels (marked by green arrows in FIG. 18(C)). In addition, the fovea avascular zone could not be distinguished from the pathological non-perfusion areas in the BAM–S only based on main generator (FIG. 18(C)).

Discussion

A BAM generation framework is proposed herein to aid in the interpretation of all the deep-learning-aided disease classification systems. The core design concept of this framework is the recognition of unique requirements in medical compared to non-medical image classification. By designing around this principle, a framework was implemented that enables visualization of specific biomarkers, rather than highlighting relevant features shared between healthy and pathologic images, and which are consequently irrelevant for verifying classifier outputs in a diagnostic context. The framework includes using two U-shaped CNN generators (a main and an assistant generator) that are trained using a trained classifier and performing generative adversarial learning. At least one of the U-shaped CNN generators is used to generate BAMs. The BAMs clearly highlight biomarkers selected by the classifier, which can facilitate the quick identification of pathology by clinicians in real-world applications. The BAM–S is also capable of distinguishing between multiple types of features in the same image. The proposed BAM generation framework is the first interpretability method specifically designed for deep-learning-aided disease classifiers in medical imaging. Based on visual comparison between the BAM and attention maps generated by other methods this framework achieved state-of-the-art performance in providing interpretability to a DR classifier based on OCT and OCTA.

Real-world clinicians resist the use of deep learning classifiers for medical diagnosis, because it is often impossible for the clinicians to determine what the classifiers rely on in their assessments. Existing interpretability methods were designed for nonmedical image classification and produce attention maps that are not necessarily useful for validating classifier decision making in a medical context (FIGS. 17(A) and (B)). A lack of interpretability in deep learning classifiers could lead to both ethical and legal challenges in the medical field, and as such a heuristic method that can provide sufficient interpretability for deep-learning aided classifiers is now recognized as an urgent priority (J. He et al., *Nature medicine*, vol. 25, no. 1, pp. 30-36, January 2019; S. Gerke S et al., *Artificial intelligence in healthcare, Academic Press, pp.* 295-36, 2020; Z. Salahuddin et al., *Computers in biology and medicine*, vol. 140, pp. 105111, 2022). Poor interpretability conflicts with the principles of informed consent (S. Gerke S et al., *Artificial intelligence in healthcare, Academic Press*, pp. 295-36, 2020). Additionally, it is difficult to investigate bias if the reasons for the classifier's decision making are unclear (J. He et al., *Nature medicine*, vol. 25, no. 1, pp. 30-36, January 2019; S. Gerke S et al., *Artificial intelligence in healthcare, Academic Press*, pp. 295-36, 2020). In part to address these concerns the European Union's General Data Protection Regulation law requires that algorithm decision-making be transparent before it can be utilized for patient care (Z. Salahuddin et al., *Computers in biology and medicine*, vol. 140, pp. 105111, 2022; M. Temme, *Eur. Data Prot. L. Rev., vol.* 3, pp. 473, 2017). Legally the liability for medical negligence is also hard to judge if clinicians cannot interpret the classifiers they are using (S. Gerke S et al., *Artificial intelligence in healthcare, Academic Press*, pp. 295-36, 2020). Beyond these concerns, algorithm interpretability is also important for research. Adequately interpretable attention maps can facilitate the new biomarker discovery (Z.

Salahuddin et al., *Computers in biology and medicine*, vol. 140, pp. 105111, 2022), which has the potential to improve clinical diagnosis and an understanding of disease pathophysiology.

A DR classifier based on OCT and OCTA was used to evaluate the BAM generation framework. DR is a leading cause of preventable blindness globally (C. P. Wilkinson et al., *Ophthalmology*, vol. 110, no. 9, pp. 1677-82, September 2003; T. Y. Wong et al., *Ophthalmology*, vol. 125, no. 10, pp. 1608-22, October 2018; C. J. Flaxel et al., *Ophthalmology*, vol. 127, no. 1, pp. 66-145, January 2020; D. A. Antonetti et al., *N. Engl. J. Med.*, vol. 366, pp. 1227-39, 2012), and OCT and OCTA can generate depth-resolved, micrometer-scale-resolution images of ocular fundus tissue and vasculature (D. Huang et al., *Science*, vol. 254, no. 5035, pp. 1178-81, November 1991; S. Makita et al., *Optics express*, vol. 14, no. 17, pp. 7821-40, August 2006; An and Wang, *Optics express*, vol. 16, no. 15, pp. 11438-52, July 2008; Y. Jia et al., *Opt. Express.*, vol. 20, no. 4, pp. 4710-25, February 2012), and so an interpretability framework for this disease based on this technology is meritorious of itself. However, we also chose this combination of disease and imaging modalities since together they emphasize the strengths of the approach described herein. Compared disease diagnosis in which essentially only a single biomarker is relevant (e.g., brain tumor diagnosis based on MRI (M. K. Abd-Ellah et al., *Magnetic resonance imaging*, vol. 61, pp. 300-18, September 2019)) that benefit more from image segmentation, DR severity is assessed based on several different biomarkers, including microaneurysms, non-perfusion, edema, and more (Early Treatment Diabetic Retinopathy Study Research Group, *Ophthalmology*, vol. 98, no. 5, pp. 823-33, May 1991). The BAM framework was capable of identifying separate DR associated pathologies in the structural OCT and OCTA channels, and furthermore the BAM−S was even capable of distinguishing separate features within a single channel (FIG. 15).

Evaluation based on more diseases and imaging modalities can be performed in the future since the BAM generation framework described in this study can be easily transferred to other interpretability tasks. In particular, the BAM framework is easily generalized to a larger number of classifications (for example, non-referable/referable/vision threatening DR). For a binary disease classifier, the main generator takes inputs to generate forged negative output, and vice versa for the assistant generator. For a single disease classifier which classifies each input to S (S≥3) severities overall S−1 BAMs can be used to provide sufficient interpretability to this classifier. Each BAM is generated between two adjacent severities by respectively combing all lower and higher severities as one class. Alternatively, for a multiple disease classifier (e.g. a system that diagnoses DR and age-related macular degeneration) a BAM for each disease can be generated between the selected disease and normal class.

Unlike other interpretability methods, the BAM generation framework of this example is using deep learning networks to interpret another deep learning network, which leads to its own questions about interpretability. For networks in which the training target is classification or segmentation, the interpretability issue can be described as how the classification or segmentation results are acquired. In medical image analysis, the concern for interpretability can be further described as whether the clinically meaningful biomarkers are used by the network to make decisions. However, the training target of the framework is generating an output which can be classified as negative by the trained classifier from a positive input. The interpretability issue in this context can be described as asking how the output is generated to achieve the desired classification, and asking which biomarkers correlate with classifier decision making.

The BAM apparently improved interpretability by highlighting the biomarkers that were changed by the using the BAM image generation framework. Therefore, the BAM generation framework is self-interpreted and can be used to provide interpretability to deep-learning-aided disease classifiers.

Conclusion

A BAM generation framework is proposed herein that can be used to provide interpretation of deep-learning-aided disease classification systems. The BAMs demonstrated here separately highlighted different classifier-selected biomarkers at high resolution, which could enable quick review by image graders to verify whether clinically meaningful biomarkers were learned and used by the classifier. The BAM generation framework could improve the clinical acceptability and real world applications for deep-learning-aided disease classification systems. The framework may also facilitate new biomarker discovery on medical images used for diagnosis of related disease.

Second Example

Figure 11:
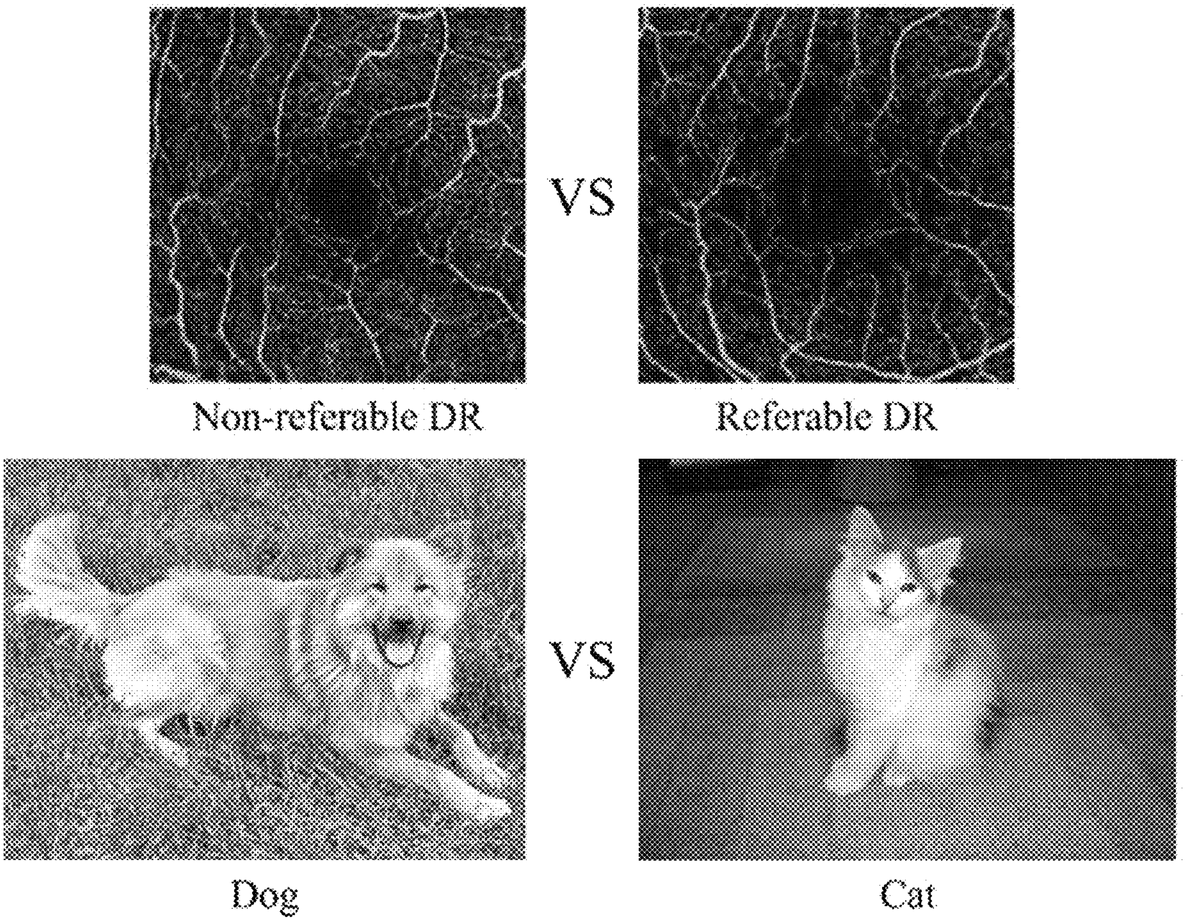
FIG. 11 illustrates a comparison between medical image-based disease classification (e.g., referable DR classification) and other types of classification, like cat and dog classification.

FIG. 11 illustrates a comparison between medical image-based disease classification (e.g., referable DR classification) and other types of classification, like cat and dog classification. Comparing the bottom two images, the background between dog and cat can be totally different and the difference between the unique features of dog and cat is also large. But comparing the top two en face optical coherence tomography angiography (OCTA) images, the non-referable and referable DR have similar backgrounds (normal anatomical structure). Only the referable DR has the unique features (DR-related biomarkers). Thus, disease classification can be distinct from other types of image classification.

Deep learning is a powerful technique for automated disease classification. However, it is unclear how deep learning classification models arrive at their results, limiting their real-world applications. To improve interpretability, a novel biomarker activation map (BAM) generation framework based on generative adversarial learning (GAL) is described.

The BAM generation framework of this example was constructed by two generators with a U-shaped architecture. The main generator was trained to produce an output that the pre-trained classifier would classify as non-disease or lower severity from a disease or higher severity input, while the assistant generator was trained to produce an output that would be classified as disease or higher severity. The BAM was calculated as the different image between the output and input of the main generator. The proposed framework was evaluated on a diabetic retinopathy (DR) classifier. The DR classifier was previously trained (60%), validated (20%) and evaluated (20%) based on 456 macular images acquired from optical coherence tomography (OCT) and its angiography (OCTA). Masked trained retina specialists graded retinas depicted in the images as having non-referable DR or referable DR based on a clinical standard. In the evaluation, the BAM generation framework was trained, validated, and evaluated based on the same OCT and OCTA data set.

The generated BAMs explicitly highlighted the nonperfusion area and fluids, which represent the most important DR biomarker visible in the input images. In addition, each classifier-selected biomarker was highlighted separately, which means a clinician reviewing the BAMs could quickly discern each biomarker during the revision. The generated BAMs using the GAL method described herein could provide sufficient interpretability to help clinicians utilize deep-learning-aided disease classification systems. This innovation may also facilitate the new biomarker discovery on input medical images used for diagnosis of related disease.

Materials 50 healthy participants and 305 patients with diabetes were recruited at the Casey Eye Institute, Oregon Health & Science University in the US; Shanxi Eye Hospital in China; and the Department of Ophthalmology, Aichi Medical University in Japan. Diabetic patients were included with the full spectrum of disease from no clinically evident retinopathy to proliferative diabetic retinopathy. One or both eyes of each participant underwent 7-field color fundus photographs and an OCTA scan using a commercial 70-kHz spectral-domain OCT (SD-OCT) system (RTVue-XR Avanti, Optovue Inc) with 840-nm central wavelength. The scan depth was 1.6 mm in a 3.0×3.0 mm region (640×304×304 pixels) centered on the fovea. Two repeated B-frames were captured at each line-scan location. Blood flow was detected using the split-spectrum amplitude-decorrelation angiography (SSADA) algorithm based on the speckle variation between two repeated B-frames (Huang D et al., Science. 1991; 254(5035):1178-81 (Jia Y et al., Opt. Express. 2012; 20(4):4710-25; Gao S S et al., Opt. Lett. 2015; 40(10):2305-08). The OCT structural images were obtained by averaging two repeated and registered B-frames. For each data, two continuously acquired volumetric raster scans (one x-fast scan and one y-fast scan) were registered and merged through an orthogonal registration algorithm to reduce motion artifacts (Kraus M F et al., Biomed. Opt. Express. 2014; 5(8):2591-13). In addition, the projection-resolved (PR) OCTA algorithm was applied to all OCTA scans to remove flow projection artifacts in the deeper layers (Zhang M et al., Biomed. Opt. Express. 2016; 7(3):816-28; Wang J et al., Biomed. Opt. Express. 2017; 8(3):1536-48). Scans with a signal strength index (SSI) lower than 50 were excluded. The data characteristics are shown below (see Table 1).

A masked trained retina specialist (TH) graded the photographs based on Early Treatment of Diabetic Retinopathy Study (ETDRS) scale (Early Treatment Diabetic Retinopathy Study Research Group. Fundus photographic risk factors for progression of diabetic retinopathy: ETDRS report number 12, Ophthalmology. 1991; 98(5):823-33; Ophthalmoscopy D, Levels E. International clinical diabetic retinopathy disease severity scale detailed table, 2002) using the 7-field color fundus photographs. The presence of DME was determined using the central subfield thickness from the structural OCT based on the DRCR.net standard (Flaxel C J, Adelman R A, Bailey S T, et al. Diabetic retinopathy preferred practice Pattern®. Ophthalmology. 2020; 127(1): 66-145). Non-referrable DR (nrDR) was defined as an ETDRS level greater than 35 and without DME; referrable DR (rDR) as ETDRS level 35 or lower, or any DR with DME (Wong T Y et al., Ophthalmology, 2018; 125(10): 1608-22). The participants were enrolled after an informed consent in accordance with an Institutional Review Board approved protocol. The study complied with the Declaration of Helsinki and the Health Insurance Portability and Accountability Act.

Figure 12:
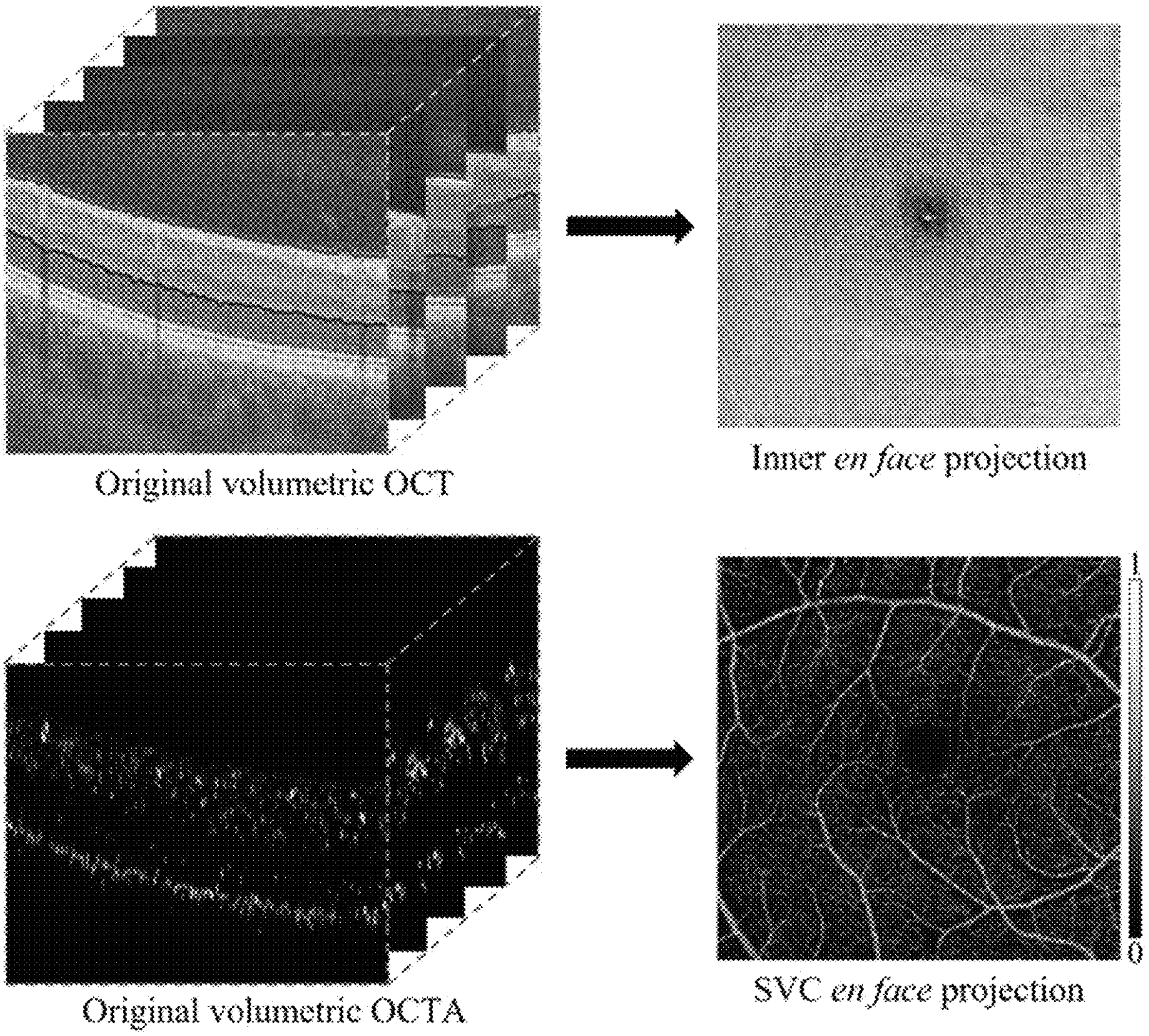
FIG. 12 illustrates generations of inner and superficial vascular complex (SVC) en face projections respectively from original volumetric OCT and OCTA.

FIG. 12 illustrates inner and superficial vascular complex (SVC) en face projections respectively generated from original volumetric OCT and OCTA. Three boundaries Vitreous/ILM (red), IPL/INL (green) and OPL/ONL (blue) were segmented for the generation process. For each pair of OCT and OCTA data, the following retinal layer boundaries were automatically segmented (FIG. 12) based on the commercial software in the SD-OCT system (Avanti RTVue-XR, Optovue Inc): the boundary between vitreous and inner limiting membrane (ILM), the boundary between inner plexiform layer (IPL) and inner nuclear layer (INL), and the boundary between outer plexiform layer (OPL) and outer nuclear layer (ONL). In addition, for the cases with severe pathologies, the automated layer segmentation was manually corrected by graders using the customized COOL-ART software (M. Zhang et al., Biomed. Opt. Express vol. 6, no. 12, pp. 4661-75, 2015).

Based on the segmented boundaries, two en face projections respectively from OCT reflectance signals and OCTA decorrelation values were generated (FIG. 12). The en face OCT was generated as the inner retinal en face average projection (Vitreous/ILM to OPL/ONL) of the volumetric OCT (FIG. 12). The en face OCTA was generated as the en face maximum projections of the superficial vascular complex (SVC). The SVC was defined as the inner 80% of the ganglion cell complex (GCC), which included all structures between the ILM and IPL/INL border (Zhang M et al., Investig. Ophthalmol. Vis. Sci. 2016; 57(13):5101-06; J. P. Campbell et al., Sci. Rep., vol. 7, p. 42201, 2017). The generated en face OCT and OCTA images were combined into a single two-channel input image for the DR classifier.

Methods

FIGS. 13A to 13C Illustrate a BAM generation framework architecture and training process. Two generators were trained to produce the initial BAM. FIG. 13A shows that input disease (or higher severity) data is acted on by the main and assistant generators (blue and green arrows, respectively). The main generator trains to produce a forged data from this input that the classifier will classify as non-disease (or lower severity) data. The assistant generator also acts on this input data and trains to produce a preserved disease data. The assistant generator is then applied to the forged non-disease output of the main generator to produce cycled disease data. FIG. 13(B) shows that training from a non-disease (or lower severity) input is symmetric, with the labels switching roles. FIG. 13C shows that training of the main and assistant generators are performed at the same time based on the loss functions respectively. This scheme prevents the main generator from overfitting the forged non-disease data.

The main architecture of the BAMs generation framework including two generators (main and assistant) (FIG. 13A). For a trained disease classifier, the main generator uses disease or higher severity data as inputs and generates the outputs which can be classified as non-disease or lower severity by the classifier (FIG. 13A). The assistant generator using non-disease or lower severity data as inputs and generate the outputs which can be classified as disease or higher severity by the classifier (FIG. 13A). The initial BAM was constructed as the difference image between the output and input of the main generator (i.e., the image generated when respective pixels of the input of the main generator are subtracted from the respective pixels of the output of the main generator). The final BAM was then calculated after applying a gaussian filter to the initial BAM.

Main Generator

To explore which unique disease biomarkers were potentially selected by the classifier, the main generator was constructed as a U-shaped residual CNN (FIG. 14) and used to generate the forged non-disease (or higher severity) data, which would be classified as non-disease by the classifier, from the input disease (or higher severity) data (Eq. 5).

$$XN_f = G_m(XD_i) \tag{5}$$

where $XN_f$ was the forged non-disease data, $XD_i$ was the input disease data and $G_m$ was the main generator. The forged non-disease data was then used as the input of the trained classifier to calculate the forged non-disease prediction (Eq. 6).

$$P_n = F(XN_f) \tag{6}$$

where $P_n$ was the forged non-disease prediction and F was the trained classifier. In the training, the forged non-disease cross-entropy loss was calculated between the non-disease ground truth label and forged non-disease prediction (Eq. 7).

$$C_n = -\sum_{k=1}^{K} P_{n_k} \times \log g_k \tag{7}$$

where K was the number of classes, $CN_f$ was the forged non-disease cross entropy and g was the ground truth label. In addition, to reduce the changes to the shared features between non-disease and disease data, the preserved non-disease data was generated by the main generator from the input non-disease data. In the training, the mean absolute error (MAE) loss was calculated between the input and preserved non-disease data (Eq. 8).

$$M_n = \frac{1}{J}\sum_{j} |XN_i - G_m(XN_i)| \tag{8}$$

where $XN_i$ was the input non-disease data and J was the number of elements in $XN_i$.

FIG. 14 illustrates the detailed architecture of main and assistant generators. The number of residual blocks can be adjusted based on the size of the input. The generated output is calculated as the sum of input and Tanh output after clipping (the values higher or lower than original minimum or maximum of the input will be set to the maximum or minimum values, respectively) the values to original minimum and maximum.

Assistant Generator

If the main generator was trained only based on $C_n$ and $M_n$, the forged non-disease data could be overfitted compared to the structure of real non-disease data. To make sure only the unique disease biomarkers were changed by the main generator, the assistant generator was constructed (FIG. 14) and used to generate the forged disease data, which would be classified as disease by the classifier, from the input non-disease data. The cycled disease and non-disease data could be then generated based on both main and assistant generators (Eq. 9).

$$XD_c = G_a(XN_f) \tag{9}$$

$$XN_c = G_m(G_a(XN_i))$$

where $XD_c$ and $XN_c$ respectively were the cycled disease and non-disease data, $XN_i$ was the input non-disease data, and $G_a$ was the assistant generator. The generated $XD_c$ and $XN_c$ were used to calculate the cycled loss which could further reduce the changes to the shared features between non-disease and disease data (Eq. 10).

$$L_c = \frac{1}{2J}\sum_{j} (|XR_i - XR_c| + |XN_i - XN_c|) \tag{10}$$

where $L_c$ was the cycled loss. In the training, the cycled loss was used for both main and assistant generators. In addition, the cross entropy and MAE based on similar procedures (Eqs. 6 and 7) were also used to train the assistant generator. The main and assistant generators were trained at the same time respectively based on the three losses (Eq. 11).

$$L_m = C_n + M_n + L_c \tag{11}$$

$$L_a = C_d + M_d + L_c$$

where $C_d$ was the disease cross entropy loss, $M_d$ was the disease MAE loss, and $L_m$ and $L_a$ respectively were the loss functions for main and assistant generators.

BAM Generation

The initial BAM was generated as the difference between the output and input of the main generator (i.e., the output minus the input of the main generator). The initial BAM had both positive and negative values since the Tanh activation was used after the last convolutional layer of main generator. The positive values represented the classifier-selected biomarkers which have lower values compared to the non-disease tissue in same region. The negative values represented the classifier-selected biomarkers, which have higher absolute values compared to the non-disease tissue in same region. The absolute values represent how much contribution the biomarkers made to the classification. For each input, two BAMs would be generated. The first BAM was generated by combining the absolute values of all differences (BAM–C, Eq. 12). The second BAM was generated by separating the positive and negative values (BAM–S, Eq. 13).

$$BAM\text{–}C = f_g(|G_-(x_+) - x_+|), \tag{12}$$

$$BAM\text{–}S = f_g(ReLU(G_-(x_+) - x_+)) - f_g(ReLU(x_+ - G_-(x_+))), \tag{13}$$

where $f_g$ was the gaussian filter and Relu was the activation function which only preserves the positive value. The BAM–C was used to show the contribution of each biomarker. The BAM–S was used to show how each biomarker was understood by the classifier.

Applications in Other Disease Classification Systems

In a binary disease classification system, the main generator takes data of disease or higher severity as inputs to generate the forged non-disease or lower severity data, and vice versa for the assistant generator. For a system classifying a severity of disease that has multiple possible severity levels, the BAM generation for highest severity is the same as the binary system by combining lower-severity data as one class. For a middle class, two BAMs are used to provide sufficient interpretability for the trained classifier. The first BAM is generated between the selected class and a class representing a combination of the lower classes. The first BAM can be used to visualize the potentially classifier-selected biomarkers that the middle class has, compared to lower classes. The second BAM is generated between the higher classes (combined as one) and the selected class. The second BAM is used to visualize the potentially classifier-selected biomarkers that the middle class lack, compared to higher classes. For a system that classifies multiple diseases, the BAMs of each disease can be generated between the selected disease and non-disease class.

Implementation Details

The proposed BAM generation framework was evaluated on a VGG19-based (K. Simonyan et al., Proc. ICLR, 2015) classifier which used the en face OCT and OCTA data as input to classify referable DR. Before the evaluation of the BAM generation framework, from the whole data set, 60%, 20%, and 20% of the data were split for training, validation, and testing, respectively. Care was taken to ensure data from the same subjects were only included in one of the training, validation, or testing data sets. The classifier was trained and validated using the training and validation data set. The trained classifier with highest validation accuracy was selected to evaluate the BAM generation framework. In addition, the classifier achieved an overall accuracy of 96% which proved the classifier has sufficient performance for the evaluation. Table 2 lists the distribution of data used in this example.

TABLE 2

DATA DISTRIBUTION

| Severity | Number of inputs | Age, mean (SD), y | Female, % |
|---|---|---|---|
| Non-referable DR | 199 | 48.8 (14.6) | 50.8% |
| Referable DR | 257 | 58.4 (12.1) | 49.0% |

Two stochastic gradient descent optimizers with Nesterov momentum (momentum=0.9) were respectively used in the trainings of two generators at the same time. In the training of generators, the batch size was set to 3, the training epoch was set to 500, and the learning rate was set to 0.001 for the training steps. The trained main generator with lowest validation loss was selected for the final evaluation. Perceptually uniform color maps were used to show the generated BAMs in evaluation (Kovesi P. Good colour maps: How to design them, arXiv:1509.03700, 2015). Compared to the traditional Jet colormap, the perceptually uniform color maps have even color gradients and can reduce the visual distortion which can cause the features loss or appearance of false features (Fabio Crameri et al., Nature Communications 11, 5444 (2020)).

Results

FIGS. 15A to 15J illustrate examples of BAMs and other images for correctly predicted referable DR data. FIG. 15A illustrates the superficial en face maximum projection which was the first channel of the input. FIG. 15B illustrates the first channel of the main generator output which could be classified as non-referable DR by the classifier. For a better visualization, the value of different points was multiplied by 10. FIG. 15C illustrates a segmented non-perfusion area (NPA) (an important DR-related biomarker) based on a previously reported deep learning method. FIG. 15D illustrates a BAM-C which was calculated as the absolute difference between FIGS. 15B and 15A after the gaussian filter (Eq. 12). The highlighted areas have strong correlation with NPAs in FIG. 15C. FIG. 15E illustrates a BAM-S which was calculated as the combination of positive and negative differences between FIGS. 15B and 15A, respectively, after two gaussian filters (Eq. 13). The red highlighted areas focus on pathological non-perfusion area while ignoring the foveal avascular zone (highlighted by green). FIG. 15F illustrates an inner en face mean projection which was the second channel of the input. FIG. 15G illustrates a second channel of the main generator output which could be classified as non-referable DR by the classifier. For a better visualization, the value of different points was multiplied by 10. FIG. 15H illustrates an inner mean projection of the segmented fluid (important DR-related biomarker) based on a previously reported deep learning method. FIG. 15I illustrates a BAM-C which was calculated as the absolute difference between FIGS. 15G and 15F after the gaussian filter (Eq. 12). The highlighted areas have strong correlation with fluids in FIG. 15H. FIG. 15J illustrates a BAM-S which was calculated as the combination of positive and negative differences between FIGS. 15G and 15F, respectively, after two gaussian filters (Eq. 13). The red highlighted areas also focus on fluids and no green highlighted area is shown.

To provide interpretability for the trained VGG19-based classifier, BAM-C and BAM-S were both generated for correctly predicted referable DR data. Compared to two important DR biomarkers, non-perfusion area (FIG. 15C) and fluid (FIG. 15H), the similar areas were highlighted as the classifier-selected biomarkers in the BAMs (FIGS. 15D and 15I). The strong correlation between the classifier-selected and DR-related biomarkers proved the trained classifier had learned the clinical standard for DR classification. In addition, compared to the segmented non-perfusion areas (FIG. 15C), the pathological non-perfusion areas (red areas) were distinguished from the fovea avascular zone (green area in the center) in the BAM-S (FIG. 15E). Because in non-disease data, the pixel values near fovea should have three levels. From high to low values, the three levels respectively are associated with large microvascular around fovea, small microvascular under the large vessels, and fovea avascular zone. The three-level structure was reduced to one pixel level in the en face OCTA of a referable DR sample (FIG. 15A). By adding positive values around fovea and negative values in the fovea (FIG. 15E), the three-level structure could be rebuilt in the output which could be classified as non-referable DR by the classifier (FIG. 15B). This rebuilt structure provided by the BAM-S proved the anatomical structure near fovea of a non-disease eye has been learned by the trained classifier.

FIGS. 15A to 15J illustrate generated BAMs for correctly predicted referable DR data. FIG. 15A illustrates the superficial en face maximum projection which was the first channel of the input. FIG. 15B illustrates the first channel of the main generator output which could be classified as non-referable DR by the classifier. For a better visualization, the value of different points was multiplied by 10. FIG. 15C illustrates the segmented non-perfusion area (important DR-related biomarker) based on a previously reported deep learning method. FIG. 15D illustrates the BAM-C which was calculated as the absolute difference between FIGS.

15A and 15B after the gaussian filter (Eq. 12). The highlighted areas have strong correlation with non-perfusion area in FIG. 15C. FIG. 15E illustrates the BAM–S which was calculated as the combination of positive and negative differences between FIGS. 15B and 15A respectively after two gaussian filters (Eq. 6). The red highlighted areas focus on pathological non-perfusion area while ignoring the foveal avascular zone. The green highlighted areas focus on the foveal avascular zone. FIG. 15F illustrates the inner en face mean projection which was the second channel of the input. FIG. 15G illustrates the second channel of the main generator output which could be classified as non-referable DR by the classifier. For a better visualization, the value of different points was multiplied by 10. FIG. 15H illustrates the inner mean projection of the segmented fluid volumes (important DR-related biomarker) based on a previously reported deep learning method. FIG. 15I illustrates the BAM–C which was calculated as the absolute difference between FIGS. 15G and 15F after the gaussian filter (Eq. 5). The highlighted areas have strong correlation with fluids in FIG. 15H. FIG. 15E illustrates the BAM–S which was calculated as the combination of positive and negative differences between FIGS. 15G and 154F respectively after two gaussian filters (Eq. 13). The red highlighted areas also focus on fluids and no green highlighted area is showed.

FIGS. 16A and 16B illustrate comparisons between the BAM generation framework and the other three interpretability methods. The biomarkers for OCTA and OCT were non-perfusion area and fluids, respectively. As can be seen, based on the segmented biomarkers, the BAM framework provides more accurate visualization of the classifier-selected biomarkers than the other three heatmaps. FIG. 16A illustrates the results based on a referable DR data without diabetic macular edema. FIG. 16B illustrates the results based on a referable DR data with diabetic macular edema. The fluids cannot be identified by naked eye on the en face OCT were highlighted by the BAMs (marked by orange arrows).

To prove the advantages of the BAM generation framework, the comparison between the BAM framework and the other three different interpretability methods were performed (FIG. 16). The three methods respectively were Integrated Gradients (IG) (Sundararajan et al., Axiomatic attribution for deep networks in Proceedings of the 34th International Conference on Machine Learning-Volume 70, pages 3319-28. JMLR. org, 2017), Softmax Gradient Layer-wise Relevance Propagation (SGLRP) (Iwana et al., Explaining convolutional neural networks using softmax gradient layer-wise relevance propagation, arXiv: 1908.04351, 2019), and Gradient-Weighted Class Activation Map (GradCAM) (Selvaraju R R et al., Grad-CAM: visual explanations from deep networks via gradient-based localization in: Proceedings of the IEEE International Conference on Computer Vision; 2017). Compared to the other three heatmaps, the BAMs could accurately highlight the DR-related biomarkers, and each area with biomarker was highlighted separately, which enables clinicians to more efficiently discern each biomarker. In addition, the highlighted areas between en face OCTA and OCT were different in the BAMs described here. Because the biomarkers which could be identified through the en face OCTA and OCTA were also different. But IG and GradCAM could only generate one-channel heatmaps which could not be used to differentiate the biomarkers respectively from en face OCTA and OCT. The heatmap generated by SGLRP also highlighted similar areas between en face OCTA and OCT.

Figure 17C:
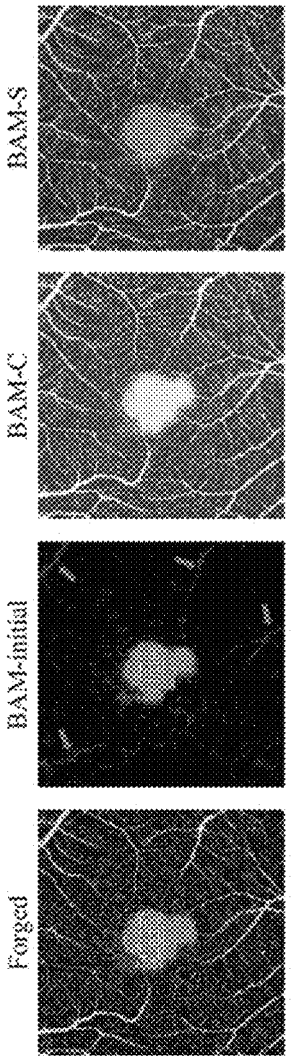
Figure 17D:
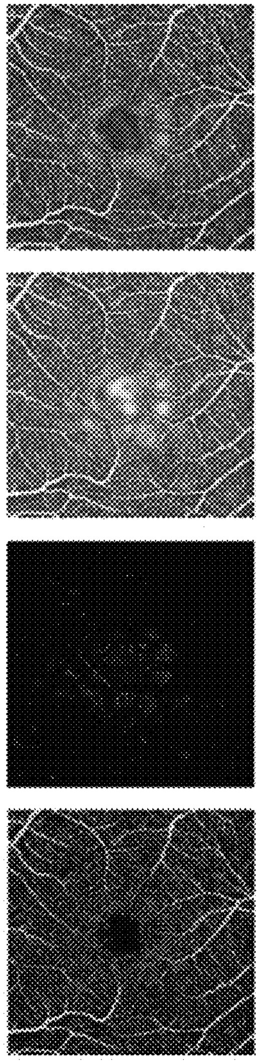

FIGS. 17A to 17C illustrate the comparison between the OCTA channel of BAMs generated from a main generator that was trained without an assistant generator and from a main generator that was trained with an assistant generator. FIG. 17A illustrates the OCTA channel of a referable DR input. FIG. 17B illustrates segmented non-perfusion area covered on FIG. 17A. FIG. 17C illustrates the generated BAM based only on the main generator. The highlighted non-disease large vessels were marked by green arrows. FIG. 17D illustrates the generated BAM based on proposed framework with two generators.

In the proposed framework, the assistant generator was used to make sure only the classifier-selected biomarkers were highlighted on the BAM. But the use of assistant generator also reduced the computational efficiency. In this example, the BAM generated only based on main generator (trained without cycled loss) was compared with the BAM generated from proposed framework. Compared to the BAM generated by the proposed framework including both the main generator and the assistant generator, the BAM generated only based on main generator (e.g., designed and trained without the assistant generator) highlighted wider areas including biomarkers not related to DR, such as non-disease microvasculature and large vessels (marked by green arrows in FIG. 17C). In addition, the fovea avascular zone could not be distinguished from the pathological non-perfusion areas in the BAM–S generated with the main generator alone (FIG. 17C). Therefore, the biomarkers which were not selected by the classifier would be also highlighted in the BAM if no assistant generator was used in the training.

FIGS. 18A and 18B illustrate the BAMs generated from false positive and negative classified inputs. FIG. 18A illustrates the OCTA channel of a non-referable DR input which was misclassified as referable DR (false positive) by the trained VGG19 classifier. FIG. 18B illustrates the OCTA channel of a referable DR input which was misclassified as non-referable DR (false negative) by the trained VGG19 classifier.

An important application of the BAM was reviewing whether an input was correctly classified based on the highlighted regions. Therefore, two BAMs respectively generated from a false positive and negative classified inputs were showed (FIG. 18). In the BAMs of misclassified inputs, the DR-related biomarkers and non-disease tissues were both highlighted, which means the trained classifier could not distinguish DR-related biomarkers from the non-disease tissues in these two inputs (FIG. 18). Therefore, these two inputs could be identified as misclassification through the generated BAMs.

To quantitatively analysis the BAM generation framework of this example, the F1-score between the segmented NPA and the binary mask of the BAM and other heatmaps were calculated (Table 3). In addition, the number of connected regions in each binary heatmap was also calculated (Table 3). The BAM achieved the highest F1-score compared to the other three heatmaps. At least one reason why the F1-score of the BAM was below 0.5 was that the BAM was generated to highlight the classifier-selected biomarkers not to find all DR biomarkers. In addition, the referable DR classification accuracy based on NPA was 92% which was lower than the trained VGG19-based classifier. The classifier finds more detailed correlations between DR biomarkers to achieve the 96% accuracy. Compared to the other three heatmaps, the number of connected regions of the BAM was also closer to the NPA, which showed that each biomarker was separately highlighted in the BAM.

TABLE 3

| Quantitative analysis of the BAM | | | | | |
|---|---|---|---|---|---|
| | IG | SGLRP | GradCAM | BAM-C | NPA |
| F1-score | 0.12 ± 0.03 | 0.11 ± 0.08 | 0.28 ± 0.08 | 0.41 ± 0.09 | 1.00 ± 0.00 |
| Connected regions | 2337 ± 257 | 197 ± 71 | 1 ± 0 | 34 ± 13 | 64 ± 20 |

Discussion

The BAM generation framework of this example provides for the interpretability of various the CNN-based disease classification systems. The framework was constructed by two U-shape CNN generators (main and assistant generator) and trained based on generative adversarial learning. The BAM was generated as the filtered difference map between the output and input of the main generator. The generated BAM could separately highlight each classifier-selected biomarker, which could be quickly discerned by clinicians in a real-world application. Compared to previously described interpretability methods, the proposed BAM generation framework is the first interpretability method that specifically designed for all the CNN-based disease classification systems. The BAM generation framework was evaluated on a trained DR classifier based on VGG19, which achieved 96% overall accuracy. Based on the comparison between the BAM and heatmaps generated by other methods, this framework achieved the state-of-the-art performance in providing interpretability to DR classification system based on OCT and OCTA. By providing sufficient interpretability, the BAM generation framework could improve the real-world application of CNN-based disease classification systems. In addition, by figuring out which biomarkers were learned by the classifier for a selected disease, the framework may also facilitate the new biomarker discovery on the input medical images used for diagnosis of the selected disease.

This framework is at least partially enabled by the unique features of disease classification compared to general image classification. In disease classification, the images of multiple severities share a similar background which is the anatomical structure that is present in a non-disease image. By separating a multi-severity classification to several binary classifications, among any two classes, only the higher severity image has unique biomarkers. The lower severity is classified based on the lack of unique biomarkers that belong to the higher-severity image. BAMs can highlight classifier-selected unique biomarkers belonging to higher severity images.

This framework applies generative adversarial learning with at least three innovations. First, in traditional generative adversarial learning, the classifier and generator are trained at the same time to generate images that are like the reference. But in the BAM generation framework described in this example, the direct training goal is generating outputs from disease or higher severity inputs that can be classified as non-disease or lower severity by a pre-trained disease classifier. Therefore, the generators in the framework were trained after the training and validation of a disease classifier. In addition, to maintain the performance of the classifier, the parameters of the trained classifier were not modified while the BAM generation framework was trained. During training, the main generator can learn which biomarkers in the input should be removed to let the trained classifier change the classification decision from disease or higher severity to non-disease or lower severity.

A second innovation was the architecture of the generators in the framework. Compared with CNNs used in traditional generative adversarial learning, a Tanh activation function was used after the last convolutional layer in the generators of this example. The generators were trained to only change necessary biomarkers that were learned by the classifier. The outputs are calculated as the sum between the input and the feature maps after Tanh activation. In addition, the outputs are clipped to the original value range of the inputs.

A third innovation of the framework is using an assistant generator, but selecting the model based on the validation loss of the main generator. The main generator, alone, can be susceptible to overfitting the outputs by changing non-disease anatomical structure of the inputs (FIG. 17C). Therefore, the assistant generator is used to calculate the cycled loss to make sure only the classifier-selected biomarkers are changed by the main generator. The assistant generator uses non-disease or lower severity images as inputs to generate the images that can be classified as disease or higher severity by the trained classifier. Unlike the main generator, which removes the unique biomarkers with exact locations, the assistant generator adds these biomarkers belonging to disease or higher severity without certain locations. Therefore, the validation loss of the main generator was used for model selection since there is not certain outputs for the assistant generator. That is, the assistant generator was trained to generate forged disease output from a normal input, which means the generator adds disease biomarkers to the input. The disease biomarkers can be added to many different locations in the normal input as long as the output can be classified as a disease image. Therefore, there are no specific outputs of the assistant generator since biomarkers can be added almost anywhere.

Unlike other interpretability methods, the BAM generation framework of this example utilizes deep learning networks to interpret another deep learning network, which leads to a question about the interpretability of the overall framework. For networks in which the training target is classification or segmentation, the interpretability issue can be described as how the classification or segmentation results are acquired. In medical image analysis, the concern for interpretability can be further described as whether the clinically meaningful biomarkers are used by the network to make the decision. However, the training target of the example framework is generating an output which can be classified as non-disease or lower severity by the trained classifier from a disease or higher severity input. The interpretability issue is how the output is generated to fulfill the requirement and which biomarkers are used by the example framework. The BAM, which is calculated as the difference image between the output and input, solves the interpretability issue of the framework by highlighting the biomarkers that were changed by the framework. Therefore, the BAM generation framework is self-interpreted and can be used to provide interpretability to CNN-based disease classifiers.

Conclusion

This example utilizes a BAM generation framework which could be used to provide sufficient interpretability to deep-learning-aided disease classification systems. The generated BAM could separately highlight each classifier-selected biomarker which could be quickly reviewed by clinicians to verify whether clinically meaningful biomarkers were learned and used by the classifier. The BAM generation framework of this example could improve the clinical acceptability and real-world applications of various deep-learning-aided disease classification systems, not just the DR classifier described in this example. The framework may also facilitate the new biomarker discovery on the input medical images used for diagnosis of related diseases.

Third Example

Deep learning (DL) can assist the diagnosis of diabetic retinopathy (DR) based on optical coherence tomography angiography. However, it is unclear how deep learning classification models arrive at their results, limiting discovery of DR biomarkers. To improve interpretability, a novel biomarker activation map (BAM) generation framework based on generative adversarial learning (GAL) is proposed.

Figures 19A, 19B:
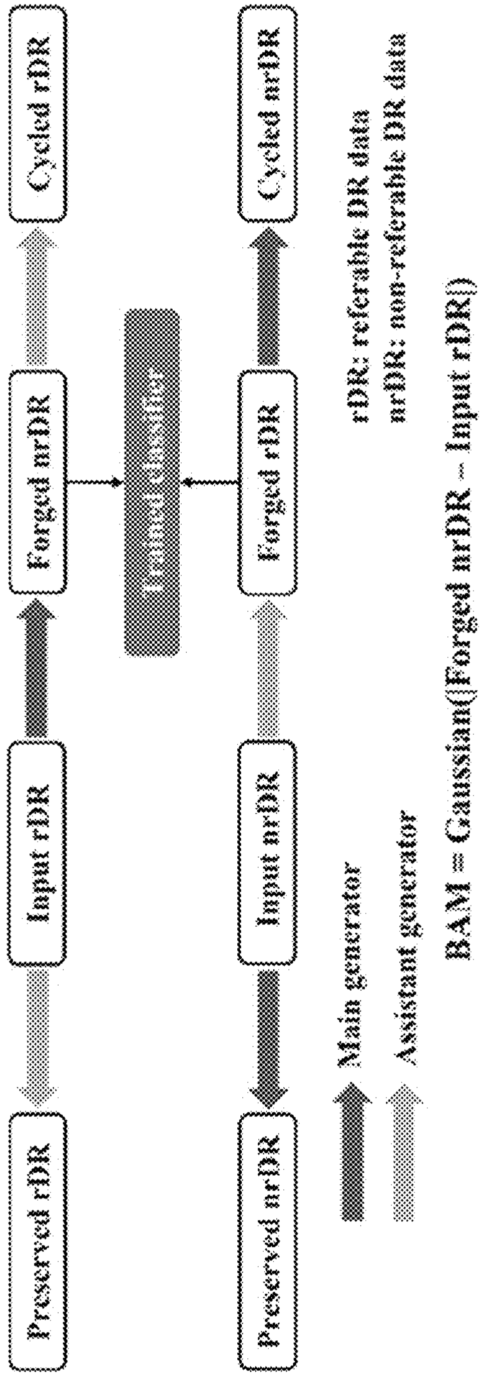
FIGS. 19A and 19B illustrates an architecture for training the main and assistant generators of an example.

FIG. 19 illustrates an architecture for training the main and assistant generators of this example. In this example, two generators were trained to produce BAMs. (A) an input of referable DR (rDR) angiograms are acted on by the main and assistant generators (green and blue arrows, respectively). The main generator trains to produce a forged angiogram from this input that the classifier will classify as non-referable DR (nrDR). The assistant generator also acts on this input rDR data and trains to produce a preserved rDR angiogram. For rDR input, the classifier and the assistant generator are then applied to the forged nrDR output of the main generator to produce a classification and a cycled rDR angiogram. Training is performed by optimizing the 1) categorical cross entropy between the forged label (here, nrDR) and the classifier output, and 2) the mean absolute errors between the input rDR and the cycled and preserved rDR angiograms. This scheme prevents the main generator from overfitting the forged nrDR (such as a blank image). (B) training from an nrDR input is symmetric, with the labels switching roles.

Figure 20A:
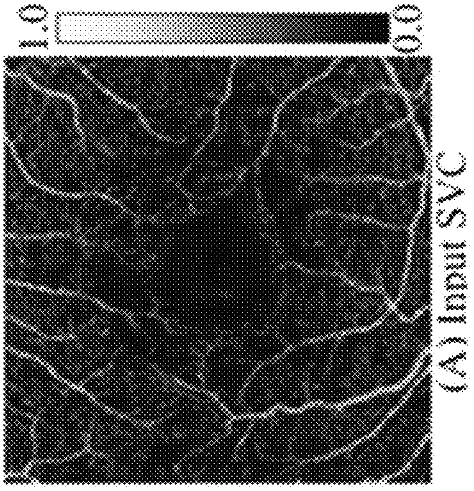
FIGS. 20A to 20E illustrates a comparison between the traditional CAM and novel BAM. (A) illustrates an input superficial vascular complex (SVC) which can be correctly classified as referable DR based on the trained classifier.
Figure 20B:
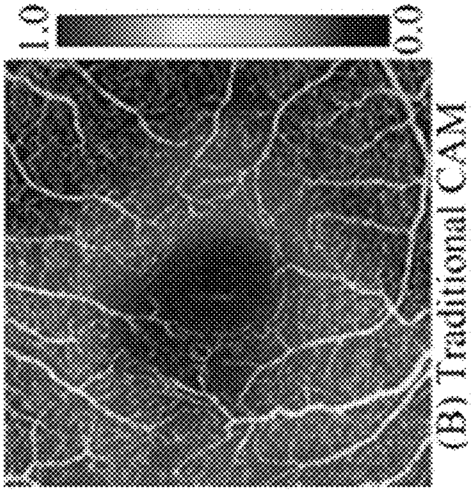
Figure 20C:
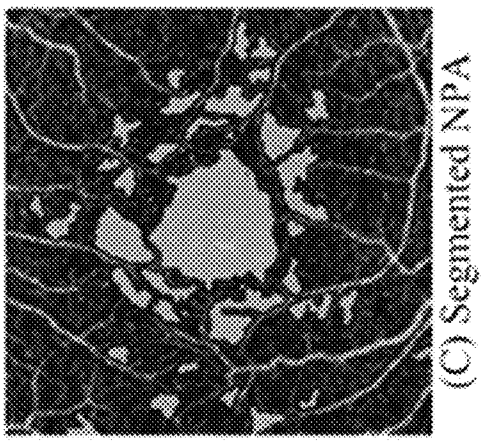
Figure 20D:
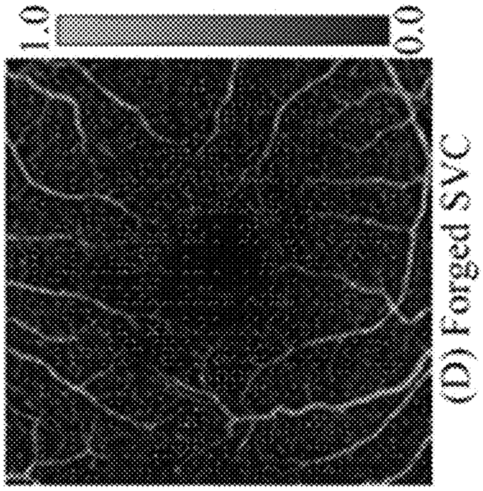
Figure 20E:
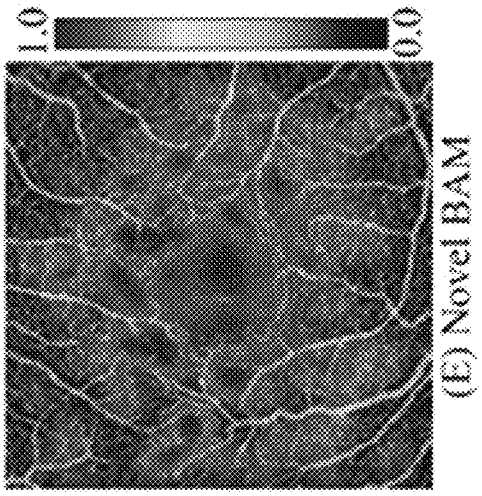

FIGS. 20A and 20E illustrates a comparison between the traditional CAM and novel BAM. FIG. 20A illustrates an input superficial vascular complex (SVC) which can be correctly classified as referable DR based on the trained classifier. FIG. 20B illustrates a traditional CAM of FIG. 20A based on Grad-CAM. FIG. 20C illustrates segmented non-perfusion area based on a previously reported deep learning method. FIG. 20D shows the forged SVC which was acquired from the main generator using FIG. 20A as an input. After the bright dots were added by the generator to the input SVC, it was classified as non-referable DR by the classifier. FIG. 20E illustrates the BAM which was calculated as the absolute difference between FIGS. 20A and 20D after Gaussian filtering. The BAM focuses on pathological non-perfusion area while ignoring the foveal avascular zone, in contrast to the CAM which focuses on features that are not pathological. Thus, the BAM more accurately identifies biomarkers associated with DR than the CAM.

In this example, 50 healthy participants and 305 patients with diabetes were recruited in this study. Masked trained retina specialists graded each eye based on 7-field fundus photography using early treatment of diabetic retinopathy study (ETDRS) criteria as either non-referable (nrDR; ETDRS score<35) or referable (rDR; ETDRS score 35 or macular edema). Macular 3×3-mm scans for one or both eyes of each participant were acquired using a commercial 70-kHz spectral-domain OCT system. 456 superficial vascular complex (SVC) en face OCTA images were collected. The data set was divided into training (60%), validation (20%), and testing (20%) sets and used to train a referable/non-referable DR classifier that used the en face SVC angiograms as input. Two U-shaped networks were also trained as generators. The main generator was trained to produce an angiogram that the classifier would classify as nrDR from an input angiogram, while the assistant generator produces angiograms that would be classified as rDR (FIG. 19). The BAM was finally constructed as the absolute difference image between the input angiogram and output of the main generator.

The diagnosis of rDR achieved an overall accuracy of 92%. Compared to the traditional class activation maps (CAMs) (FIG. 20B), the generated BAMs explicitly highlighted most of the pathological nonperfusion area, which represents the most important DR biomarker visible in the input angiogram (FIG. 20E). Unlike traditional CAMs, the BAMs ignored non-pathological features like the foveal avascular zone while emphasizing real pathological features that contribute the diagnostic decision making.

The generated BAMs using GAL method could provide sufficient interpretability to help clinicians utilize DL-aided referable DR screening, and help to quickly discern the DR-related pathologies. This innovation may also facilitate the new biomarker discovery on OCTA used for diagnosis of retinal vascular diseases.

Fourth Example

In this Example, the BAM of the First Example was quantitatively compared with three other attention maps. As shown in Table 4, the F1-score, intersection over union (IoU), precision and recall were calculated between the segmented biomarkers and binary masks of each attention map.

TABLE 4

Quantitative comparison.

| | F1-score | | IoU | | Precision | | Recall | |
|---|---|---|---|---|---|---|---|---|
| Methods | NPAs | Fluids | NPAs | Fluids | NPAs | Fluids | NPAs | Fluids |
| Gradient | 0.39 ± 0.07 | 0.09 ± 0.13 | 0.25 ± 0.05 | 0.05 ± 0.08 | 0.32 ± 0.08 | 0.05 ± 0.08 | 0.56 ± 0.14 | 0.70 ± 0.29 |
| Propagation | 0.33 ± 0.10 | 0.14 ± 0.19 | 0.20 ± 0.08 | 0.09 ± 0.14 | 0.58 ± 0.19 | 0.13 ± 0.22 | 0.24 ± 0.09 | 0.41 ± 0.35 |
| CAM | 0.44 ± 0.08 | 0.11 ± 0.16 | 0.29 ± 0.07 | 0.07 ± 0.11 | 0.42 ± 0.10 | 0.07 ± 0.12 | 0.51 ± 0.15 | 0.60 ± 0.34 |
| BAM | 0.63 ± 0.08 | 0.14 ± 0.21 | 0.47 ± 0.09 | 0.09 ± 0.15 | 0.64 ± 0.16 | 0.20 ± 0.31 | 0.65 ± 0.08 | 0.25 ± 0.31 |

The binary mask of each map was generated based on threshold mean+std×0.1. The OCTA channels of each attention map were compared with segmented NPAs. On this channel, the BAM achieved significantly higher performance than the other three attention maps (Table 4). On the OCT channels, which were compared with segmented fluids, the BAM still achieved higher performance based on most measurements. The results indicate that the BAM may have lower recall for identifying fluids. But the higher precision and lower recall of the BAM actually demonstrates that the method focused on the part of the DR biomarkers which were utilized by the classifier while ignoring the healthy tissues. The lower precision and higher recall of these established attention maps can be attributed to the fact that they highlighted a large area which included more healthy tissues than DR biomarkers, which is not clinically meaningful. In addition, all four attention maps achieved higher performance on the OCTA channel than the OCT channel, which means the classifier was more focused on the NPAs rather than fluids.

To assess if the BAM techniques were correlated with the interpreted DR classifier, two checks were performed (J. Adebayo et al. in *Proc. Adv. Neural. Inf. Process. Syst*, 2018). First, model parameter and data randomization tests were performed. In the model parameter randomization test, DR classifier parameters were divided into six parts based on the five max pooling layers. The parameters in each of the six parts were randomized in two ways. In cascading randomization, the parameters were randomized from the top part of the trained DR classifier (after last max pooling) successively all the way to the bottom part (before first max pooling). In the independent randomization, the parameters in each part were randomized independently. All the parameter randomizations in this Example created 11 different models. In the data randomization test, a model with the same architecture of the DR classifier was trained based on randomized labels. The model training was stopped after the training accuracy reached 95%. The generated BAMs of these 12 models were compared with the BAMs generated based on the original DR classifier. For quantitative comparison, the Spearman rank correlation was calculated, the structural similarity index (SSIM), and the Pearson correlation of the histogram of gradients (HOGs) between the $BAM_{(+/-)}$ generated on these models and the original classifier. Most models in the parameter randomization test predicted the data as being of the same class (either non-referable or referable DR), which means no BAMs were generated for these models, since the training of the framework utilized data predicted as both classes. In the cascading randomization, only the model with randomized parameters after the 4th max pooling layer had predictions for both classes. In the independent randomization, only the model with randomized parameters before the first max pooling layer had predictions for both classes. Therefore, these two models were used to represent the cascading and independent parameter randomizations, respectively.

Figures 21A, 21B, 21C, 21D, 21E:
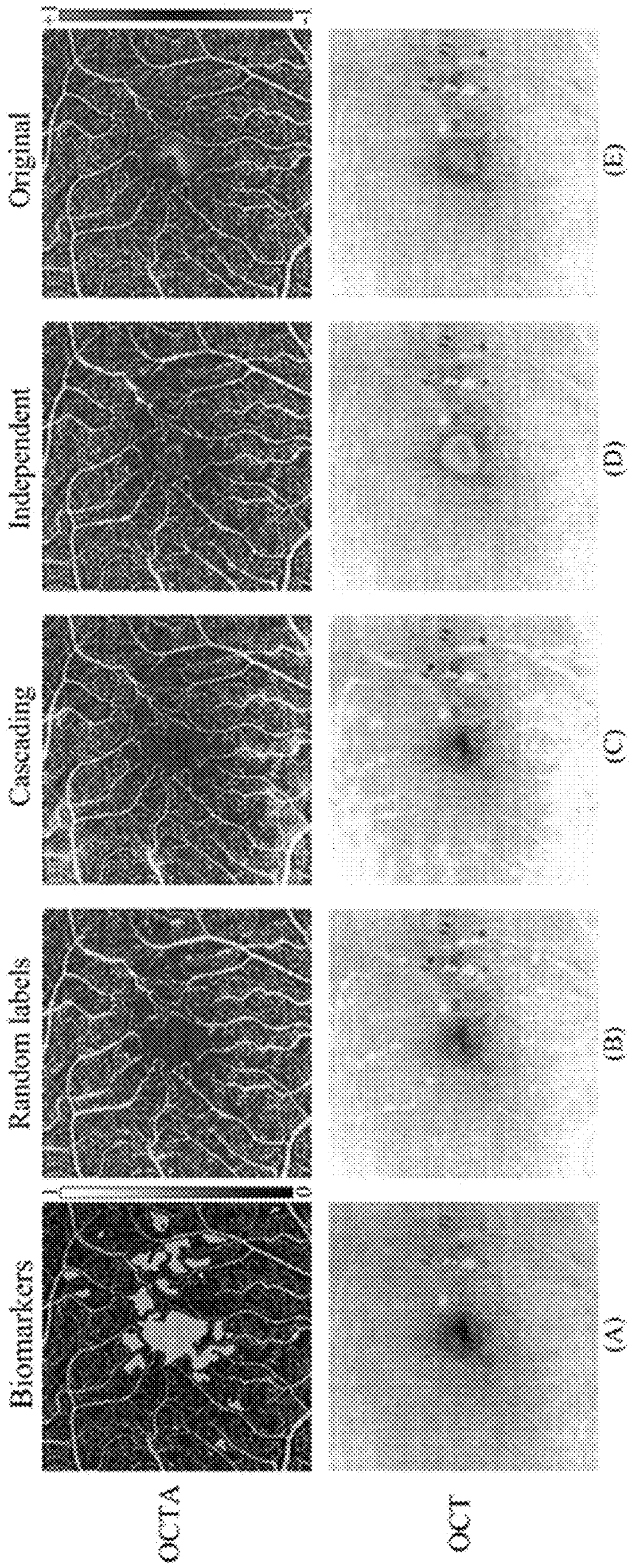
FIGS. 21A to 21E illustrate that the BAMs generated in this example were sensitive to the interpretability changes between different randomized models.

FIGS. 21A to 21E illustrate that the BAMs generated in this example were sensitive to the interpretability changes between different randomized models. FIG. 21A illustrates segmented non-perfusion areas and fluids. FIG. 21B illustrates the $BAM_{(+/-)}$ of the model based on randomized labels. FIG. 21C illustrates the $BAM_{(+/-)}$ of the model based on cascading parameter randomization. FIG. 21D illustrates the $BAM_{(+/-)}$ of the model based on independent parameter randomization. FIG. 21E illustrates the $BAM_{(+/-)}$ generated based on the original DR classifier. Table 5 (below) illustrates the quantitative results of this analysis.

TABLE 5

Quantitative confirmation of results

| Models | Spearman rank correlation OCTA | Spearman rank correlation OCT | SSIM OCTA | SSIM OCT | HOGs OCTA | HOGs OCT |
|---|---|---|---|---|---|---|
| Random labels | −0.11 ± 0.17 | 0.22 ± 0.22 | 0.13 ± 0.07 | 0.75 ± 0.11 | 0.07 ± 0.06 | 0.01 ± 0.09 |
| Cascading randomization | −0.21 ± 0.06 | 0.11 ± 0.03 | 0.18 ± 0.10 | 0.24 ± 0.11 | 0.00 ± 0.06 | −0.09 ± 0.06 |
| Independent randomization | 0.45 ± 0.14 | 0.82 ± 0.11 | 0.30 ± 0.12 | 0.91 ± 0.12 | 0.05 ± 0.05 | 0.54 ± 0.15 |

The three BAMs generated in both parameter and label randomization tests showed large differences compared to the original BAMs (FIG. 21 and Table 5), which shows that the BAMs may be sensitive to potential interpretability changes of the classifier. The two models based on randomized labels and cascading parameter randomization highlighted totally different regions compared to the original BAMs. The highlighted regions in the model based on independent randomization had some overlaps with the original BAMs. But the differences between these two BAMs were still large and clear.

Fifth Example

In an example of the framework, both $M_{(+/-)}$ and $L_c$ losses were used to ensure that the BAM framework only highlighted the classifier-utilized biomarkers. But the use of these two losses also reduced the computational efficiency. To explore its merit, BAMs generated from the proposed framework of the First Example were compared with three variations. The first variation was trained only based on $H_-$, which means no non-referable DR data or the assistant generator were used. The second variation was trained based on $H_-$ and $L_c$, which means no preserved output was generated. The third variation was trained based on $H_-$ and $M_-$, which means no assistant generator was used.

Figures 22A, 22B, 22C, 22D, 22E:
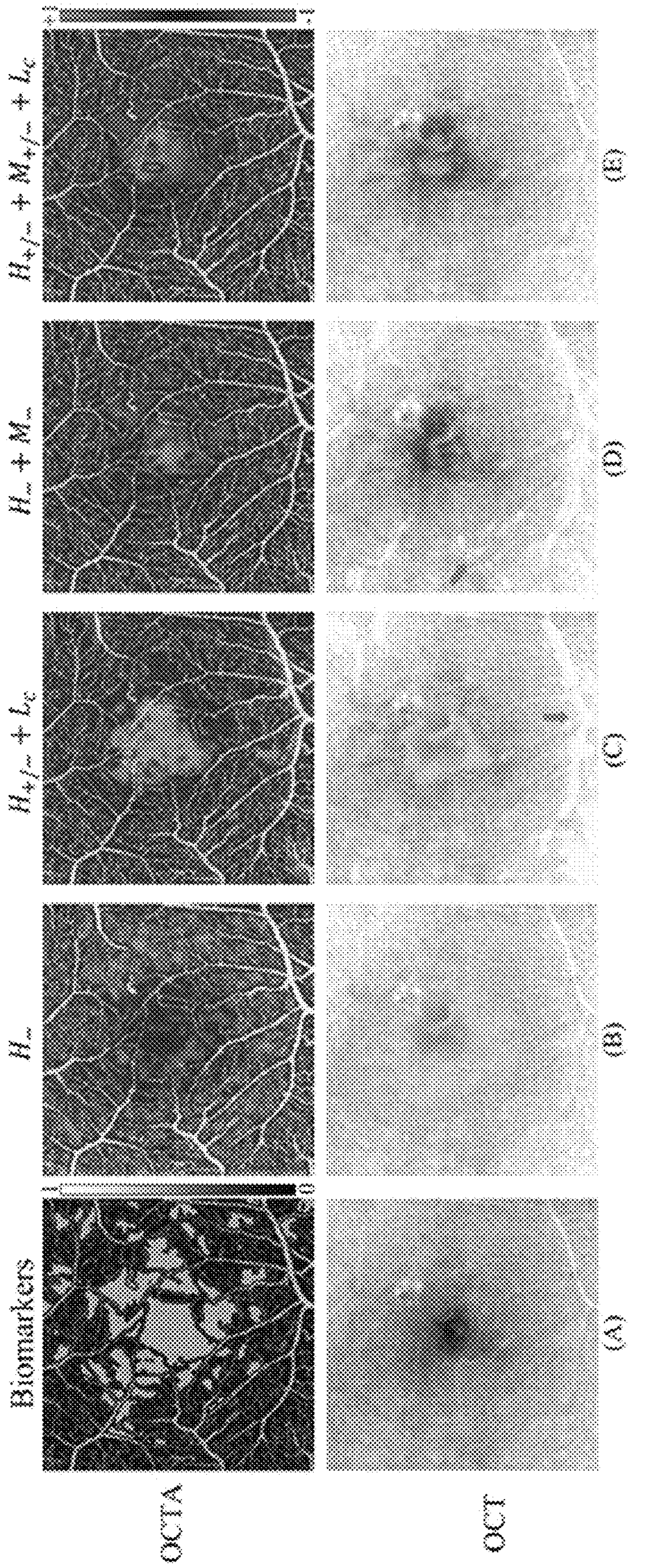

FIGS. 22A to 21E illustrate BAMs generated in the ablation experiments. Large vessels highlighted by the three variations are marked by blue arrows. FIG. 22A illustrates non-perfusion areas and fluids. FIG. 22B illustrates the $BAM_{(+/-)}$ generated without non-referable DR data and assistant generator (loss: $H_-$). FIG. 22C illustrates the $BAM_{(+/-)}$ generated without preserved output (loss: $H_{(+/-)}+L_c$). FIG. 22D illustrates the $BAM_{(+/-)}$ generated without the assistant generator (loss: $H_-+M_-$). FIG. 22E illustrates the $BAM_{(+/-)}$ generated based on proposed framework (loss: $H_{(+/-)}+M_{(+/-)}+L_c$).

Except for the BAMs generated from the proposed framework, the BAMs of the three variations highlighted features not related to DR pathology such as normal microvasculature and large vessels (marked by blue arrows in FIG. 22). In addition, the foveal avascular zone could not be distinguished from the pathological NPAs in the $BAM_{(+/-)}$ generated with these three training variations (FIG. 22).

Sixth Example

An example BAM generation framework was also evaluated for its ability to recognize other types of diseases. The first classifier was trained on a fundus photography data set with 326 age related macular degeneration (AMD) subjects and 500 healthy controls (A. Maranhao (2021), Ocular Disease Recognition; S. Pachade et al., 2021, Data, 6(2), p. 14). The second classifier was trained on a brain MRI data set with 1500 subjects with brain tumor and 1500 healthy controls (Msoud Nickparvar (2021), *Brain Tumor MRI Database*). The third classifier was trained on a breast CT data set with 1200 subjects with breast cancer and 1200 healthy controls (S. Malekzadeh (2022), *Breast Cancer CT* (*Fully Preprocessed*)). The trained classifiers achieved 0.85, 0.99, and 0.83 AUCs for AMD, brain tumor, and breast cancer diagnosis, respectively.

BAMs for AMD Classifier Based on Fundus Photography

Figure 23:
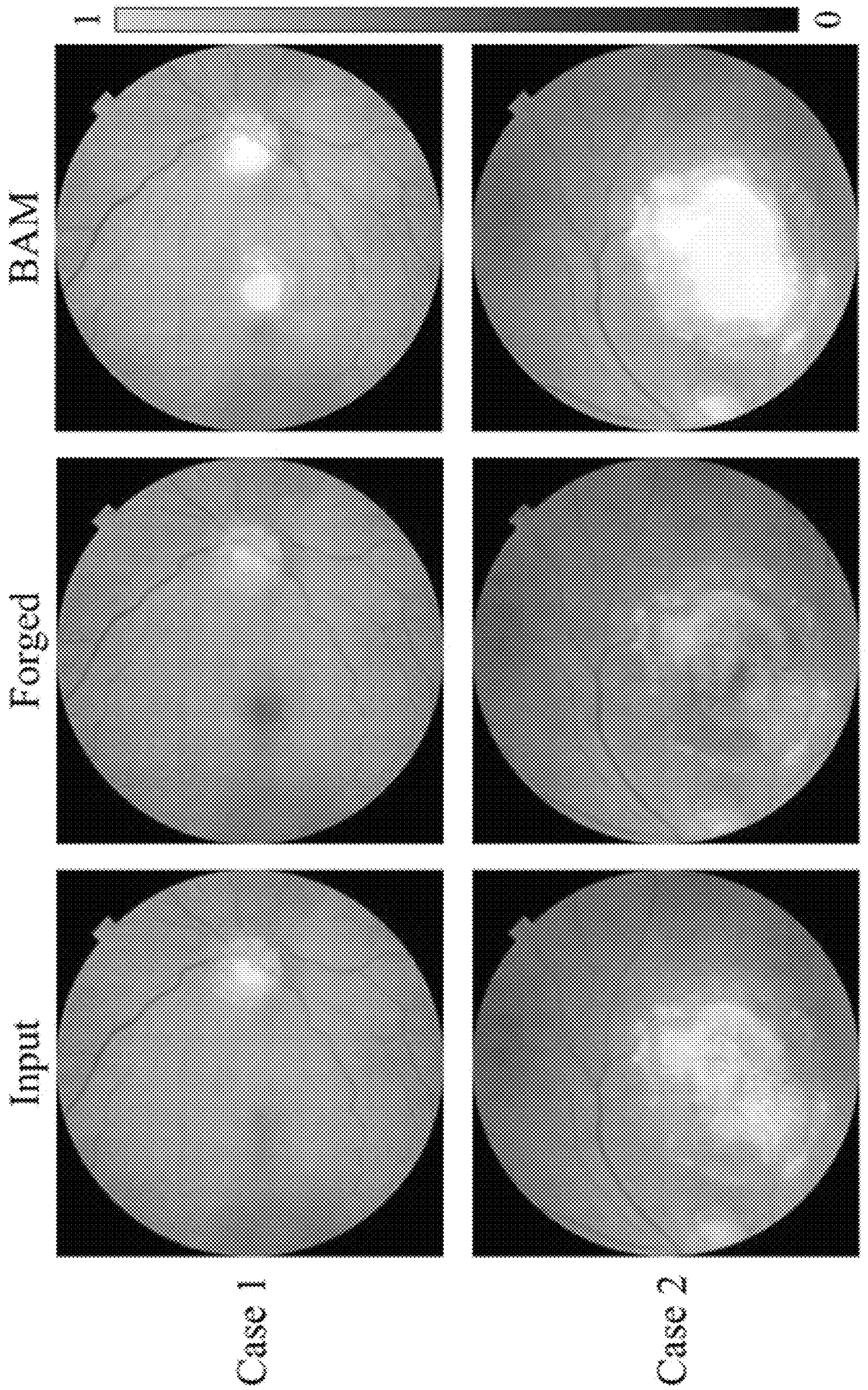
FIG. 23 illustrates generated BAMs for two correctly diagnosed AMD fundus photography images.

FIG. 23 illustrates generated BAMs for two correctly diagnosed AMD fundus photography images. The inputs could be correctly classified as AMD by the trained classifier. But after the changes were made by the BAM generation framework, the forged output could be then classified as healthy control by the same classifier. The BAM is the filtered absolute difference between forged and input images of each case. The AMD-related and classifier-utilized biomarkers were accurately highlighted by the BAMs.

In an intermediate AMD case, the generated BAMs accurately highlighted the areas with drusen and pigmentary abnormalities (case 1 in FIG. 23). In advanced AMD case, the generated BAMs accurately highlighted the areas with choroidal neovascularization (CNV) (case 2 in FIG. 23).

BAMs for Brain Tumor Classifier Based on MRI

Figure 24:
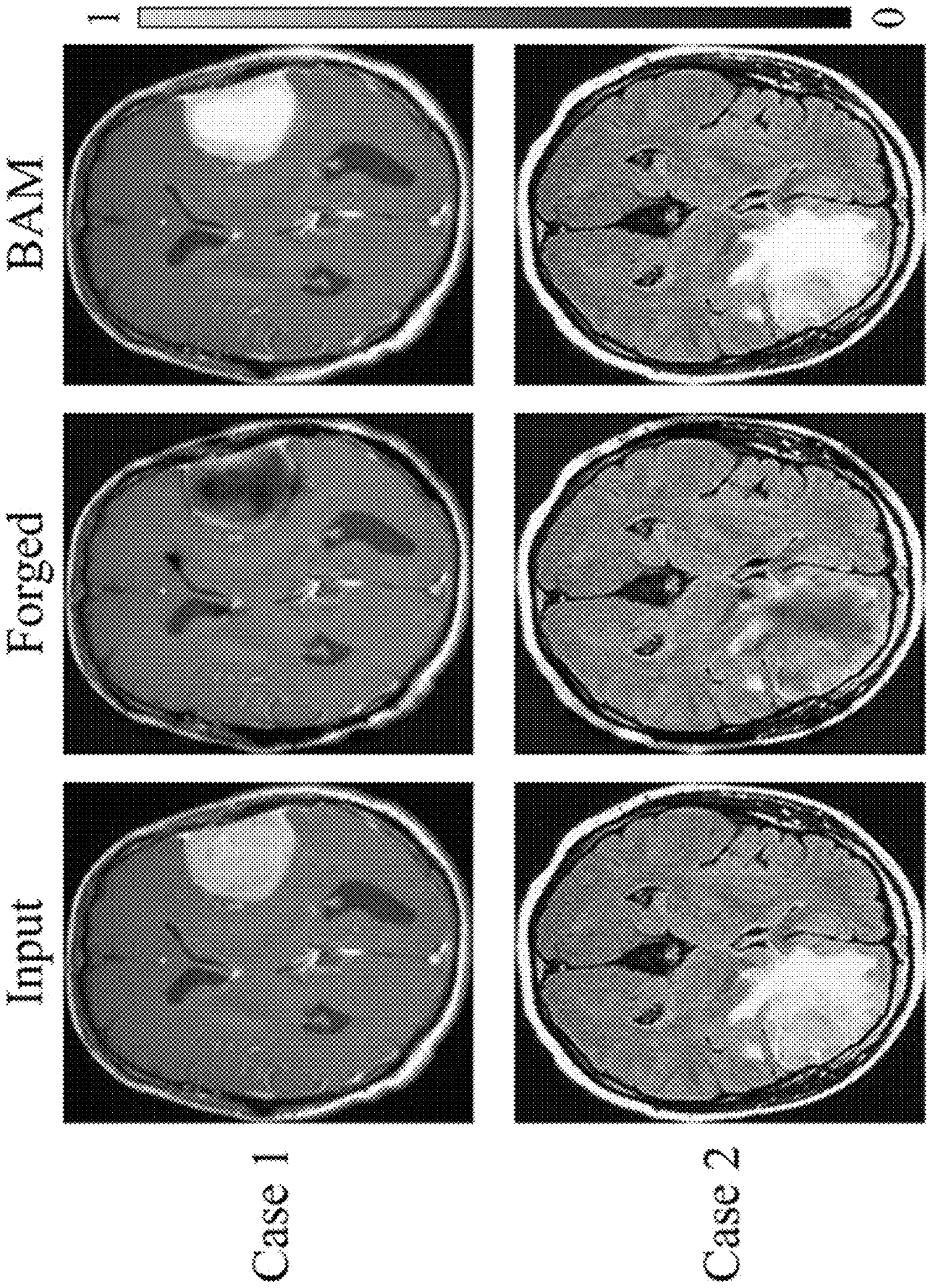
FIG. 24 illustrates generated BAMs for two correctly diagnosed brain tumor MRI images.

FIG. 24 illustrates generated BAMs for two correctly diagnosed brain tumor MRI images. The inputs could be correctly classified as brain tumor by the trained classifier. But after the changes were made by the BAM generation framework, the forged output could be then classified as healthy control by the same classifier. The BAM is the filtered absolute difference between forged and input images of each case. The classifier-utilized brain tumor areas were accurately highlighted by the BAMs.

The highlighted regions in the BAMs generated for the brain tumor classifier based on MRI also showed high correlation with the real tumor areas (FIG. 24). In case 1, the BAM accurately highlighted the brain tumor area with a sharp boundary, which means the classifier correctly learned the difference between background normal tissue and brain tumor. In case 2, most of the brain tumor areas were highlighted by the BAM, which means the classifier only utilized part of the brain tumor for the diagnosis. In addition, the pixels' intensity in the brain tumor areas of both cases were decreased in the forged outputs, which means the classifier learned that the pixel intensity of surrounding healthy tissues should be lower than the tumor area in these two cases. Except for the tumor areas, some bright edges were also highlighted by the BAMs. The reason for the highlighting may be that some brain tumors also have bright edges, and the classifier could not fully distinguish the differences between the brain and tumor edges. Based on all the BAMs evaluated on the testing set, this Example shows that the MRI-based brain tumor classifier learned correct biomarkers for the diagnosis.

BAMs for Breast Cancer Classifier Based on CT

Figure 25:
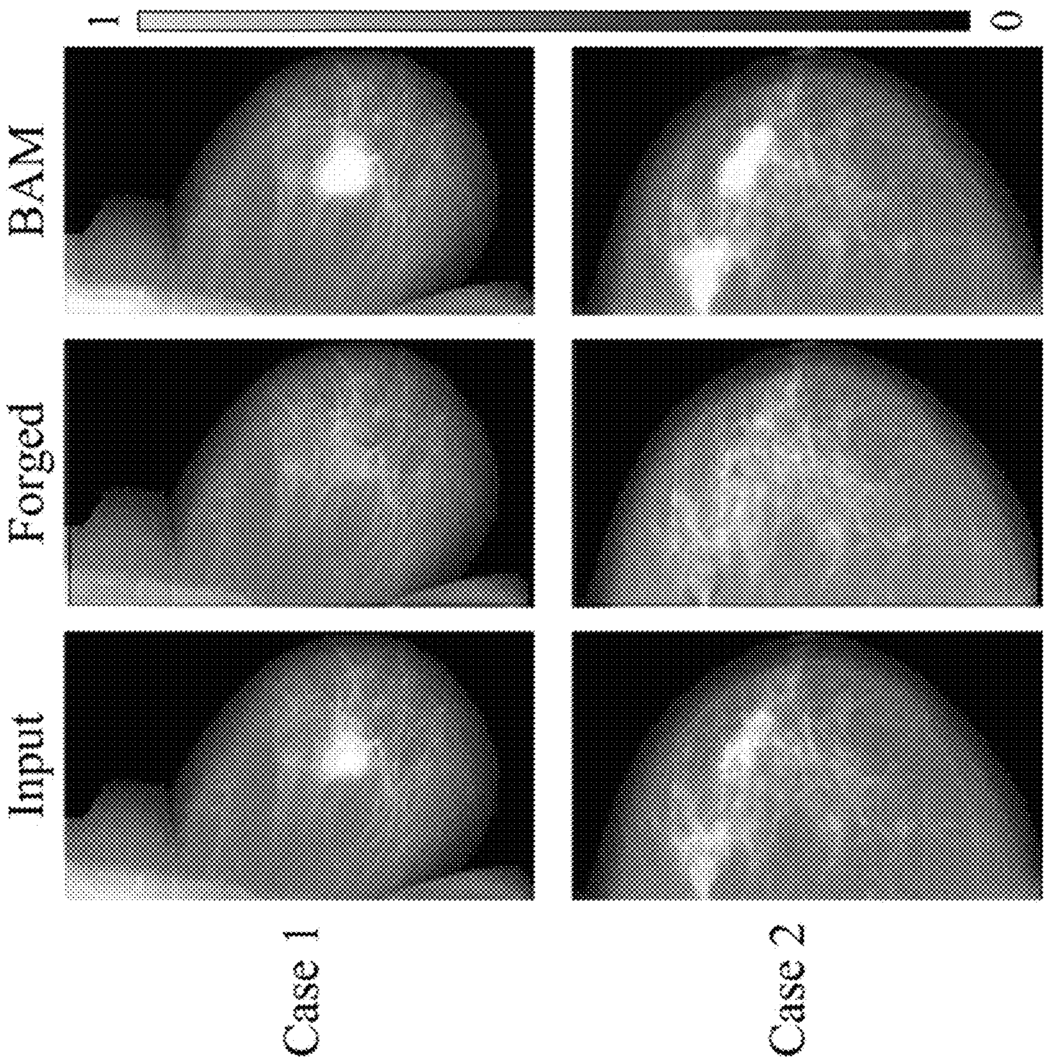
FIG. 25 illustrates BAMs for two correctly diagnosed breast cancer CT images.

For the CT-based breast cancer classifier, the BAMs were generated on the testing set with high accuracy. FIG. 25 illustrates BAMs for two correctly diagnosed breast cancer CT images. The inputs could be correctly classified as breast cancer by the trained classifier. But after the changes were made by the BAM generation framework, the forged output could be then classified as healthy control by the same classifier. The BAM is the filtered absolute difference between forged and input images of each case. In the BAMs, the classifier-utilized biomarkers were highlighted and showed high correlation with the real breast-cancer-related biomarkers.

In the BAMs of both cases, most of the highlighted regions have high correlation with the breast cancer-related biomarkers. In the forged outputs, the changed biomarkers look similar to the surrounding tissues, which means only necessary changes were made by the generation framework. In addition, parts of the bright edges were also highlighted by the BAMs, which means the classifier misidentified these edges as cancer-related biomarkers.

Example Clauses

The following clauses provide various implementations of the present disclosure.

1. A medical imaging system, including: an imaging device configured to capture an ophthalmic image of a retina; a display; at least one processor; and memory storing instructions that, when executed by the at least one processor, cause the at least one processor to perform operations including: generating a first output image by inputting the ophthalmic image into a trained U-shaped neural network (NN); generating a second output image by inputting the first output image into an activation layer; generating a third output image by adding the ophthalmic image to the second output image; generating a biomarker activation map (BAM) by clipping the third output image; and causing the display to visually output the BAM overlaid on the ophthalmic image, the BAM indicating at least one biomarker in the ophthalmic image that is indicative of an ophthalmic disease.
2. The medical imaging system of clause 1, wherein the imaging device is configured to capture the ophthalmic image by performing at least one of an optical coherence tomography (OCT) or an optical coherence tomography angiography (OCTA) scan on the retina.
3. The medical imaging system of clause 1 or 2, wherein the ophthalmic image includes multiple channels respectively corresponding to different imaging modalities.
4. The medical imaging system of one of clauses 1 to 3, wherein generating the first output image by inputting the ophthalmic image into the trained U-shaped NN includes: generating a first intermediary image based on the ophthalmic image; generating a second intermediary image by inputting the first intermediary image into a first residual block, the first residual block including at least one first convolution block; generating a third intermediary image by inputting the second intermediary image into a second residual block, the second residual block including at least one second convolution block; generating a fourth intermediary image by inputting the third intermediary image into a deconvolution block; generating a fifth intermediary image by concatenating the second intermediary image and the fourth intermediary image; and generating the first output image based on the fifth intermediary image.
5. The medical imaging system of one of clauses 1 to 4, wherein the ophthalmic disease includes diabetic retinopathy (DR).
6. The medical imaging system of one of clauses 1 to 5, wherein the ophthalmic disease includes a first level of severity and a second level of severity, and wherein the at least one biomarker is indicative of the first level of severity or the second level of severity.

7. The medical imaging system of one of clauses 1 to 6, the ophthalmic image being a first ophthalmic image, the retina being a first retina, wherein the operations further include: training the U-shaped NN based on training data including second ophthalmic images depicting second retinas and indications of whether the second retinas are indicative of the ophthalmic disease.

8. The medical imaging system of clause 7, wherein a main generator includes the U-shaped NN, the U-shaped NN being a first U-shaped NN, and wherein training the first U-shaped NN includes: identifying a classifier configured to identify a level of the ophthalmic disease depicted in the ophthalmic image; identifying an assistant generator including a second U-shaped NN; and training the main generator based on the classifier, the assistant generator, and the training data.

9. A method, including: identifying a medical image depicting at least a portion of a subject; generating a biomarker activation map (BAM) by inputting the medical image into a trained, U-shaped neural network (NN); and outputting the BAM overlaying the medical image, the BAM indicating at least one biomarker depicted in the medical image that is indicative of a disease.

10. The method of clause 9, wherein the medical image includes at least one of an x-ray image, a magnetic resonance imaging (MRI) image, a functional MRI (fMRI) image, a single-photon emission computerized tomography (SPECT) image, a positron emission tomography (PET) image, an ultrasound image, an infrared image, a computed tomography (CT) image, an optical coherence tomography (OCT) image, or an OCT angiography (OCTA) image, a color fundus photograph (CFP) image, a fluorescein angiography (FA) image, or an ultra-widefield retinal image.

11. The method of clause 9 or 10, wherein the medical image includes multiple channels respectively corresponding to different imaging modalities.

12. The method of one of clauses 9 to 11, wherein generating the BAM by inputting the medical image into a trained, U-shaped NN includes: generating a first intermediary image based on the medical image; generating a second intermediary image by inputting the first intermediary image into a first residual block, the first residual block including at least one first convolution block; generating a third intermediary image by inputting the second intermediary image into a second residual block, the second residual block including at least one second convolution block; generating a fourth intermediary image by inputting the third intermediary image into a deconvolution block; generating a fifth intermediary image by concatenating the second intermediary image and the fourth intermediary image; and generating the BAM based on the fifth intermediary image.

13. The method of clause 12, wherein generating the BAM based on the fifth intermediary image includes: generating a first output image based on the fifth intermediary image; generating a second output image by inputting the first output image into a third convolution block; and generating the BAM based on the second output image.

14. The method of clause 13, wherein generating the BAM based on the second output image includes: generating a third output image by performing Tanh activation on the second output image; and generating a fourth output image by adding the medical image to the third output image; and generating the BAM based on the fourth output image.

15. The method of clause 14, wherein generating the BAM based on the fourth output image includes: clipping the fourth output image.

16. The method of one of clauses 9 to 15, wherein outputting the BAM overlaying the medical image includes causing a display to visually output the BAM overlaying the medical image.

17. The method of one of clauses 9 to 16, further including: predicting a level of the disease depicted by the medical image by inputting the medical image into a trained classifier; and outputting the level of the disease.

18. The method of clause 17, wherein the trained classifier includes a VGG19 classifier.

19. The method of one of clauses 9 to 18, the U-shaped NN being a first U-shaped NN, the medical image being a first medical image, wherein a main generator includes the first U-shaped NN, and wherein the method further includes training the first U-shaped NN by: identifying a classifier trained to identify the presence and/or absence of the disease in the first medical image; identifying an assistant generator including a second U-shaped NN; identifying training data including second medical images and indications of whether the second medical images depict the disease; and training the main generator, the classifier, and the assistant generator based on the training data.

20. A method, including: identifying a medical image; identifying a label indicating whether the medical image depicts a disease; generating, using a main generator, a forged image based on the medical image; generating, using an assistant generator, a cycled image based on the forged image, the main generator and the assistant generator sharing a U-shaped architecture; identifying a first discrepancy between the cycled image and the medical image; generating, using the assistant generator, a preserved image based on the medical image; identifying a second discrepancy between the preserved image and the medical image; and adjusting at least one parameter of the main generator and the assistant generator based on the first discrepancy and the second discrepancy.

21. The method of clause 20, further including: generating a forged label by inputting the forged image into a classifier, the classifier being trained to identify the presence of the disease in the medical image; comparing the forged label to an expected label; and adjusting at least one parameter of the main generator and the assistant generator based on comparing the forged label to the expected label.

22. A non-transitory computer-readable medium storing instructions for performing the method of one of clauses 9 to 21.

23. A system, including: at least one processor; and memory storing instructions that, when executed by the at least one processor, cause the at least one processor to perform operations including the method of one of clauses 9 to 21.

24. The system of clause 23, further including: an imaging device configured to generate the medical image.

25. The system of clause 23, further including: a display configured to visually output the medical image and/or the BAM.

CONCLUSION

The environments and individual elements described herein may of course include many other logical, programmatic, and physical components, of which those shown in the accompanying figures are merely examples that are related to the discussion herein.

Other architectures may be used to implement the described functionality and are intended to be within the scope of this disclosure. Furthermore, although specific distributions of responsibilities are defined above for purposes of discussion, the various functions and responsibilities might be distributed and divided in different ways, depending on circumstances.

Furthermore, although the subject matter has been described in language specific to structural features and/or methodological acts, it is to be understood that the subject matter defined in the appended claims is not necessarily limited to the specific features or acts described. Rather, the specific features and acts are disclosed as exemplary forms of implementing the claims.

As will be understood by one of ordinary skill in the art, each embodiment disclosed herein can comprise, consist essentially of, or consist of its particular stated element(s), step(s), ingredient(s), and/or component(s). Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiments.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventors expect skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

It is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Explicit definitions and explanations used in the present disclosure are meant and intended to be controlling in any future construction unless clearly and unambiguously modified in examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. A method, comprising:

identifying a medical image depicting at least a portion of a subject;

generating, using a main generator, a modified image by removing at least one biomarker indicative of a disease from the medical image;

generating a biomarker activation map (BAM) as a difference image between the medical image and the modified image; and outputting the BAM overlaying the medical image, the BAM indicating the at least one biomarker depicted in the medical image that is indicative of the disease;

wherein the main generator is trained with an assistant generator, by:

identifying a classifier trained to identify a presence and/or an absence of the disease in the medical image;

identifying training data comprising one or more disease image indicated as depicting the disease and one or more non-disease image indicated as not depicting the disease;

performing an inverse task, using the assistant generator, to the main generator by generating at least one positive image based on the non-disease image from the training data, the positive image being classified by the classifier as depicting the disease;

and training the main generator and the assistant generator based on the training data and the classifier.

2. The method of claim 1, wherein the medical image comprises at least one of an x-ray image, a magnetic resonance imaging (MRI) image, a functional MRI (fMRI) image, a single-photon emission computerized tomography (SPECT) image, a positron emission tomography (PET) image, an ultrasound image, an infrared image, a computed tomography (CT) image, an optical coherence tomography (OCT) image, an OCT angiography (OCTA) image, a color fundus photograph (CFP) image, a fluorescein angiography (FA) image, or an ultra-widefield retinal image.

3. The method of claim 1, wherein the medical image comprises multiple channels respectively corresponding to different imaging modalities.

4. The method of claim 1, wherein generating the BAM comprises:

generating a first intermediary image based on the medical image;

generating a second intermediary image by inputting the first intermediary image into a first residual block, the first residual block comprising at least one first convolution block;

generating a third intermediary image by inputting the second intermediary image into a second residual block, the second residual block comprising at least one second convolution block;

generating a fourth intermediary image by inputting the third intermediary image into a deconvolution block;

generating a fifth intermediary image by concatenating the second intermediary image and the fourth intermediary image; and generating the BAM based on the fifth intermediary image.

5. The method of claim 4, wherein generating the BAM based on the fifth intermediary image comprises:

generating a first output image based on the fifth intermediary image;

generating a second output image by inputting the first output image into a third convolution block; and generating the BAM based on the second output image.

6. The method of claim 5, wherein generating the BAM based on the second output image comprises:

generating a third output image by performing Tanh activation on the second output image; and generating a fourth output image by adding the medical image to the third output image; and generating the BAM based on the fourth output image.

7. The method of claim 1, wherein outputting the BAM overlaying the medical image comprises causing a display to visually output the BAM overlaying the medical image.

8. The method of claim 1, further comprising:

predicting a level of the disease depicted by the medical image by inputting the medical image into a trained classifier; and outputting the level of the disease.

9. The method of claim 8, wherein the trained classifier comprises a VGG19 classifier.

10. The method of claim 1, wherein the disease comprises diabetic retinopathy (DR), macular degeneration, a tumor, or inflammation.

11. The method of claim 1, wherein the disease comprises a brain tumor or a breast tumor.

12. The method of claim 1, wherein the main generator is further trained with the assistant generator by:

generating, using the main generator, a forged non-disease image based on the disease image from the training data, the forged non-disease image being classified by the classifier as not depicting the disease;

generating, using the assistant generator, a forged disease image based on the non-disease image from the training data, the forged disease image being classified by the classifier as depicting the disease;

generating, using the assistant generator, a cycled disease image based on the forged non-disease image;

generating, using the main generator, a cycled non-disease image based on the forged disease image;

identifying a first discrepancy between the cycled disease image and the disease image and a second discrepancy between the cycled non-disease image and the non-disease image; and adjusting at least one parameter of the main generator and the assistant generator based on the first discrepancy and the second discrepancy.

13. The method of claim 12, wherein the main generator is further trained with the assistant generator by:

generating, using the main generator, a preserved disease image based on the disease image from the training data;

generating, using the assistant generator, a preserved non-disease image based on the non-disease image from the training data;

identifying a third discrepancy between the preserved disease image and the disease image and a fourth discrepancy between the preserved non-disease image and the non-disease image; and adjusting at least a second parameter of the main generator and the assistant generator based on the third discrepancy and the fourth discrepancy.

14. The method of claim 1, wherein the main generator comprises a first trained U-shaped neural network (NN) and the assistant generator comprises a second trained U-shaped NN.

* * * * *